US012357185B2

(12) United States Patent
Fornell

(10) Patent No.: US 12,357,185 B2
(45) Date of Patent: Jul. 15, 2025

(54) SYSTEM AND METHOD FOR MONITORING/DETECTING AND RESPONDING TO INFANT BREATHING

(71) Applicant: HB Innovations, Inc., Los Angeles, CA (US)

(72) Inventor: Peter Fornell, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 624 days.

(21) Appl. No.: 17/353,762

(22) Filed: Jun. 21, 2021

(65) Prior Publication Data

US 2021/0361172 A1 Nov. 25, 2021

Related U.S. Application Data

(63) Continuation-in-part of application No. 16/905,424, filed on Jun. 18, 2020, now Pat. No. 11,712,180.

(Continued)

(51) Int. Cl.
*A61B 5/0205* (2006.01)
*A61B 5/00* (2006.01)

(52) U.S. Cl.
CPC .......... *A61B 5/0205* (2013.01); *A61B 5/6892* (2013.01); *A61B 5/7225* (2013.01); *A61B 2503/045* (2013.01)

(58) Field of Classification Search
CPC ..... A61B 5/1135; A61B 5/002; A61B 5/0205; A61B 5/0823; A61B 5/1128; A61B 5/4818; A61B 5/6804; A61B 5/7225; A61B 5/7282; A61B 5/746; A61B 5/7465; A61B 2503/045; A61B 2562/0219;

(Continued)

(56) References Cited

U.S. PATENT DOCUMENTS 4,958,638 A 9/1990 Sharpe
6,468,234 B1* 10/2002 Van der Loos ...... A61B 5/6887
600/595

(Continued)

FOREIGN PATENT DOCUMENTS

AU 2015264875 12/2015
CN 1592778 3/2005

(Continued)

OTHER PUBLICATIONS

Notification of Transmittal of the International Search Report and Written Opinion of the International Searching Authority, mailed Sep. 14, 2020 in PCT/US2020/038477.

(Continued)

*Primary Examiner* — Brian T Gedeon
(74) *Attorney, Agent, or Firm* — Akeman LLP

(57) ABSTRACT

This disclosure generally relates to systems and methods for detecting, monitoring, and responding to abnormalities in a subject's breathing or heartbeat. One or more sensing devices may collect breathing or heartbeat related data, which may be filtered and converted to a frequency signal. The frequency signal may be monitored for irregularity or stoppage, and a processing module may determine whether the irregularity or stoppage is caused by an actual stoppage or irregularity in breathing or heartbeat. If breathing or heartbeat is determined to have stopped, a corrective action may be performed.

16 Claims, 30 Drawing Sheets

Related U.S. Application Data

(60) Provisional application No. 62/864,081, filed on Jun. 20, 2019.

(58) Field of Classification Search
CPC ..... A61B 5/6891; A61B 7/003; A61B 5/6892; A61G 2203/30; A61G 2203/32; A61G 2203/34; A61G 2203/36; A61G 2203/44; A61G 7/05; A61G 7/0527; A61J 3/005; A61J 3/071
See application file for complete search history.

(56) References Cited

U.S. PATENT DOCUMENTS

| | | | |
|---|---|---|---|
| 2005/0124864 A1* | 6/2005 | Mack | A61B 5/6892 600/587 |
| 2007/0076935 A1 | 4/2007 | Jeung et al. | |
| 2008/0114260 A1 | 5/2008 | Lange et al. | |
| 2008/0262381 A1 | 10/2008 | Kolen | |
| 2010/0109875 A1 | 5/2010 | Ayon | |
| 2010/0241018 A1 | 9/2010 | Vogel | |
| 2014/0153794 A1 | 6/2014 | Varaklis et al. | |
| 2015/0045608 A1 | 2/2015 | Karp et al. | |
| 2015/0094544 A1 | 4/2015 | Spolin | |
| 2015/0164409 A1 | 6/2015 | Benson | |
| 2015/0208920 A1 | 7/2015 | Ziganshin | |
| 2017/0215772 A1 | 8/2017 | Garn et al. | |
| 2018/0035082 A1 | 2/2018 | Patil | |
| 2019/0133499 A1 | 5/2019 | Auerbach | |
| 2019/0139389 A1 | 5/2019 | White | |
| 2019/0150798 A1 | 5/2019 | Glazer | |
| 2020/0397349 A1 | 12/2020 | Fornell | |

FOREIGN PATENT DOCUMENTS

| | | |
|---|---|---|
| CN | 102164540 | 8/2011 |
| CN | 202568219 | 12/2012 |
| CN | 105025790 | 11/2015 |
| CN | 106170229 | 11/2016 |
| CN | 106456053 | 2/2017 |
| CN | 107874761 | 4/2018 |
| CN | 109380777 | 2/2019 |
| WO | 2019049137 | 3/2019 |

OTHER PUBLICATIONS

Brown, Monitoring Vital Signs with Piezo Film, Medical Design Technology, Mar. 2008, pp. 36-40.
Stanford Children's Health, Breathing Problems, https://www.stanfordchildrens.org/en/topic/default?id=breathing-problems-90-P02666 (printed Nov. 12, 2020).
Piezo Solution for Vital Sign Monitoring, TE Connectivity, https://www.te.com/usa-en/trends/connected-life-health-tech/piezo-solution-for-vital-signs-monitoring.html (printed Nov. 19, 2020).
Search Report, CN 2020800448350, Apr. 18, 2024.

* cited by examiner

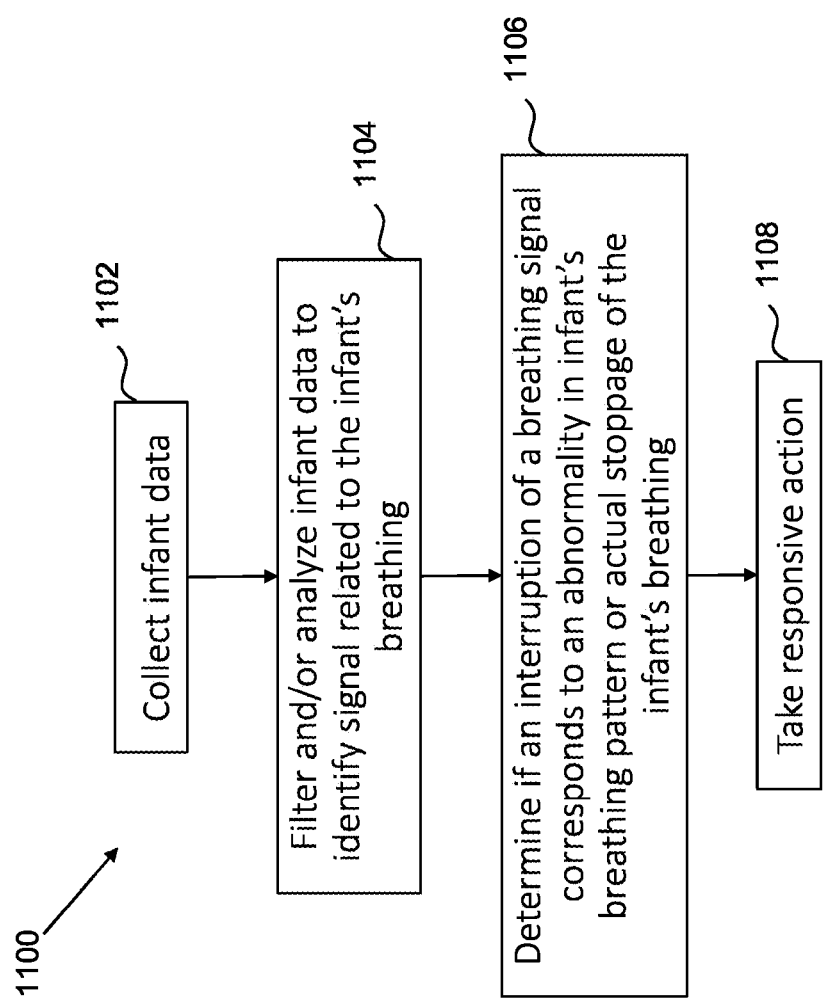

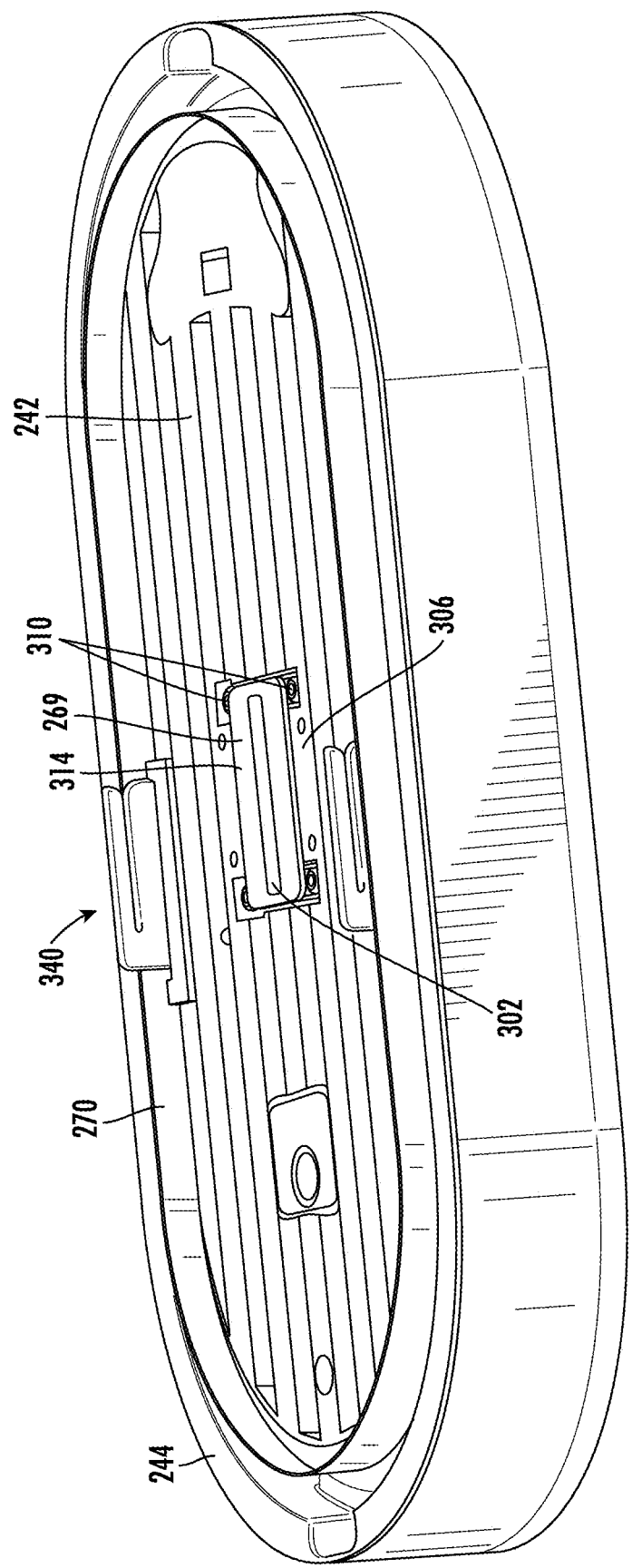

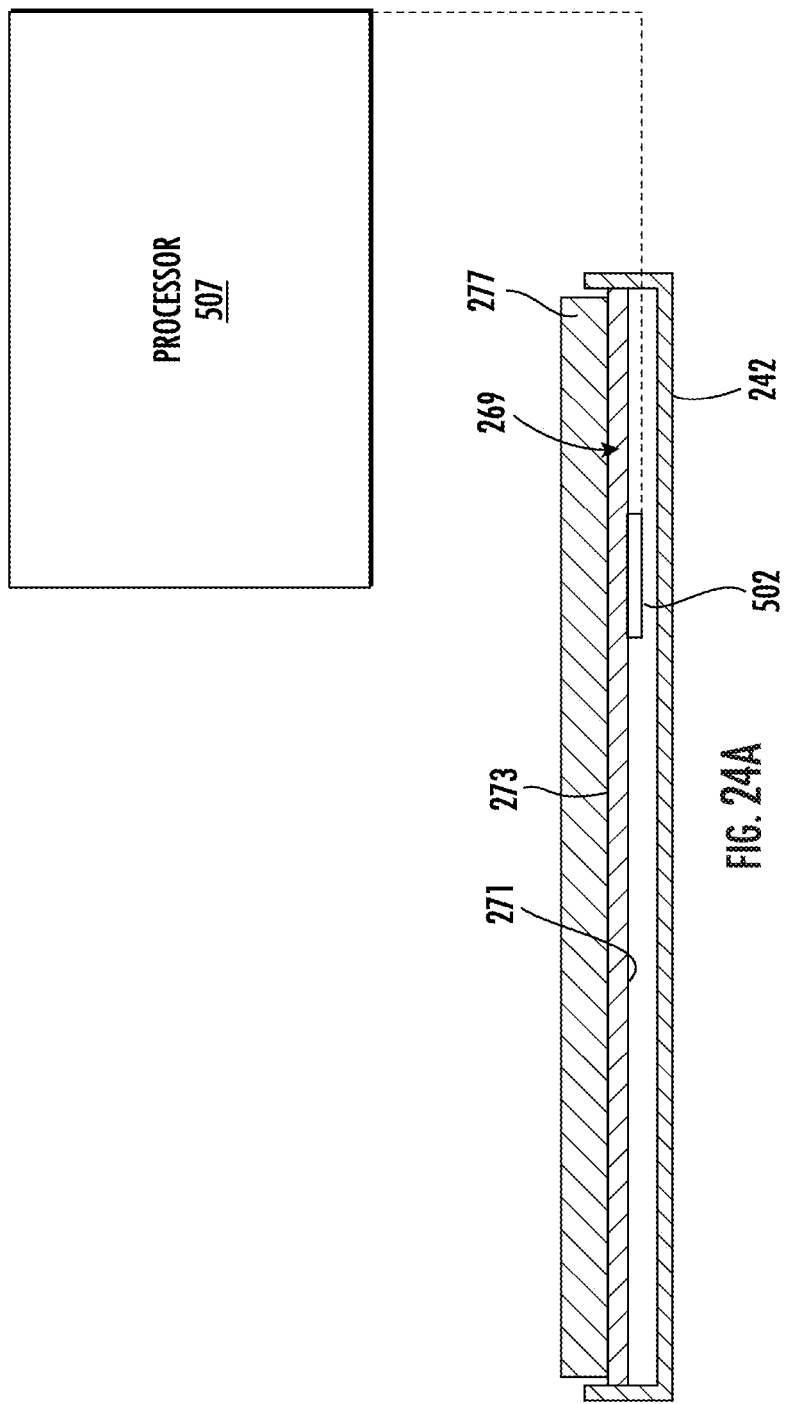

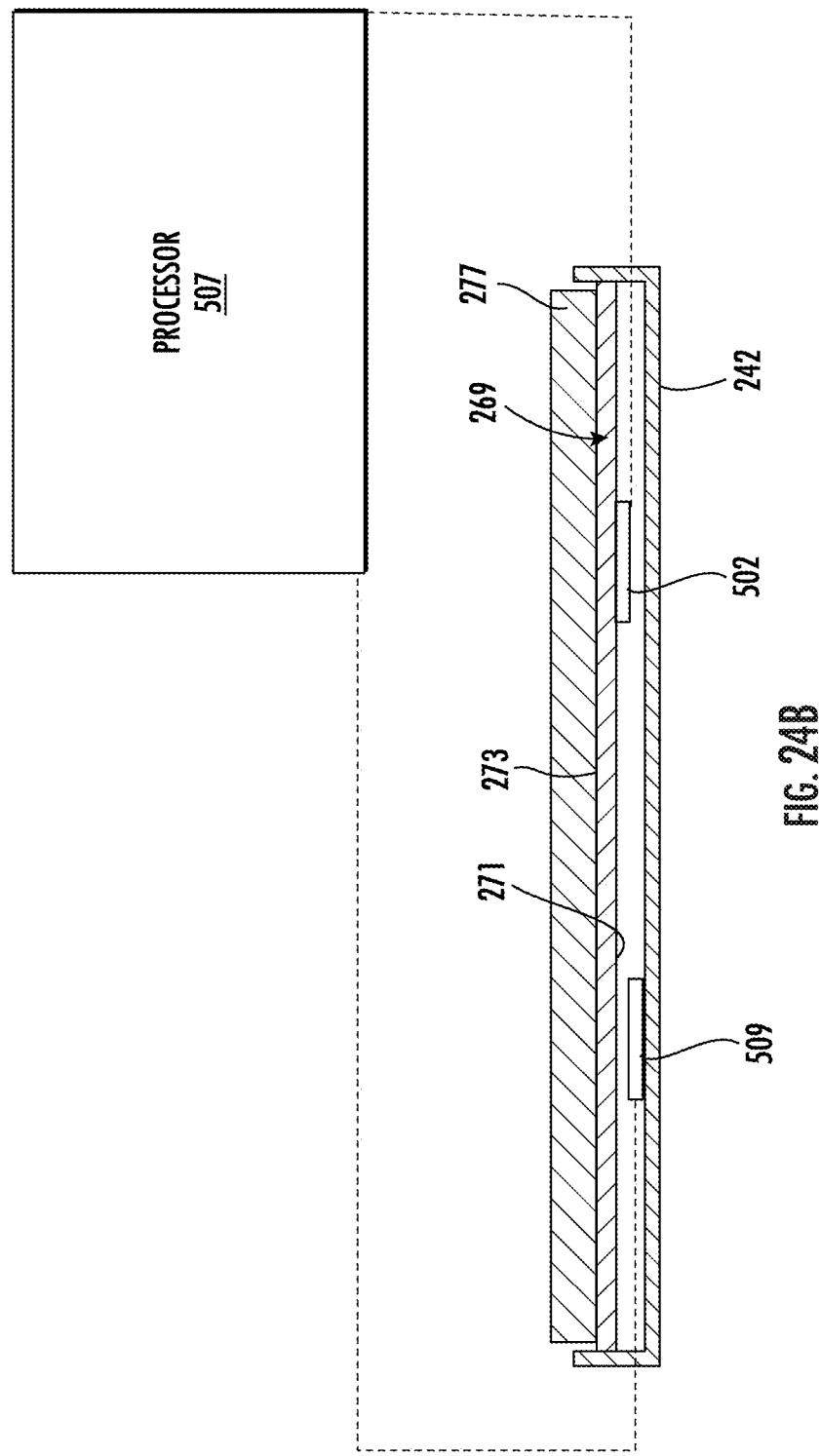

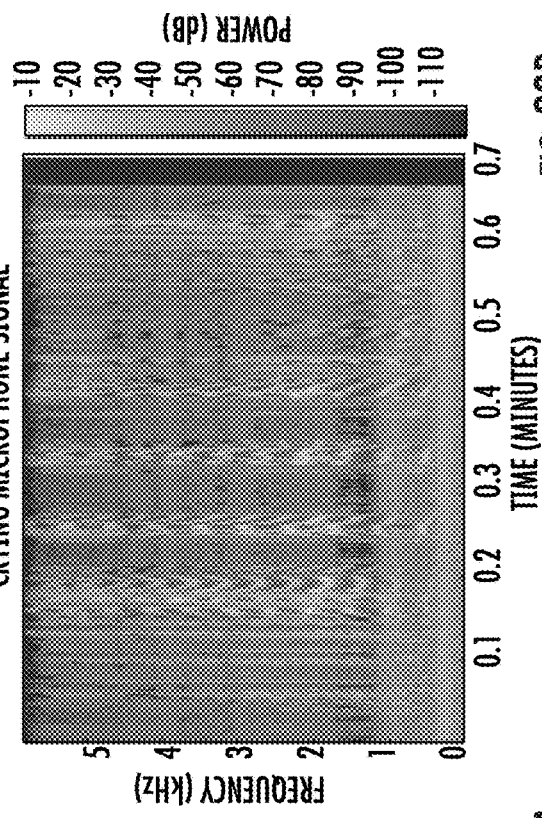
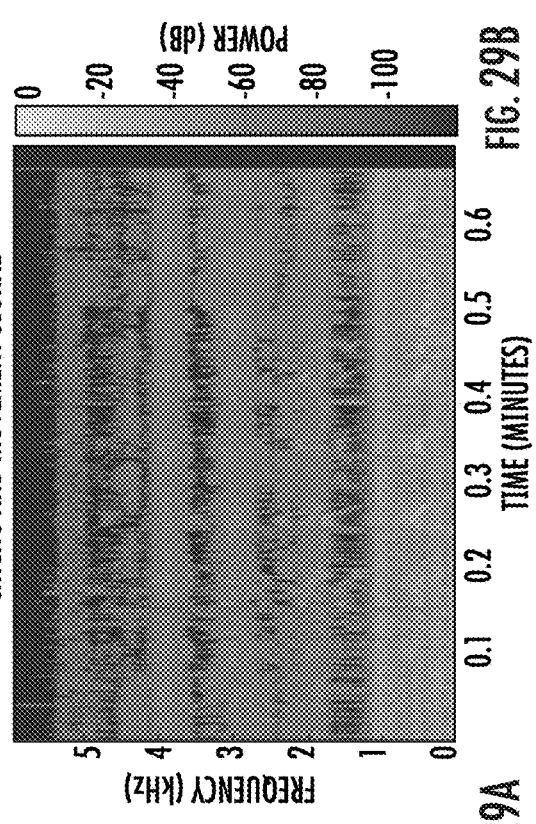
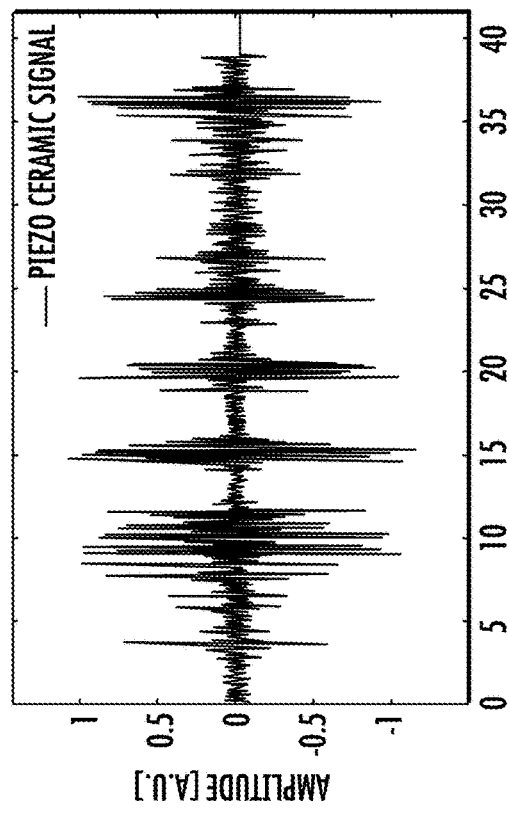
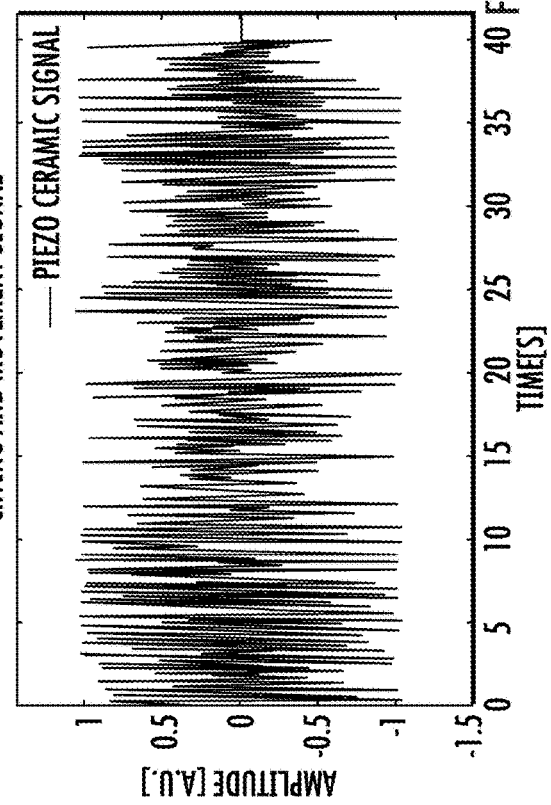
FIG. 28A
FIG. 28B
FIG. 29A
FIG. 29B

SYSTEM AND METHOD FOR MONITORING/DETECTING AND RESPONDING TO INFANT BREATHING

CROSS-REFERENCE TO RELATED APPLICATIONS

The present application is a continuation-in-part of U.S. patent application Ser. No. 16/905,424, filed Jun. 18, 2020, which claims priority to U.S. Provisional Application No. 62/864,081, filed Jun. 20, 2019, the contents of both of which are hereby incorporated herein in their entirety.

TECHNICAL FIELD

This disclosure generally relates to systems and methods for detecting and monitoring breathing, particularly infant breathing. In disclosed embodiments, systems and methods are described for collecting breathing data, filtering said data and responding to changes in or interruption of a breathing signal.

BACKGROUND

Crib death or SIDS (Sudden Infant Death Syndrome) is a leading cause of infant mortality. Approximately 2400 US babies die each year from SIDS during the first year of life. The peak occurrence is from 2-4 months of age, with 80% of the victims being under 4 months and 90% being under 6 months of age.

While the exact cause of SIDS is unknown, the primary cause is believed to be immaturity of the breathing regulatory system in the brain. In essence, it seems that babies "forget" to breath and their internal alarm system does not reliably arouse them to recommence breathing. Once breathing stops, the body becomes more and more hypoxemic and acidotic, leading to a downward spiral of reduced heart rate, dropping blood pressure, cardiovascular collapse and death.

In the hospital setting, the use of an infant monitor immediately alerts the healthcare workers if an infant stops breathing. The health care workers can often resuscitate the infant with simple stimulation (e.g. vigorous jiggling), without the need of oxygen or formal CPR. However, in the home setting where such medical monitoring equipment may be unavailable, the need exists for a way to detect if infant breathing has stopped so that a corrective action can occur before the onset of serious adverse health effects or SIDS. By intervening as soon as possible after an infant's breathing has stopped, it may become possible to reduce the occurrence of SIDS and further lower infant mortality rates.

SUMMARY

In one aspect, a system includes a breath sensor configured to be positioned beneath a subject. The breath sensor may include a vibration substrate; and a piezoceramic element attached to the vibration substrate and configured to detect vibrations propagated along the vibration substrate caused by motion of the subject. In some embodiments, the subject is in vibratory communication with the breath sensor. The vibratory communication may be direct or indirect. For example, a mattress or pad may be positioned between the subject and the breath sensor. In one configuration, vibratory communication includes the subject positioned on a mattress or pad that is positioned on the vibration substrate. The motion may corresponds to at least breathing and heartbeat motion of the subject. The piezoceramic element is positioned along the vibration substrate to transduces the detected vibrations into a signal. The system may also include a breath detection module configured to analyze the signal to identify respiration and heartbeat components within the signal.

In one example, the piezoceramic element is attached to an underside of the vibration substrate.

In the above or another example, the breath detection module is configured to determine from the analysis of the signal if breathing or heartbeat has stopped.

In any of the above or another example, the breath detection module is configured to determine from the analysis of the signal if breathing or heartbeat is normal or abnormal.

In any of the above or another example, the breath detection module is configured to determine from the analysis of the signal frequency and periodicity of breathing or heartbeat.

In any of the above or another example, the breath detection module is configured to determine from the analysis of the signal abnormalities in breathing or heartbeat.

In any of the above or another example, the system further includes a platform upon which the vibration substrate is positioned; and a motor operable to impart motion to the platform. The breath detection module may be configured to determine from the analysis of the signal if breathing or heartbeat has stopped. If the breath detection module detects breathing has stopped, the breath detection module may initiate an action to address the stoppage. In one example, the breath detection module causes the motor to impart the motion to the platform to awake the subject.

In any of the above or another example, the breath detection module is configured to compare the respiration and heartbeat components of the signal to a respective breathing profile and a heart rate profile to determine if the breathing or heartbeat is normal or abnormal.

In any of the above or another example, the system further includes a sound sensor positioned to detect sound within the environment of the breath sensor. The system may further include a cry detection module configured to determine if sounds detected by the sound sensor correspond to a cry of the infant. The cry detection module may be configured to analyze the signal corresponding to the detected vibrations together with the sounds detected by the sound sensor to determine if the detected sounds correspond to a cry of the subject.

In any of the above or another example, the breath detection module is configured to analyze the breathing components to detect respiratory infections.

In any of the above or another example, the breath detection module is configured to analyze the breathing components for early detection of respiratory diseases or conditions In any of the above or another example, the breath detection module is configured to analyze the breathing components for early detection of a cough, cold, croup, asthma, flu, respiratory syncytial virus, or Roseola.

In another aspect, a system includes a breath sensor, a microphone, and a processor. The breath sensor may include a vibration substrate and a piezoceramic element. The vibration substrate may include an expanse of material configured to receive and propagate vibrations caused by motion of a subject positioned on a mattress or pad positioned over the vibration substrate. The piezoceramic element may be attached to the vibration substrate to transduce the vibrations to an electrical signal. The microphone may be positioned to detect sound within the environment of the breath sensor.

The processor may be configured to receive and process the electrical signal transduced by the piezoceramic element to identify subject breathing related data. The processor may be further configured to receive the sound data and compare the sound data to the subject breathing related data to determine if the sound data originating from the subject positioned on the mattress or pad.

In one example, the breath detection module is configured to analyze the breathing components for early detection of respiratory diseases or conditions In the above or another example, the breath detection module may be configured to analyze the breathing components for early detection of a cough, cold, croup, asthma, flu, respiratory syncytial virus, or Roseola.

In yet another aspect, a breath sensor for a sleep device includes a vibration substrate and an piezoceramic element. The vibration substrate may include an expanse of material configured to receive vibrations caused by motion of a subject in vibratory communication with the vibration substrate. In one example, the subject may be in vibratory communication with the vibration substrate when positioned on a mattress or pad resting on or positioned over the vibration substrate. The piezoceramic element may be attached to the vibration substrate to transduce the vibrations to an electrical signal. The processor may be configured to filter the electrical signal and identify components in the signal comprising subject breathing related data and subject heartbeat related data.

In another aspect, a breath detection system includes a processor and memory storing instructions that when executed by the process or cause the system to perform operations including analyzing a signal corresponding to vibrations detected by a piezoelectric sensor having a piezoceramic element attached to a vibratory substrate that is configured to detect vibrations caused by motion of a subject that is positioned over the substrate and directly or indirectly coupled thereto to be in vibratory communication; and identifying respiration, heartbeat, and sound components within the signal.

BRIEF DESCRIPTION OF THE DRAWINGS

For a more complete understanding of the present disclosure and its features and advantages, reference is now made to the following description, taken in conjunction with the accompanying drawings, in which:

FIG. 1B depicts a process for detecting, monitoring, and responding to abnormal or interrupted breathing according to various embodiments described herein;

FIG. 22 is a perspective view of a base and platform of a sleep device including a breath sensor according to various embodiments described herein

FIG. 24A is a cross-section side view of a platform of a sleep device including a vibration substrate including a breath sensor according to various embodiments described herein;

FIG. 24B is a cross-section side view of a further embodiment of a platform of a sleep device including a vibration substrate including a breath sensor according to various embodiments described herein;

FIGS. 28A-28B show a time series of piezoceramic sensor signal collected during a movement and crying event of an subject, where FIG. 28A shows the change in amplitude of the signal, modulated by a low frequency component and high frequency components on top of the signal, and FIG. 28B shows a spectrogram analysis, comparing frequency changes over time; and FIGS. 29A-29B show microphone data collected during the movement and crying event depicted in FIGS. 28A-28B and synchronized in time with that signal, where FIG. 29A is the amplitude over time signal and FIG. 29B is a spectrogram showing only the acoustic vibrations picked up by the microphone, namely high frequency components.

DESCRIPTION

Figure 1A:
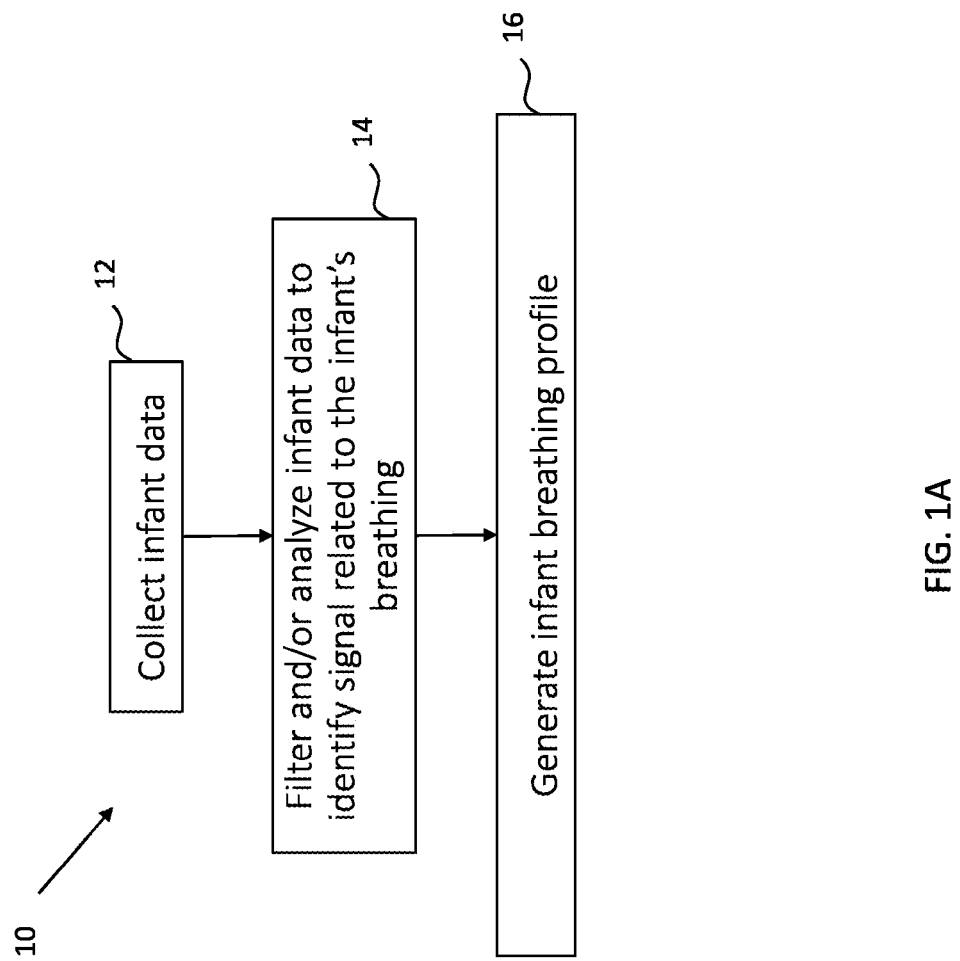
FIG. 1A depicts a process for generating a breathing profile according to various embodiments described herein.

The present application discloses systems and methods for identifying abnormal breathing. The present application also discloses systems and methods of responding to abnormal breath stoppages. The system may find particular use with respect to infants, which may include babies, as well as toddlers. The system may find use with other subjects such as children, adolescents, adults, or elderly. While various embodiments may described herein with respect to infants, it is to be understood that such descriptions may be equally applicable to other subjects as the present disclosure is not limited to infants.

In various embodiments, a breath detection system may be configured to track breathing and respiration patterns and identify abnormal breathing and/or respond to abnormal breath stoppages. The breath detection system may include a sensor device comprising one or more sensors configured to detect breathing. In some embodiments, the breath detection system may include one or more sensors to detect additional physiological parameters of the subject such as weight, heartrate, body temperature, blood pressure, blood oxygen saturation, galvanic skin response, or combination thereof. As described in more detail below, in some embodiments, the breath detection system may include a breath detection module including or in communication with a sensor device including one or more sensors configured to detect breathing. The sensor device may include, for example, motion sensors such as optical, video, IR, vibration, piezoelectric, weight, or accelerometer sensors. Additionally or alternatively, the sensor device may include sound sensors such as microphones. Sensors of the sensor device described herein as detecting breathing related data may also be referred to herein as breath sensors. As noted above, the breath detection system may monitor other physiological parameters, which in some instance may be detected using the same sensors as used to collect breathing data. Thus, in some instances, the breath detection system may utilize breath sensors to detect non-breathing related data corresponding to various other physiological parameters in addition to breathing related data In one example, identification of abnormal breathing may include detecting subject data such as movement and/or sound data related to breathing. The subject data may be analyzed by the breath detection system to identify breathing patterns. Breathing/respiration patterns may be compared to breathing profiles to identify abnormal deviations from the breathing profile. In some embodiments, breathing profiles may be individualized to a particular infant, generic, or may be selected based on characteristics of a subject, which may be input by a user or detected and/or measured by the breath detection system. For example, the breath detection system may include or access multiple breathing profiles that may be selected by the system based on an input age, weight, e.g., birth weight or current weight, sex, medical condition, or other data associated with the infant. Such analysis may utilize AI or machine learning to detect corollary factors. In an embodiment, the breath detection system may alternatively or additionally build and/or individualize a breathing profile from a generic or selected initial breathing profile during a subject's use of the system. An initial breathing profile may be more specific or determined to be more applicable to the subject based on input, known, or detected data corresponding to the subject. For example, age, sex, medical conditions, or weight, e.g., for and infant or child birth weight or current weight, may be used to select a more specific initial breathing profile. The system may measure and analyze breathing patterns of the subject and thereafter continuously or periodically update the general, initial, or individualized breathing profile to individualize or further individualize the profile to the subject as for some subjects, particularly infant subjects, it may be normal to have longer breathing pauses than indicative of the population norm and, for some, a breathing pause within the normal respiration range may be an abnormal event. For diagnostics, a breathing pattern may be established to detect changes in breathing. Such change may be indicative of low oxygenation levels. The breathing cadence may also be enhanced with higher frequency information, such as wheezing, grunting or stridor for early detection of a condition or distress. Such information can be obtained from one or more sensing devices configured to detect breathing related data, which may include a breath sensor as described herein, such as a piezo electric vibration sensor and/or microphones.

Upon determination that abnormal breathing has occurred, which may include cessation of breathing, the breath detection system may be configured to generate a response signal. The response signal may initiate an alarm or call to a caregiver, a sound, motion of a movement platform of a bassinet, or other action.

FIG. 1A illustrates a process 10 for generating an infant breathing profile according to various embodiments. As noted above, the process 10 is not limited to infants and may be applied similarly to other subjects. In some embodiments, the systems or devices, such as the breath detection system, breath detection module, control system, or processing system, described herein, may be configured to execute process 10.

In process 10, step 12 comprises collecting infant data related to the breathing of an infant. In one example, collecting infant data includes collecting motion data related to infant breathing. In one example, collecting infant data includes collecting sound data related to infant breathing. In one example, collecting infant data includes collecting sound data and motion data related to infant breathing. In some embodiments, collecting motion data related to infant breathing, collecting sound data related to infant breathing, or both includes utilizing multiple types or sources of such data for creation of a robust input. For example, a sensor device, which may include multiple sensor devices and/or types of sensors, e.g., motion, sound, or combinations thereof, may be positioned around an infant to collect infant data, which may include sensors positioned at different locations to collect infant data. Sensors may be positioned on, around, or integrated with a crib, bassinet, swaddle device, chair, or other devices In some embodiments, collecting infant data in step 12 includes collecting a larger set of infant data that includes a subset of infant data related to breathing of the infant. For example, collecting infant data may include collecting motion data associated with motion unrelated to breathing such as non-breathing related infant movement, heartbeat/ heartrate, and/or other motion occurring within a surrounding environment of the infant, e.g., movement related to a moving platform, garments, mobile, bed clothes, curtains, caregivers, etc. As another or further example, collecting infant data may include collecting sound data that includes sounds unrelated to infant breathing such as non-breathing related infant sounds, e.g., crying, speaking, laughing, or environmental sounds, e.g., music, talking, sounds resulting from infant or caregiver contact with environment, machinery or device noises, or other ambient noises. In some such embodiments, collecting infant data includes collecting multiple sets of data that each include a subset of infant breathing related data. This may occur due to motion and/or sound sensors detecting motions and/or sounds unrelated to breathing, which, for the purpose of isolating breathing related data, may be considered noise.

In step 14 of process 10, the collected infant data may be filtered to remove non-breathing related data and/or analyzed to identify a signal related to infant breathing. In an embodiment wherein collected infant data includes non-breathing related data, the collected infant data may be analyzed and filtered to remove non-infant breathing related data for further filtering and/or analysis of the collected infant breathing related data. For example, further to the above, portions of the collected data corresponding to non-breathing related movements of the infant may be filtered out of the collected infant breathing data, such as movement of a sleep surface, shifting of the infant during sleep, movement of fabrics or other items such as stuffed animals or a caregiver's hand near the infant, etc. to isolate the breathing related data. Filtering may include application of bandpass filters, for example.

In some embodiments, step 14 may also include processing and/or converting the collected infant data, which may include infant breathing related data filtered from non-breathing related data or both, into a frequency domain. In one example, a frequency domain may be utilized as part of a filtering analysis for separation, identification, or isolation of infant breathing related data. As described in more detail herein, infant data may be collected via a sensor device comprising one or more sensors. The sensor device may include one or more sensors, such as one or more motion sensors such as optical, video, IR, vibration, piezoelectric, weight, gyroscope, or accelerometer sensors and/or sound sensors such as microphones. It will be appreciated that the sensor device may include various sensors that may or may not associate or communicate with each other. For example, the sensor device may include multiple separate sensors that collect data independent of each other. Thus, the sensor device may include multiple separate sensors or sensor devices that collect infant data. In an embodiment, the sensor device includes a motion sensor comprising a video sensor. The video sensor may collect a video signal from which motion may be analyzed. For example, a video signal of the infant's breathing may be analyzed by a processing algorithm to detect a rate of breathing, and which may output data comprising a frequency of respiration, such as in Hertz. The frequency may be an averaged value or may be updated on a continuous basis or on a desired interval basis.

In some embodiments, analysis and/or filtering at step 14, may include conversion to a frequency domain utilizing raw sensor data before filtering. In such an embodiment, one or more frequencies may be identified by a data processor in a particular set of collected sensor data of the collected infant data. A data processor, which may include a plurality of local or distributed data processors, may be local or remote with respect to the infant, device in which the infant is monitored, and/or the surrounding environment in which the infant is monitored. For example, the data processor may comprise a remote resource, such as an application running on a remote server(s) or a cloud resource that receives sensor data for further processing. The data processor may be associated with the breath detection system, breath detection module, control system, or processing system for example. In an embodiment, the data processor may convert incoming sensor data into a plurality of frequency signals. The plurality of frequency signals may then undergo a filtering process to isolate a frequency signal related to an infant's breathing. In an embodiment, identified frequency signals above 10 Hz may be filtered out. In an embodiment, a known or inferred frequency signal attributable to a moveable infant-supporting sleep platform may be filtered out of the plurality of identified frequencies. In embodiments, other frequency signals determined to be unrelated to infant breathing may be filtered out or otherwise attenuated from the frequency domain data.

At step 16 of process 10, the collected breathing related data may be utilized to generate or enhance an individualized infant breathing profile from which abnormal breathing or patterns thereof may be subsequently analyzed. The infant breathing profile may be generated from the filtered infant data including the infant breathing related data. In an embodiment, the frequency of breathing and patterns thereof, which may include the frequency domain data, may be used to generate the infant breathing profile. The infant breathing profile may be individualized to an infant by performing step 12 with the infant breathing related data. The profile may be static or dynamic, e.g., updated over time based on additional infant breathing related data or input characteristics. As breathing patterns, e.g., frequency and/or amplitude, may be variable both within a set period of time as well as over time, step 16 may include updating the profile based on additional infant data obtained in step 14. The additional infant data may be breathing related data or non-breathing related data, which may include non-sensor data input, e.g., input by a caregiver or other user. In one example, a frequency signal may be analyzed for variation as more infant data is collected in step 14 and a variable breathing pattern may be established with respect to the variation analysis. Thus, a frequency signal corresponding to an infant's breathing may not comprise a single frequency, but may comprise a range of frequencies, or may comprise an approximate frequency with allowance for variability within a determined tolerance, or may periodically or consistently update to a new adapted value as more infant breathing related data is collected and analyzed in steps 14 and 16. In this way, step 16 may establish an individualized infant breathing profile, which may be unique for a given infant, and which takes into account natural variation in breathing over time. In at least one embodiment, breathing related data is additionally or alternatively analyzed and filtered with respect to amplitude of breathing to identify patterns with respect to depth of breathing, e.g., duration or depth of inhalation and/or exhalation, in a manner similar to that described herein with respect to frequency. In one example, the process may include generating an infant breathing profile that includes amplitude patterns together with or separate of frequency patterns.

FIG. 1B illustrates a process 1100 for detecting and monitoring infant breathing and responding to abnormal or interrupted breathing according to various embodiments. As previously noted, the process 1100 may be equality applicable to other subjects. In some embodiments, the systems or devices, such as the breath detection system, breath detection module, control system, or processing systems, described herein, may be configured to execute process 1100. At step 1102 infant data related to the breathing of an infant is collected or otherwise obtained. Collecting infant data with respect to step 1102 may be similar to that described with respect to step 12 of process 10 shown in FIG. 1A. In one example, collecting infant data 1102 includes collecting motion data related to infant breathing. In one example, collecting infant data 1102 includes collecting sound data related to infant breathing. In one example, collecting infant data 1102 includes collecting sound data and motion data related to infant breathing.

In step 1104 of process 1100, the collected infant breathing related data is filtered and/or analyzed to identify a signal related to the infant's breathing. In an embodiment, the collected infant data may be filtered to remove non-infant breath related data as described above with respect to step 14 of process 10 (FIG. 1A). For example, portions of the collected infant data that correspond to movement and/or sound that is not related to infant breathing may be filtered out or attenuated from the collected breathing related data, such as movement or sound related to movement of a sleep surface, shifting of the infant during sleep, movement of fabrics or other items such as stuffed animals or a caregiver's hand near the infant.

Additionally, in step 1104, the collected infant data may be processed and/or converted into a frequency domain, which may be in a manner similar to that described above with respect to step 14 of process 10 (FIG. 1A). Collecting infant data 1102 may include collecting data detected by a sensor device, which may be a sensor device as described elsewhere herein. For instance the sensor device may comprise a motion sensor. The motion sensor, for example, may be combined with a video imaging sensor configured to capture video images of the infant and provide a video signal corresponding to, or from which, infant breathing related data may be obtained. In one example, a video signal of the infant's breathing may be analyzed by a processing algorithm to detect a rate of breathing, and which may output data comprising a frequency of respiration, such as in Hertz. The frequency may be an averaged value or may be updated on a continuous basis or on a desired interval basis. As introduced above and described in more detail below, the sensor device may comprise one or more sound sensors in addition to or instead of one or more motion sensors. Other types of sensor may also be used.

In one embodiment, conversion to a frequency domain under step 1104 may be performed on raw sensor data before filtering. In such an embodiment, one or more frequencies may be identified by a data processor, which may be part of or in communication with the breath detection system, breath detection module, control system, or processing systems described herein, in a particular set of collected sensor data. In an embodiment, a data processor may convert incoming sensor data into a plurality of frequency signals. The plurality of frequency signals may then undergo a filtering process to isolate a frequency signal related to an infant's breathing. In an embodiment, identified frequency signals above 10 Hz may be filtered out. In one embodiment, a known or inferred frequency signal attributable to a moveable infant-supporting sleep platform may be filtered out of the plurality of identified frequencies. In a further or another embodiment, other frequency signals determined to be unrelated to infant breathing may be filtered out of the frequency domain data, which may correspond to breathing related data.

In an embodiment, step 1104 may further comprise accounting for an irregularity in breathing over time. For example, a frequency signal may be analyzed for variation as more data is collected, and a variable breathing pattern may be established. Thus, a frequency signal corresponding to an infant's breathing may not comprise a single frequency, but may comprise a range of frequencies, or may comprise an approximate frequency with allowance for variability within a determined tolerance, or may periodically or consistently update to a new adapted value as more breathing related data is collected and analyzed. In this way, step 1104 may establish an infant breathing profile, which may be unique, e.g., individualized, for a given infant, and which takes into account natural variation in breathing over time, which may be similar to that described with respect to process 10. Thus, collected breathing related data may be utilized to generate an individualized infant breathing profile from which abnormal breathing or patterns thereof may be subsequently determined. In some embodiments, process 10 runs behind process 1100 or process 1100 incorporates process 10. The infant breathing profile may be established utilizing process 10, described above with respect to FIG. 1A. In various embodiments, a general infant breathing profile typical to an infant may be used rather than an individualized profile, such as described herein and with respect to FIG. 1A. In some embodiments, multiple general infant breathing profiles may be used or available for selection by the system to provide a breathing profile more applicable to the particular infant by using a profile known to be more representative of subjects sharing characteristics with the infant such as age, sex, weight, temperament, medical conditions, or the like. In one example, the selection of a general infant breathing profile may correspond, at least in part, to an infant age, while other profiles may be age neutral. In some examples, selection variables that may be used to specify a general infant breathing profile may include one or more of sex of infant, age of infant, time of day, duration of sleep, medical data such as gestational age at birth or known medical conditions, or other variables. In one embodiment, process 1100 generates an individualized breathing profile from an initial general profile by incorporation of collected breathing related data into the profile.

At step 1106 of process 1100, the frequency signal corresponding to the infant breathing may be monitored to detect for an interruption, abnormality, or stoppage in the signal. In an embodiment, step 1106 may determine if the interruption of a breathing signal corresponds to an actual stoppage of the infant's breathing. For example, in the event that an interruption in a breathing signal has been detected, step 1106, in an embodiment, may determine whether the interruption is due to the infant being removed from a sleeping surface by a caregiver, if the infant has moved out of the range or boundary of a data collection sensor(s), or if some physical object is obstructing the ability of the sensor device to collect breathing related data. Such events may be detected by identifying a radical change in observed frequencies. A radical change may be identified based on an amount of increase or decrease in frequency and may represent a predefined threshold triggering a trigger event. In one example, the amount may be determined over a period of time prior to variability and a period of time during variability. The amount may be a percentage or whole number, for example. In some embodiments, a measured change in frequency determined to be a radical change may be based on a predetermined variation in frequency, a general or individualized infant breathing profile, or combination thereof. In various embodiments, step 1106 may additionally comprise monitoring for an abnormality in collected breathing related data. An abnormality may comprise a sudden or gradual deviation of an infant's breathing from an infant breathing profile. Such a deviation may be indicative of the infant experiencing trouble breathing, possibly due to an airway obstruction or from having moved into a compromising orientation while sleeping. Furthermore, an abnormality in a breathing related signal may comprise a prolonged elevated frequency of breathing, which may correspond to a distressed state which may be detected in step 1106. In addition, if an abnormality in breathing frequency has been detected, step 1106 may comprise monitoring the abnormality for a given period of time, either predetermined or based on an infant's unique breathing profile.

In some embodiments, an infant breathing profile may be established, which may be on-going, in step 1104 and 1106, concurrent with monitoring for abnormalities in breathing monitored patterns. For example, a general infant breathing profile may comprise an initial infant breathing profile that may be used for a pre-determined period of time or otherwise until a sufficient individualized infant breathing profile is generated. In some embodiments, the breath detection system may build on or modify an initial infant breathing profile utilizing the breathing related data to generate an individualized infant breathing profile or may replace the initial infant breathing profile with an individualized infant breathing profile generated from analysis of collected breathing related data applied to an infant breathing profile template.

An infant breathing profile may include a set of predefined threshold trigger events that represent deviations for normal infant breathing. When a trigger event is detected, action may be taken as described below with respect to step 1108. Some subjects under normal breathing may take shorter or longer pauses between breaths than others. Thus, in an embodiment, step 1106 may include monitoring and accounting for learned or programmed infant behaviors to sort between actual breathing abnormalities and normal, characteristic behaviors, which may be represented in the breathing profile of the infant. As more infant data is collected and analyzed, breathing patterns specific to the infant may be used to modify the infant breathing profile and/or allow deviation from or modification of one or more trigger event threshold settings thereof. For example, a threshold for a trigger event may be increased or decreased based on collected breathing related data. Thus, overtime, infant breathing profiles may individualize and/or change and adapt to the infant. Such changes may include modification of thresholds with respect to trigger events or removal of trigger events. Individualized infant breathing profiles, for example, may include trigger events having thresholds based on the individualized infant breathing profile generated from the infant breathing related data.

If an interruption or prolonged abnormality of a breathing related signal is determined to have occurred, and step 1106 further determines that the interruption of the signal corresponds to an actual stoppage or interruption in an infant's breathing profile, an appropriate responsive action is performed. As noted above, the determination may be based on analysis, e.g., comparative analysis, of collected infant data or data derived therefrom, e.g., raw or filtered infant motion data, infant sound data, breathing related data, frequency domain data, or combination thereof, with respect to the infant breathing profile, whether individualized or general, including measured deviations from the profile. For example, time between one or a predetermined number of breaths or within a time period may be measured and compared to the infant breathing profile.

Deviations from the profile may be compared to threshold settings to determine if a trigger event has occurred requiring action at step 1108. The determination may be based on a percentage deviation between breaths or frequency of breaths, a predefined time period between one or more breaths, or a frequency pattern having breathing intervals otherwise found to be sufficiently abnormal to represent a trigger event. In an embodiment, step 1108 may comprise sending an alert to a caregiver or to an emergency services provider. In some embodiments, the alert may comprise a text message, SMS, push notification, etc. In one embodiment, the process may integrate with and/or communicate with health care/hospital monitoring systems. For example, the system may provide raw or processed data, notifications, and/or alerts to third party systems. The system may also integrate with third party systems. In an embodiment, step 1108 may further comprise sending a signal to a moveable infant sleep platform to activate a stimulating mode of operation intended to wake the infant and resume normal breathing.

As introduced above, in some embodiments, the breath detection system may be configured to detect heartbeat and/or heartrate of an infant, which may also be referred to as heartbeat herein, which may be separate or in addition to detection of breathing. One or more sensors of the sensor device may collect infant data comprising motion or sound, such as vibration. The infant data collected with respect to heartbeat detection may include the same or different motion and/or sound data used for breathing detection. In various embodiments, the heartbeat related data comprises motion and/or sound data detected by one or more sensors. The infant data may be analyzed to identify heartbeat characteristics or patterns such as heartrate, strength of heartbeat, and patterns thereof. Heartbeat patterns may be compared to heartbeat profiles to identify abnormal deviations from a heartbeat profile. In some embodiments, heartbeat profiles may be individualized to a particular infant, generic, or may be selected based on characteristics of an infant, which may be input by a user or detected and/or measured by the breath detection system. In one example, the breath detection system may include multiple heartbeat profiles that may be selected by a user or by the system based on an input age, weight, e.g., birth weight or current weight, sex, medical condition, or other data associated with the infant. In an embodiment, the breath detection system may individualize a heartbeat profile from a generic or selected beat profile during an infant's use of the system. For example, the system may measure and analyze heartbeat patterns and update a heartbeat profile to individualize an initial heartbeat profile. Upon determination that abnormal heartbeat has occurred, which may include cessation of heartbeat, a faint heartbeat, or heart arrhythmia, for example, the breath detection system may be configured to generate a response signal. The response signal may initiate an alarm or call to a caregiver, a sound and/or motion of a movement platform of a bassinet to stimulate the infant, or other action.

A process of heartbeat detection may be similar to that described above with respect to breathing detection in FIG. 1A wherein infant data is collected, filtered to identify heartbeat related data, and analyzed to generate a heartbeat profile. Heartbeat detection may include collection and analysis of infant data for determination and response to abnormal heartbeat rate in a manner similar to that described with respect to breathing detection in FIG. 1B.

The systems or devices, such as the breath detection system, breath detection module, control system, processing systems, or sensing device, described herein, may utilize sensed data from two or more sensors and/or sensor types to generate three-dimensional models of the infant and surroundings. For example, data collected by sensors positioned at different locations capturing data of the same environment may be compared to identify differences in object locations and/or size and these perspective differences, such as stereo or linear, may be used to create a three-dimensional model or understanding of the environment.

As introduced above, in certain embodiments for detecting a subject's breathing disclosed herein, such as collecting subject data in step 12 of process 10 and step 1102 of process 1100, a sensing device is provided in order to collect infant data related to breathing. As also noted above, the subject data may include non-breathing related data, which, in various embodiments, may be filtered to identify or isolate the breathing related data. In some embodiments, the sensing device comprises one or more video, ultrasonic, radar (mmWave, UWB, LIDAR and such), thermal imaging, microphone, piezoelectric sensors, or other sensors to detect motion, sound, and/or physiological parameters as described herein. For example, as also indicated above, the sensing device may include biometric sensors that may detect physiological parameters, such as breathing and/or non-breathing related data, such as heartbeat characteristics, heartrate, body temperature, body temperature, blood pressure, blood oxygen saturation, galvanic skin response, or combination thereof. As such, the sensing device may be provided in order to collect subject data related to heartbeat. Subject data related to heartbeat and/or other physiological parameters/non-breathing related biometric data may be collected by the same and/or different sensors provided to collect breathing related data. The subject data may include non-heartbeat related data, which, in various embodiments, may be filtered to identify or isolate the heartbeat related data.

In embodiments disclosed herein, various methods and devices are disclosed for collecting subject data. In one embodiment, the sensing device may comprise one or more sound sensors. A sound sensor, for example, may comprise one or more microphones or other device for detecting sound vibrations, such as a piezoelectric sensor. A sound sensor may be positioned at one or more appropriate locations relative to and within an appropriate distance from a subject. Sound sensors may be located on or around an sleep device such as a bed, crib, bassinet, or hospital bed. In one example, one or more sound sensors may be placed underneath the back of the subject. Sound sensors may be embedded in a mat, mattress, platform upon which an subject is supported, sleep garment, or infant sleep sack. For example, one or more sound sensors may be located underneath the back of the subject and embedded in a mat, mattress, pad, or sleep garment, such as an infant sleep sack. Sound sensors may be located beneath a platform upon which a subject is to be positioned.

In various embodiments, the sensing device comprises one or more motion sensors configured to collect motion data. Motion sensors may be used as biometric sensors, such as breath sensors, heartbeat sensors, temperature sensors, or other sensor to detect physiological parameters. In some embodiments, one or more motion sensors comprise one or more optical, imaging, and/or light/electromagnetic wave or field sensors. For example, a motion sensor may include one or more motion sensors utilizing radar, laser, or video imaging, motion sensors. Thus, some motion sensors may include electromagnetic wave transmitters in addition to electromagnetic wave receivers or detect apparatus. In one embodiment, the sensing device comprises a motion sensor comprising a capacitance sensor. In any of the above or another embodiment, the sensing device may include a motion sensor configured to detect vibrations, force, pressure, strain, acceleration, angular velocity, or combination thereof. For example, a motion sensor may comprise one or more of an accelerometer, gyroscope, or piezoelectric sensor. Sound sensors may detect sound or vibrations associated with subject breathing. In one embodiment, a motion sensor comprises a sound sensor configured to detect motion, such as a sensor configured to detect movement utilizing echo-location, such as with an ultrasonic sensor comprising an ultrasonic transmitter and receiver. In some embodiments, a motion sensor comprises a proximity sensor utilized to measure motion by changes in proximity over time. Example proximity sensors may include combination transmitters and receivers, sound sensors, electromagnetic sensors, capacitance sensors, or combinations thereof.

In an embodiment, the sensing device comprises a motion and/or sound sensor. In one example, the sensing device comprises sensors for detecting vibrations. One or more sensors of the sensing device may be positioned underneath an subject, such as above or below a mattress or pad. In some embodiments, sensors may be integrated with a mattress or pad. In one embodiment, sensors may be integrated with a platform structure upon which a subject is to be placed. The motion or vibration data may comprise measurements of relative movement of the subject's back. The sensor may be attached to a platform structure directly or indirectly, e.g., positioned within a housing attached to or positioned to receive vibrations propagated along the platform. The platform structure may be constructed of a material having measurable flex and/or vibration responsive materials or otherwise materials along which vibrations may propagate for detection by the vibration sensor. Example platform structures may include metals, alloys, plastics, or the like.

In an embodiment, the sensing device may comprise a sound sensor, such as one or more microphones or piezoelectric sensors. Sound sensors may be used as biometric sensors, such as breath sensors, heartbeat sensors, or other sensor to detect physiological parameters. Sound sensors may detect audio waves or propagation of vibrations, pressure changes, or waves through a medium. The breathing and/or heartrate information may be measured in the audible spectrum.

In various embodiments, the sensing device comprises or is configured to communicate, e.g., transmit sensed data, with a processor coupled with a storage medium storing instructions executable by the processor to analyze the detected or measured data obtained by the sensing device. As noted above, the processor or plurality of processors may be local, remote, and/or distributed with respect to the subject, device in which the subject is monitored, and/or the surrounding environment in which the subject is monitored. Thus, the sensing device, or one or more sensors thereof, may include a transmitter, receiver, or transceiver configured for communication with the processor. The processor may operatively couple to a transmitter, receiver, or transceiver configured for communication with the sensing device. Communication may be by wired or wireless communication protocols. It will be appreciated that the sensing device may include multiple types of sensors. For example, multiple types of sensors may be used to collect breathing related data wherein their outputs are compared or utilized together to determine a breathing status and/or profile of the subject. Same or different sensors may be used to collect heartbeat related data wherein their outputs are compared or utilized together to determine a heartbeat status and/or profile of the subject.

As introduced above, the sensing device may include one or more motion sensors. Motion sensors may be used as biometric sensors, such as breath sensors or other sensor to detect physiological parameters. The one or more motion sensors may be configured to measure relative motion of a chest of a subject, such as an infant, and/or stomach area in variable sleep positions with good resolutions. The relative movement of the chest and/or stomach area may be defined as relative motion of a body part of the subject with respect to a reference point. The body part may comprise the chest, stomach, or other such body part of which movement may be indicative of breathing. The reference point may include one or more fixed reference points, such as one or more points associated with portions of an subject, such as a back of the subject, a mattress of a bassinet or bed where an subject is positioned, a platform on which the subject is placed, a garment worn by an subject, or location around the subject. Alternatively or additionally, a reference point may include one or more moving reference points. For example, the subject may be positioned on a moving platform, e.g., an infant subject within a bassinet having a platform configured to rotate, rock, or otherwise undergo movement. A moving reference point may move in a manner coinciding with overall motion of the subject. Relative movement may be measured relative to one or more fixed reference points, moving reference points, or combination thereof. In various embodiments, movement relative to a reference point not attributable to movement of the chest and/or stomach area of the subject associated with breathing may be filtered. For example, motion data comprising measured relative motion with respect to one or more reference points may be processed to isolate breathing related data from a broader set of the motion data that includes non-breathing data. Motion data may also include vibration data or motion data related to heartbeat that may be filtered to identify heartbeat related data, such as heartrate.

In various embodiments, one or more motion sensors are configured to independently or in one or more combinations detect relative movement to a resolution of at least 1 mm of relative motion resolution. As noted above, analysis of the data to achieve the desired resolution may be performed by a processor, which may be part of or in communication with the breath detection system, breath detection module, control system, or processing systems described herein, utilizing computer readable instructions such as software, firmware, or the like. In an embodiment, 1 mm of relative motion resolution means that a sensing device may be able to detect differences in relative or absolute position of objects, including the subject's chest or stomach area, which are at least 1 mm in magnitude. Other embodiments may be able to detect positional differences less than 1 mm in magnitude.

In some embodiments, the sensing device comprises one or more motion sensors comprising one or more video imaging sensors. Video imaging sensors may be used as biometric sensors, such as breath sensors, heartbeat sensors, temperature sensors, or other sensor to detect physiological parameters. Video imaging sensors may include or incorporate one or more subject imaging cameras for detecting motion within desired resolutions, e.g., at least 1 mm. A video imaging sensor may include or communicate with a processor and/or storage medium storing instructions executable by the processor for detection of motion from images obtained by the sensor. In some embodiments, a video imaging sensor includes one or more cameras configured to detect wavelengths within and/or outside the visible spectrum, such as infrared wavelengths. The one or more motion sensors may be disposed in an appropriate location relative to and within an appropriate distance from the subject such that it is able to capture images of an subject with sufficient resolution when the subject is inside a bassinet or other sleeping surface. Some embodiments may include one or more subject imaging cameras disposed around a bassinet, e.g., above and/or along one or more sides, and oriented to image an infant laying within the bassinet. Furthermore, subject imaging cameras may be standard/visible light, infrared, or otherwise such that they are able to capture images of a subject in variable lighting conditions.

In some embodiments, the sensor device comprises one or more motion sensors comprising one or more radar devices, which may also be referred to as radar sensors. Radar devices may incorporate various radar technologies such as mmWave, UWB or LIDAR. Radar devices may include or communicate with a processor and/or storage medium storing instructions executable by the processor for detection of motion from radio or other electromagnetic waves collected by the sensor. In an example, a radar device may be placed approximately within an underside of a subject supporting platform and oriented such that it is able to capture the relative motion of a subject's bloodstream, heart, chest and/or stomach area when the subject is inside a bassinet including a supporting platform. Some embodiments may have one or more radar motion sensors disposed around the sides of a bassinet or directly above a bassinet and oriented to measure relative motion of subject's chest and/or stomach area. Radar devices may include or detect one or more markers, which may comprise reference points in some embodiments. For example, a marker may be associated with a front of a chest or stomach area of the subject. In a further example, a second marker may be associated with a back of the subject. In one example, a third or a second marker may be associated with another location that moves with the subject, such as a moving platform, from which overall movement of the subject relative to an observational reference frame may be subtracted. In some embodiments, a receiver of a radar sensor may be positioned for movement corresponding to that of the subject in the observational reference frame. For example, the receiver may be positioned on a moving platform upon which the subject is positioned and subject to movement. Markers may similarly be utilized with other motion sensors, such as video imaging sensors.

In one embodiment, the sensing device includes one or more motion sensors comprising one or more piezoelectric sensors. Piezoelectric sensors may be configured to detect pressure, force, or acceleration changes, which may include vibrations. Piezoelectric sensors may detect propagation of sound waves through solid or gas resulting sensor vibrations transduced to a heartbeat detection module and/or breathing detection module. Piezoelectric sensors may include or communicate with a processor and/or storage medium storing analysis instructions executable by the processor for analysis of current generated by the sensor. In one example, a biometric sensor includes a ceramic piezoelectric sensor. The ceramic piezoelectric sensor may be configured to detect vibrations associated with movement of a subject and/or sound causing vibrations along a material structure along which the ceramic piezoelectric sensor contacts to detect propagation of mechanical vibrations. The movement may be associated with breathing or heartbeat for example. The ceramic piezoelectric sensor may include a piezoelectric ceramic mass, such as a chip formed of a piezoelectric ceramic. Vibrations may induce generation of an electric signal by the piezoelectric ceramic mass. The signal may be processed by an analog to digital converter. In another example, a piezoelectric sensor comprises one or more piezoelectric strip sensors. Strip sensors may be suspended in some implementations. The strip or ceramic sensors may be suspended to isolate the sensors from motion of a movable platform or may be positioned coupled to the motion.

The piezoelectric sensor may be positioned at an appropriate location relative to and within an appropriate distance from the subject to detect motion of the subject, such as vertical motion or other directional motion and/or an associated pressure, force, or vibration. In one example, multiple strip or ceramic sensors may be used at various locations. In an embodiment, a piezoelectric sensor, such as a strip sensor or ceramic, may be positioned under a back or other location along the back of the subject when the subject is located on a platform. For example, the sensor may be embedded in a mat, mattress, sleep garment, or infant sleep sack, or attached to a platform, which in one example is a movable platform, upon which the subject is placed, either directly or on top of a mattress or pad positioned upon the platform. The subject may be positioned relatively horizontal with respect to a gravitational vector. In some embodiments, the subject may be positioned at angles to the horizontal such as in an inclined or declined position.

As introduced above, markers or tracking elements may be utilized in the collection of the subject data, including breathing related data. For example, a subject may be placed in a garment or sleep sack comprising one or more markers that a motion sensor, such as an optical or electromagnetic sensor, e.g., a radar device or video imaging sensor, or capacitance sensor may track, which may provide for increased resolution, sensitivity, and stability in the collected breathing related data. In one embodiment, a marker comprises an active marker that transmits a signal wherein a receiver receives the signal and determines proximity over time to identify motion. In another embodiment, markings or other features may be incorporated elsewhere in a region of data collection, such as on a sleep surface of a bassinet, and may be configured to differentiate between the body parts of the subject and the underlying or surrounding surfaces.

In an embodiment, a breath detection system may be configured to cooperate with a sleep sack of a bassinet. For example, the breath detection system may be configured to cooperate with a sleep sack similar to those described in U.S. patent application Ser. No. 14/448,679, filed Apr. 31, 2014, and U.S. patent application Ser. No. 15/055,077, filed Feb. 26, 2016, or PCT/US2017/057055, filed Oct. 17, 2017, both of which are hereby incorporated herein by reference. The sleep sack may be a device operable to swaddle an infant subject and enable the infant to be secured in a fixed position within the bassinet. Having the infant secured in a fixed position within the bassinet ensures that the sensing device may accurately address the infant and provide accurate motion data of the infant. The fixed placement of the infant within the bassinet allows for less variability of relevant features, such as the location of pixels corresponding to a subject's chest, within images that may be captured by imaging sensors comprising infant imaging cameras. Securing a subject in a fixed position within the bassinet may allow a processing module to more easily and confidently determine a subject's breathing and/or heartbeat condition. Furthermore, the previously mentioned markers or tracking elements configured to assist in data collection may be incorporated on or in said sleep sack.

Figure 1C:
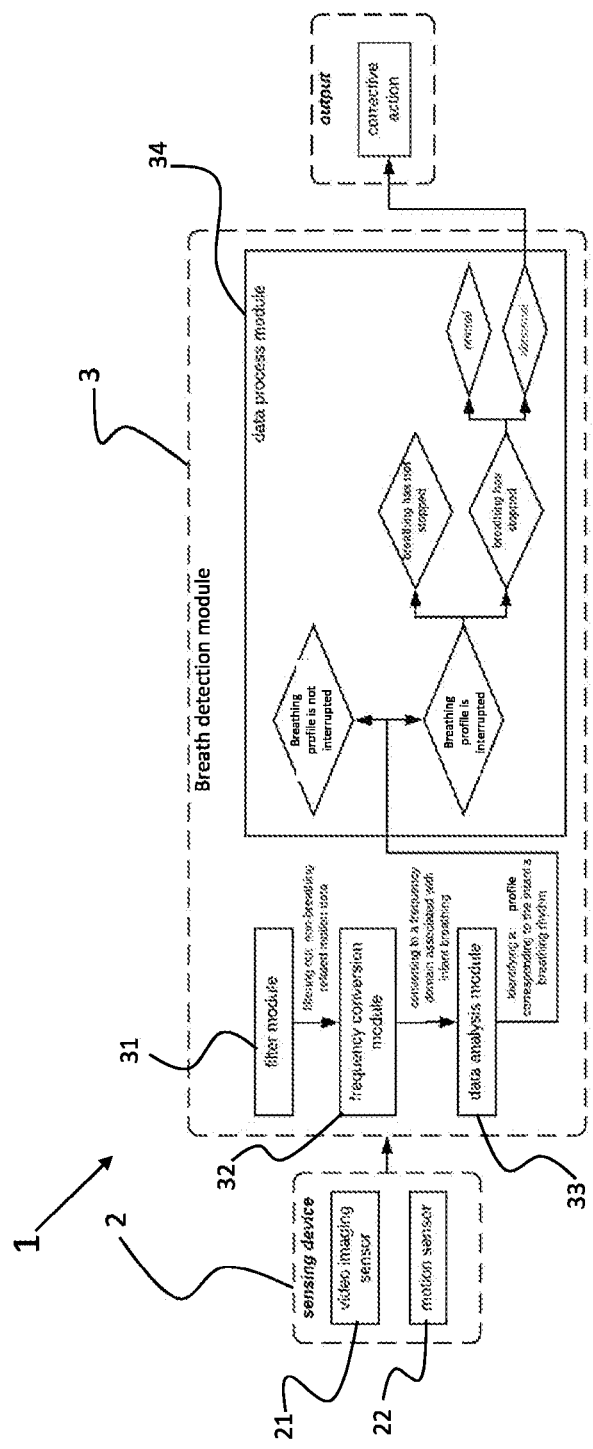
FIG. 1C schematically illustrates a system for breath detection according to various embodiments described herein.

FIG. 1C schematically illustrates an embodiment of a breath detection system 1 according to various embodiments. The breath detection system 1 may be configured to execute all or a combination of the steps of process 10, process 1100, or both.

The breath detection system 1 comprises or is configured to operatively couple to the outputs of one or more sensing devices 2 for collecting subject data. The sensing device 2 may include the features and operations described above and elsewhere herein with respect to sensing devices, such as biometric sensors including breath sensors. The sensing device 2 may comprise a motion sensor 22 comprising a video imaging sensor 21 and/or other motion sensor 22. Subject data captured by the sensing device 2 may be sent to a breath detection module 3 by wired or wireless electrical signal (e.g., Wi-Fi, Bluetooth, cellular, etc.). In some embodiments, the sensing device 2 includes a motion sensor comprising a piezoelectric ceramic or strip sensor (see, e.g., FIGS. 21-29B). In a further embodiment, the sensing device includes a microphone. The piezoelectric sensor may detect motion corresponding to breathing and/or heartbeat for processing by the breath detection module 3 according to FIG. 1C to determine if breathing and/or heartbeat is abnormal. The microphone may detect sounds associated with breathing, which may be similarly filtered. The sounds associated with breathing may be compared with those detected from motion data. Additionally, or alternatively, the sounds associated with breathing may be compared with sounds associated with breathing abnormalities, diseases, or illnesses for detection or early detection of the same.

The breath detection module 3 may include a receiver to receive subject data from the sensor device 2. In some embodiments, the breath detection module 3 includes a transmitter or transceiver to transmit signals to the sensor device 2 or to output a signal to a response device, which may be configured to sound an alarm, transmit a call, text, email, or message to a caregiver, or control movement of a moving platform of a bassinet, or undertake another action. The breath detection module 3 may further comprise a filter module 31, a frequency conversion module 32, a data analysis module 33 and a data process module 34. In various embodiments, the breath detection module 3 comprises a heartbeat detection module configured to handle subject data with respect to heartbeat detection (filter, conversion, analysis, processing, signal generation, etc.) in a manner similar to that described with respect to breathing detection. For example, a breath sensor comprising a piezoelectric, e.g., ceramic, sensor may be utilized to transform vibrations caused by heartbeat, breathing, or both breathing and heartbeat to electrical signals for analysis by the breath detection module. The piezoelectric sensor may be positioned along the platform or other vibratory structure either directly or indirectly in physical contact with the subject such that the sensor may detect vibrations propagated along the platform or other vibratory structure.

The breath detection system 1 and/or the breath detection module 3 thereof may be embodied in one or more computing systems that may be embedded on one or more integrated circuits or other computing hardware operable to perform the necessary functions of the breath detection system 1 and/or breath detection module 3. For example, the breath detection module 3 or sensing device 2 may include an analog to digital converter to process electrical signals generated by a piezoelectric sensor. In some embodiments, the breath detection system 1 and/or the breath detection module 3 thereof is integrated with a bassinet having a moving platform. For example, the breath detection system 1 and/or the breath detection module 3 thereof may be integrated with or be configured for communication with a control system operable to control operations of the moving platform and/or other features of the bassinet. In one example, the breath detection system 1 and/or the breath detection module 3 thereof comprises a remote device with respect to the bassinet and may communicate with the bassinet or control system thereof via a wireless or wired communication link. In another example, the breath detection system 1 and/or the breath detection module 3 thereof does not communicate with a control system of the bassinet. In one embodiment, the breath detection system 1 and/or the breath detection module 3 thereof comprises a portable system allowing a user to position the system with respect to a subject to collect subject data and monitor the same. For example, one or more sensor modules may be provided that the user positions around the subject to collect subject data. The breath detection module 3 may then be positioned to receive the collected subject data as input and used as described herein to monitor breathing of the subject.

The breath detection module 3 may be configured to receive collected subject data from the sensing device 2, which may include one or more sensors as described above and elsewhere herein, as input and generate an output signal when abnormal or interrupted breathing has been detected. The input subject data may include images captured by the one or more video/imaging sensors, electromagnetic wave data obtained by one or more motion sensors, or sound/motion/vibration sensor output data. In some embodiments, the breath detection module 3 may output statistics regarding subject breathing that may be sent and/or presented to a caregiver and/or medical professional. The statistics may provide information related to sleep parameters and/or patterns, subject environment, quality and/or duration of sleep, and/or breathing and/or heartbeat patterns such as frequency and/or variabilities. In one embodiment, output may include images and/or sound recordings of the subject that may be sent and/or presented to a caregiver.

The filter module 31 may be configured to filter out non-breathing related data from the subject data, such as non-breathing related motion data, obtained from the sensing device 2. For example, the non-breathing related motion data may arise from the movements of the bassinet, a roll-over movement of the subject, the movement of fabrics around the subject, or any other motion data arising from movement other than the breath of a subject. In some embodiments, filter module 31 may be configured to filter out non-heartbeat related data from the subject data, such as non-heartbeat related motion data, sound, or vibration data obtained from the sensing device 2. The filtered data may include filtered heartbeat related data, filtered breathing related data, and/or combined filtered heartbeat and breathing related data.

The frequency conversion module 32 may be configured to convert filtered subject data for analysis and/or modeling. For example, filtered subject data may be sent to the frequency conversion module 32 for conversion of the filtered data to a frequency domain associated with subject breathing. In general, this frequency will typically be below 10 Hz. The same or different filtered subject data may be sent to the frequency conversion module 32 for conversion of the filtered data to a frequency domain associated with subject heartbeat.

The data analysis module 33 may be configured to receive the converted data from the frequency conversion module 32 and to identify a profile within the frequency domain data corresponding to the subject's breathing rhythm and/or heartrate rhythm.

The data process module 34 may be configured to analyze the signature of a subject from the analysis module 33. The data process module 34 may be further configured to make decisions based on the breathing related data, which may include filtered, converted, and/or analyzed breathing related data. The data process module 34 may be configured to determine if the subject breathing has stopped by analyzing the signature. If there is a loss of signature, the data process module 34 will determine if it arises from subject breathing stoppage or various non-emergency circumstances, for example, when a subject has been taken out, or there is a physical obstruction of the sensing device. Thus, if the subject breathing has stopped, the breath detection module is further configured to determine if the stoppage is abnormal or normal. The subject breathing profile determined over time may comprise customized baseline data, which may further be utilized by the breath detection module to reduce false positives, which are a false diagnosis of abnormal breath stoppage. If the stoppage is determined to be abnormal, e.g., sufficient to reach or exceed a threshold corresponding to a trigger event, the data process module 34 may be configured to generate an output signal.

The data process module 34 may be further configured to make decisions based on the heartbeat related data, which may include filtered, converted, and/or analyzed heartbeat related data. The data process module 34 may be configured to determine if the subject heartrate has stopped or slowed by analyzing the signature. If there is a loss of signature, the data process module 34 will determine if it arises from subject heartrate stoppage or threshold slowing or various non-emergency circumstances, for example. Thus, if the subject heartbeat has stopped or reached a threshold slowing, the breath detection module is further configured to determine if the stoppage or slowing is abnormal or normal. The subject heartbeat profile determined over time may comprise customized baseline data which may further be utilized by the breath detection module 3 to reduce false positives, which are a false diagnosis of abnormal heartbeat. If the stoppage or slowing is determined to be abnormal, e.g., sufficient to reach or exceed a threshold corresponding to a trigger event, the data process module 34 may be configured to generate an output signal.

An output signal with respect to breathing and/or heartbeat may preferably be an electrical signal or otherwise and be sent to a sound control module, a motion control module, or to a communication module. The sound control module, motion control module, or a communication control module may be associated with a bassinet. For example, the motion control module may move a platform having a motive platform, for example. Various other signal receiving modules may further be configured to operate the moving platform. In one embodiment, the output signal may preferably be an electrical signal or similar and may be sent to a motion or sound control module of the moving platform, such as a bassinet, or to a communication module of the bassinet, or to various other signal receiving modules and may further be configured to operate the moving platform. Alternatively or additionally, the output signal may be configured to be received by an alert system, such that, for example, parents, paramedics, or anyone taking care of the subject can be notified. For example, the signal may be transmitted according to a protocol compatible with a communication protocol of the alert system. In some embodiments, the alert system may comprise a cellular, internet, or network server, router, gateway, or other communication device, for example. The alert system may be configured to provide alerts via text message, SMS, push notification, voice messaging, etc. In one embodiment, the breathing detection system or alert system may integrate with and/or communicate with health care/hospital monitoring systems. For example, the system may provide raw or processed data, notifications, and/or alerts to third party systems. The system may also integrate with third party systems.

In an embodiment, the breath detection system 1 may operate with, be attach to, or be integrated with a bassinet. For example, the breath detection system 1 may be integrated or utilized with a bassinet as disclosed in U.S. patent application Ser. No. 14/448,679, filed Apr. 31, 2014, or U.S. patent application Ser. No. 15/055,077, filed Feb. 26, 2016, or PCT/US2017/057055, filed Oct. 17, 2017, all of which are hereby incorporated herein by reference. In one example, the breath detection system 1 may include a main body comprising a processing module including all or a portion of the breath detection module 3. The main body may be configured to be positioned above the bassinet and roughly centered above a subject laying inside the bassinet. In one example, the main body further comprises one or more sensor devices 3. In another embodiment, a breath detection system 1 may be attached sparsely around a bassinet such that it is able to capture the movement of a subject laying inside the bassinet. In a further embodiment, the sensing device 2 of the breath detection system 1 may be attached sparsely around a bassinet such that it is able to capture sound of a subject laying inside the bassinet. In one embodiment, the system 1 may include a processing module that may be integrated with a bassinet or positioned to receive collected of subject data therefrom, which may include wired or wireless communication with the sensor device 2 comprising one or more sensors positioned around or within the bassinet. The processing module may be further configured to output a signal, such as a corrective action signal.

Figure 4:
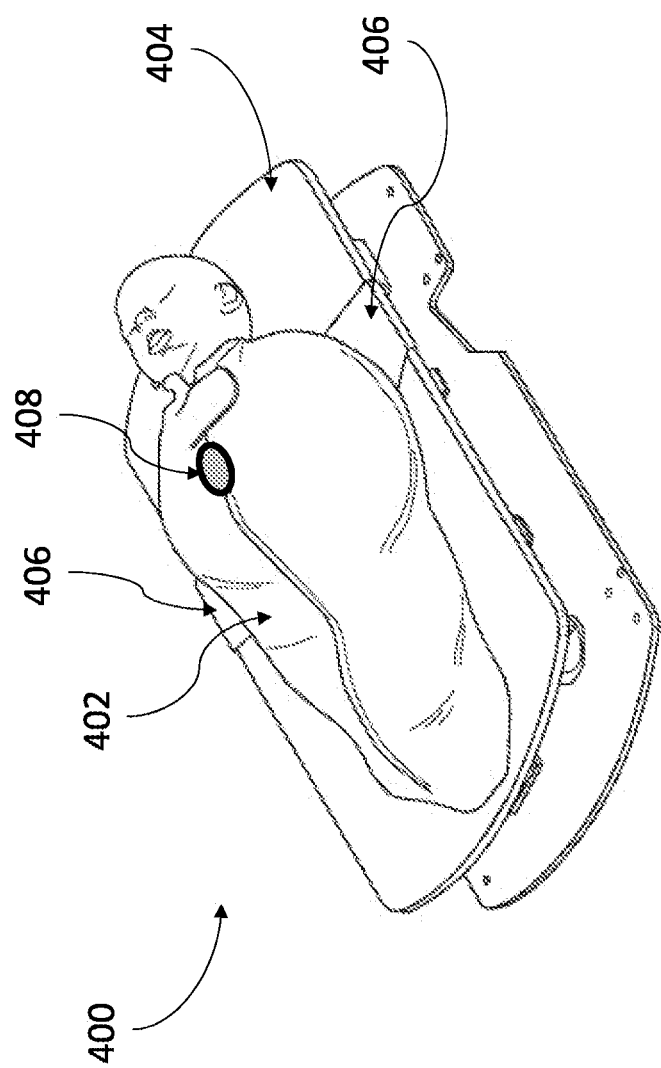
FIG. 4 is a perspective view of an infant sleep garment and sleep platform system according to various embodiments described herein.

FIG. 4 illustrates a perspective view of an embodiment 400 of a sleep sack 402 and an infant platform 404. The sleep sack 402 may be configured to attach to the sleep surface at wing element 406 so as to secure the infant subject in a desired position, as well as in a desired location, thereby allowing for a sensor to more accurately address the subject on a consistent basis and collect higher quality subject-breathing data. In an embodiment, the sleep sack 402 and/or the sleep platform 404 may be equipped with markers 408 or sensors, e.g., as described above, configured to mark or report their location to a sensing device or other data collection device. Thereby, a relative motion of the subject's chest, for example, can be identified relative to other movements present in the proximity, such as a movement of platform 404. Marker 408 is configured to remain positioned above the subject's chest area, and will move in an up and down motion relative to platform 404 as the subject breathes. A sensor system (not shown) may then be configured to track the motion of marker 408 in order to establish a breathing frequency of the subject.

Figure 2A:
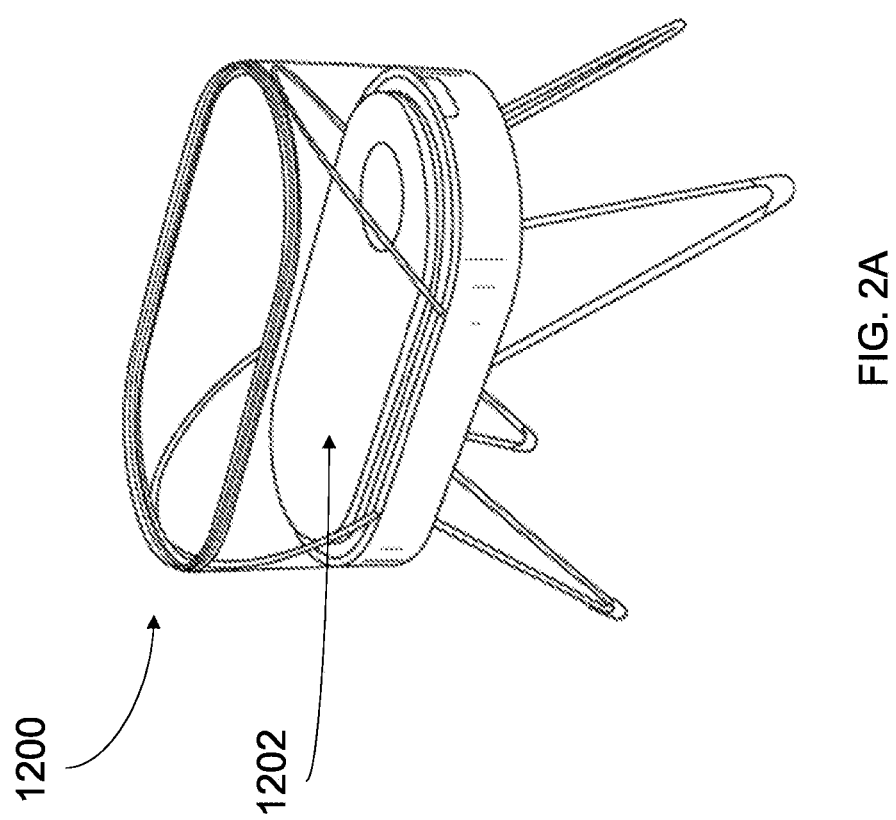
FIG. 2A is a perspective view of a bassinet and platform for accommodating a subject according to various embodiments described herein.

FIG. 2A is a perspective view illustration of an embodiment 1200 of a bassinet. Bassinet 1200 may be configured to accommodate a sleeping infant subject on sleep platform 1202. Sleep platform 1202 and bassinet 1200 may be further configured to accommodate a breath detection system as described herein. In an embodiment, platform 1202 may comprise a moving platform connected to a controllable motor to drive a motion of the platform 1202, examples of which are described in more detail below with respect to FIGS. 9-16. In response to a signal from a processing module such as breath detection module 3, the platform 1202 may be configured to respond by vigorous shaking or other motion designed to stimulate a subject and promote breathing when an abnormal breathing stoppage has been determined to have occurred according to the principles disclosed herein.

Figure 2B:
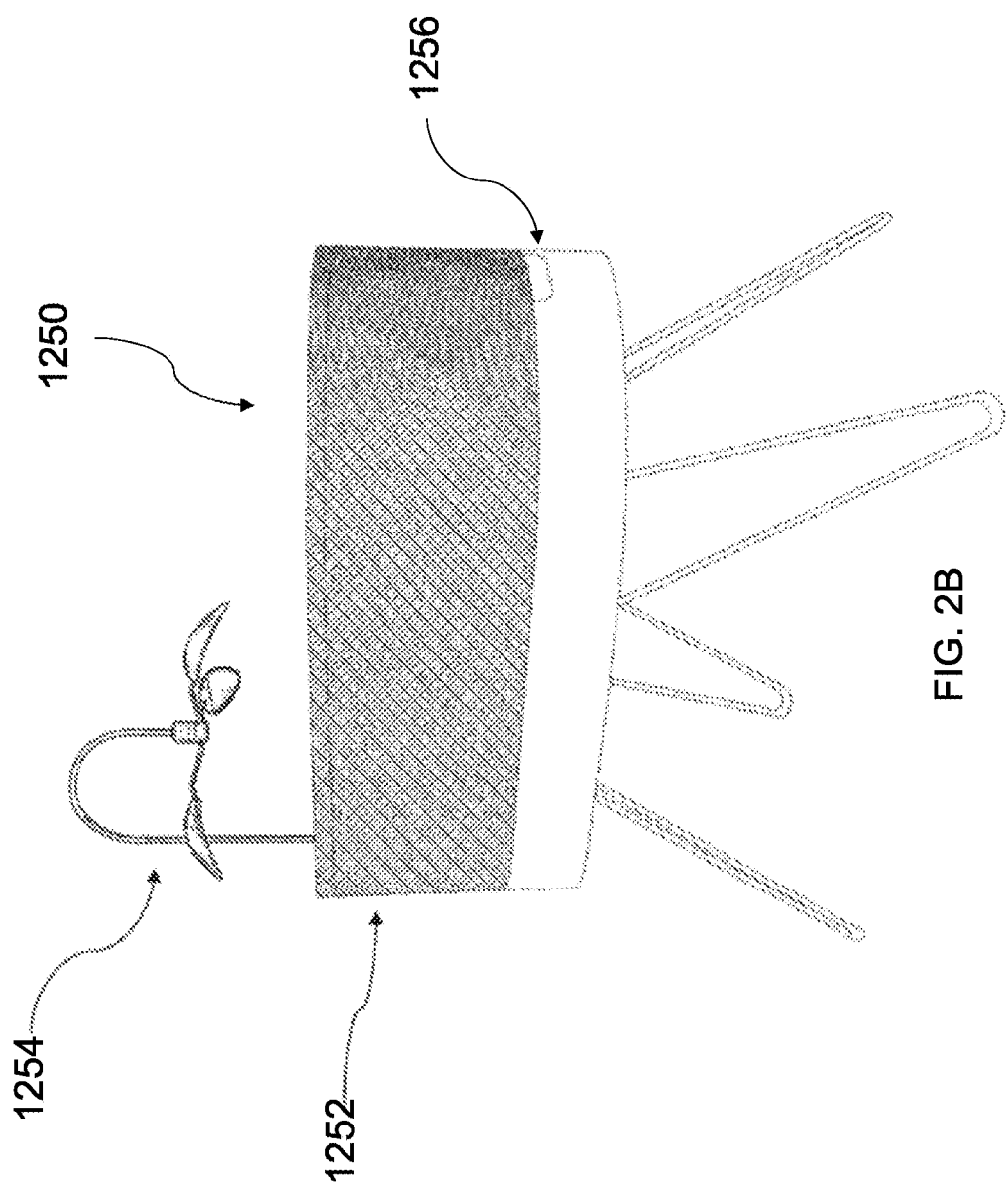
FIG. 2B is a perspective view of an sleep system for breath detection according to various embodiments described herein.

FIG. 2B is a perspective view illustration of an embodiment 1250 of a bassinet and sensor system. System 1250 comprises a bassinet 1252, a sensing device 1254, and a breath detection system 1256. In the embodiment shown, a subject may be placed inside bassinet 1252, and may be addressed by a sensors 1254, which in certain embodiments may be made to look or function alternatively as a mobile. The sensor 1254 may be configured to effectively address the subject so that subject-breath related data may be collected and communicated to processing module 1256, where the data is analyzed, monitored, and responded to according to the principles disclosed herein. Thus, sensor 1254 may be referred to as a breath sensor. In various embodiments, sensor 1254 comprises a microphone configured to detect sounds from the subject corresponding to breathing. In this or another embodiment, sensor 1254 comprises a video camera configured to image the subject in the visual or infrared spectrum. In one example, the processing module 1256 may correlate video imaging data with sound data to detect breathing. Processing module 1256 in an embodiment may not only perform the analysis and algorithms disclosed herein, by may additionally control a sleep system comprising a number of other functions and modules, such as infant crying detection, motion and sound sensing, control of a movable sleep platform, behavior state detection, audio generation, as well as audio, motion, and status outputs, such as the system disclosed in PCT/US2017/057055 entitled "Infant Calming/Sleep-aid Device", which is incorporated herein by reference in its entirety, and which is described in part in FIG. 3 herein.

Figure 3:
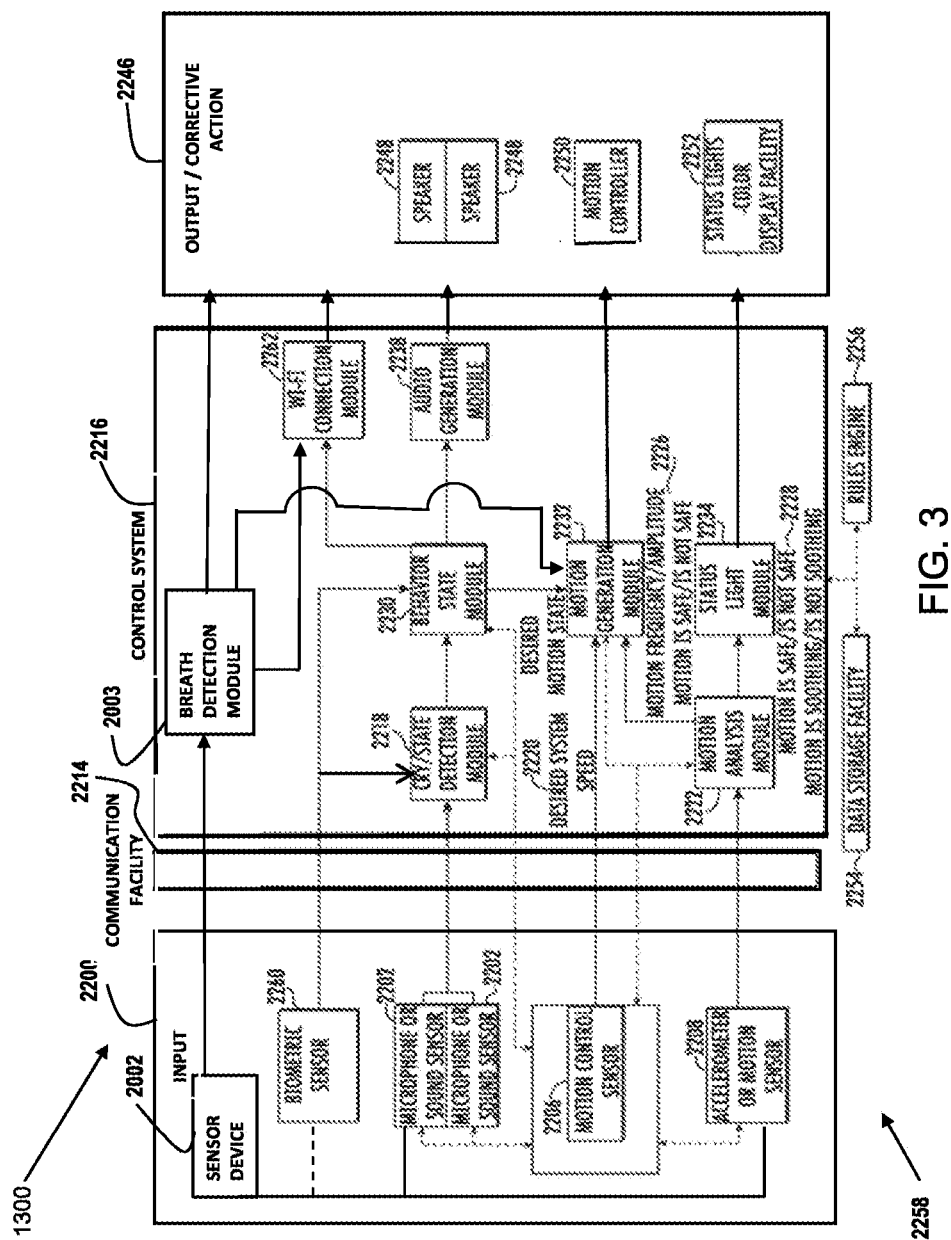
FIG. 3 schematically illustrates an sleep system processing module according to various embodiments described herein.

FIG. 3 schematically illustrates operations and functional units of a processing system 1300 configured to interface with the sensor device and bassinet embodiments described herein, such that analysis, filtering, monitoring, detecting, and responding to breathing related data collected from one or more sensors in a breath detection system, such as breath detection system 1 described above with respect to FIG. 1C, may be performed by a broader system, such as system 1300 as part of a subsystem thereof. Thus, the breath detection system 1 (FIG. 1C), process 10 (FIG. 1A), and/or process 1100 (FIG. 1B) described herein may be executed as a subsystem of system 1300. System 1300 may also be configured to perform one or more additional sleep system functions, such as infant crying detection, motion and sound sensing, control of a movable sleep platform, behavior state detection, audio generation, as well as audio, motion, and/or status output signals, for example. System 1300 may also be configured to perform heartbeat detection as described herein.

System 1300 may include an infant calming/sleep-aid device 2258 comprising various control system related components including a control system 2216 including a control processor for receiving and processing inputs 2200 and generating outputs 2246 and a communication facility 2214. In some embodiments, system 1300 further includes a user interface. It is to be appreciated that the control system 2216 may include various components depending on implementation needs, which may include, for example, various combinations of a motor, driver, sensory circuit, or microprocessor. Components of the control system 2216 and the user interface may be located on-board or remotely from the enclosure/platform portion of infant calming/sleep-aid device 2258.

Inputs 2200 may include data or control signals from sensor device 2002 comprising one or more sensors, as described above, including various types of sensors or devices such as a microphone or sound sensor 2202, motion control sensor 2206, accelerometer or motion sensor 2208, user interface, biometric sensor 2260, mmWave or UWB radars and the like. The biometric sensor 2260 may include a breath sensor or other sensor configured to detect physiological parameters and may include motion sensors, vibration sensors, sound sensors, temperature sensors, weight sensors, galvanic skin response sensors, oxygen sensors, or the like. In the provided illustration sound sensors 2202 is provided as a representation of a sound sensor for detection of crying while motion sensor 2208 is provided as a representation of a motion sensor to detect movement of a subject related to body movements such as gross body movements related to kicking, crying, flailing, rolling, rocking, or other movements indicative of behavior. However, it is to be appreciated that in some embodiments such motion and/or sound sensors 2208, 2202 may similarly be used with respect to biometric sensor 2260 to detect physiological parameters. Although, in some embodiments, the biometric sensor 2260 includes different motion and/or sound sensors that are employed to detect physiological parameters. In an embodiment, biometric sensor 2260 could be an accelerometer or vibration sensor, such as a piezoelectric sensor, and act to detect/measure the breathing and/or heartbeat of a subject by measuring vibrations along a platform of the bassinet, which may be configured to move, a mat, mattress, sleep garment, or infant sleep sack, for example. Sensing device 2002 may include the features and functionalities described above and elsewhere herein with respect to the sensing device in process 10 (FIG. 1A), process 1100 (FIG. 1B), and breath detection system 1 (FIG. 1C).

Outputs from the control system 2216 may be directed to modules or devices thereof such as one or more speakers 2248 for controlling the generation of sound, motion controller 2250 for controlling the motion of a platform or structure on which the subject is placed, call to emergency services using communication connection module 2262, and status light facility 2252 for controlling illumination of various status lights, or IoT connected lights in the house. Connection module 2262 may include a Wi-Fi connection, cellular, land line communication, or other communication connection route for transmitting message communications, e.g., calls, emails, alerts, text messages, posts, etc. For example, the connection module 2262 may be configured to transmit signals and/or data communications according to a compatible communication protocol for routing the message. In various embodiments, the message may be routed to an alert system, caregiver, user communication device, emergency services, hospital, or third party resource. Messages may be transmitted, for example, as text messages, SMS, push notification, voice messaging, etc. In one embodiment, the system 1300 or connection module 2262 may integrate with and/or communicate with health care/hospital monitoring systems. For example, the system 1300, via connection module 2262, may provide raw or processed data, notifications, and/or alerts to third party systems. The system 1300 may also integrate with third party systems.

Other inputs from the sensing device 2002 may also be provided by other sensors, which may include motion and/or sound sensors 2202, 2208, such as optical sensors, including cameras, mmWave and UWB radars, pressure sensors, weight sensors, mechanical stress sensors and/or vibration sensors, such as piezoelectric sensors. Additional or other inputs from the sensing device 2002 that may be provided by other sensors may include inputs from one or more sound sensors 2208, such as microphones, pressure sensors, or vibration sensors, such as piezoelectric sensors. In various embodiments, biometric sensor 2260 includes the same or different motion and/or sound sensors 2202, 2208, which may function as a breath sensor 269 (see FIG. 13), and which may include any suitable breath sensor 269, such as those described herein. Breath sensors 269 may be configured to detect breathing, heartbeat, and/or motion.

In some embodiments, breath sensors 269 may be used to detect vibrations corresponding to vocalizations of the subject. For example, crying may be analyzed using motion and sound. The acoustic vibration of a cry has both audible and non-audible components, namely an expiration and inspiration component. Utilizing microphones and motion sensors to collect crying associated data may be used to improve cry identification with respect to a particular subject and/or cry characterization. For example, a microphone may be positioned proximate to the subject in a position to detect crying sounds. A sensor device 2002 comprising a biometric sensor 2260 configured to detect vibrations may be used. For example, a piezoelectric sensor, such as one also referred to herein as a breath sensor, may be used to detect vibrations from movement of the subject. Utilizing this implementation, both mechanical and acoustic vibrations of the subject's body may be detected and analyzed. Hence, the entirety of a cry event: voiced and unvoiced crying, may be advantageously captured. Thus, in some embodiments, the biometric sensor 2260 may collect motion data comprising vibrations associated with crying. This data may be provided to a cry/state detection module 2218 by the sensor device 2260 or biometric sensor 2260 thereof or the breath detection module 2003, for example. The cry/state detection module 2218 may compare the motion data with sound data collected by a microphone or sound sensor 2202 and determine if the detected sound corresponds to sound originating from the subject, e.g., as described in more detail below with respect to FIGS. 28A-29B.

Sensors of the sensor device 2002 may be positioned at suitable locations for detecting subject data. For example, sensors of the sensor device 2002 maybe located in along, beneath, above, or integrated with a sleep device, sleep device platform, mattress or sleep pad; above a subject, such as associated with a mobile; within, along, or adjacent to raised sidewalls surrounding a sleeping area of a crib or bassinet; integrated within padding along sidewalls; on or within a swaddle or sleep sack; embedded in fabrics; or the like. Sensors embedded in fabrics may be flexible sensors, for example. Sensors, e.g., biometric sensors 2260, may be used for detecting child physiological parameters.

Sensors of the sensor device 2002 may be used to provide inputs and feedback for a mode selection with respect to sound and/or motion ranges for a mechanism that activates the calming reflex of an infant or, in certain circumstances, increases a baby's arousal. Microphone or sound sensor 2202 may be in communication with a user interface. Motion control sensor 2206 may be controlled by a user interface. Motion control sensor 2206 may be in communication with motion generation module 2232. Motion control sensor 2206 may send desired system speed input 2220 to motion generation module 2232.

Sensor device 2002 may send collected subject data to breath detection module 2003. For example, biometric sensor 2260 may detect subject breathing related data and/or other physiological parameters that the sensor device 2002 may provide to the breath detection module 2003. Breath detection module 2003 may include the features and functionalities described above and elsewhere herein with respect to the sensing device in process 10 (FIG. 1A), process 1100 (FIG. 1B), and breath detection system 1 (FIG. 1C). For example, breath detection module 2003 may filter and analyze the subject data. The collected subject data may include non-breathing related data that may be filtered to isolate breathing related data. The collected subject data may include non-heartbeat related data that may be filtered to isolate heartbeat related data. Filtering may include removal of motion and/or sound data corresponding to movement of the platform or other non-breathing and/or non-heartbeat related motion or sound. The breath detection module 2003 may convert filtered breathing and/or heartbeat related data into frequency domains. The breath detection module 2003 may generate, update, modify, and/or select subject breathing profiles. The breath detection module 2003 may make decisions with respect to breathing patterns and threshold events based on breathing related data and subject breathing profiles. Such decision may be a combination of heartrate and airwave obstruction; where the obstruction can be deduced from the motion pattern and an increased heartrate; to differentiate it from rapid movements due to other reasons. The breath detection module 2003 may generate, update, modify, and/or select subject heartbeat profiles. The breath detection module 2003 may make decisions with respect to heartbeat patterns and threshold events based on heartbeat related data and subject heartbeat profiles. In some instances, the breath detection module 2003 may provide and output signal corresponding to corrective action 2246 as described above. For example, the breath detection module 2003 may utilize connection module 2262 to send an alert to a caregiver, an emergency services provider, hospital monitoring system, e.g., an alarm, message, SMS, push notification, email, text, phone call, etc. The breath detection module 2003 may utilize speaker 2248 to initiate an alarm or alert. Breath detection module 2003 may send a signal to motion controller 2250 of the moveable subject sleep platform to activate a stimulating mode of operation intended to wake the subject and resume normal breathing and/or heartbeat. The breath detection module 2003 may send a signal to status lights 2252 to initiate light alerts.

Microphone or sound sensor 2202 may send data to cry/state detection module 2218. Accelerometer or motion sensor 2208 may send motion data to motion analysis module 2222. Communication facility 2214 may be used to establish communication between inputs 2200 and control system 2216. Communication may be established via direct control, remote control, and the like. Direct control may include providing control inputs to the communication facility from input devices directly integrated with the infant calming/sleep-aid device. Remote control may include providing control inputs to the communication facility from input devices remotely connected to the infant calming/sleep-aid device. Remote connectivity may include wired and wireless connectivity. Wireless connectivity may include Wi-Fi connectivity, Bluetooth connectivity, and the like. Journaling may include track feedings, track diapers, and the like.

Control system 2216 may include various modules. Modules may include cry/state detection module 2218, behavior state module 2230, audio generation module 2238, motion generation module 2232, motion analysis module 2222, status light module 2234, and the like.

In one embodiment, modules include a detection module 2260. The breath detection module 2003 may be separate from or a component of the control system 2216. For example, biometric sensor 2260 of sensor device 2002 may be in communication with breath detection module 2003 to monitor physiological parameters of the subject, such as one or more heart rate, body temperature, breathing/respiration, blood pressure, or weight, for example. As described above with respect to FIGS. 1A-1C, the biometric sensor 2260 may generate a signal indicative of a respiration status and/or a cardiovascular status of the subject, such as to detect when the subject has paused breathing for a predetermined period or time, or has a cardiovascular collapse, such as indicated by a heartrate above or below a predetermined threshold, or the like. In a further embodiment, the breath detection module 2260 may further compare a breathing and/or heartbeat signature generated from the biometric sensor signal to a breathing and/or heartbeat profile associated with the subject to determine if the collected respiration and/or cardiovascular data is abnormal or otherwise outside of an expected range of respiration or cardiovascular data for the subject. If the respiration and/or cardiovascular status is determined to be outside a threshold and/or outside an expected range of variation, the breath detection module 2203 may generate a signal for output of corrective action 2246 as described above and elsewhere herein, such as initiation of a sound directed at the subject from a speaker 2248, initiation of an notification or emergency call, e.g., via a Wi-Fi connection module 2232, and/or by initiation of motion of a moveable platform via motion generation module 2232.

Cry/state detection module 2218 may be in communication with microphone or sound sensor 2202, motion control sensor 2206, behavior state module 2230, and the like. Cry/state detection module 2218 may send a crying/not crying status input, along with a quantification of a crying episode to behavior state module 2230.

Biometric detection module may be in communication with motion generation module 2232, audio generation module 2238, and the like. Biometric detection module may send desired motion state input 2260 to motion generation module 2232, desired audio track, desired volume/equalizer settings input 2236 to audio generation module 2238, and the like. Behavior state module 2230 may be in communication with crying detection module 2218, motion generation module 2232, audio generation module 2238, and the like. Behavior state module may send desired motion state input 2260 to motion generation module 2232, desired audio track, desired volume/equalizer settings input 2236 to audio generation module 2238, and the like. Motion generation module 2232 may be in communication with behavior state module 2230, motion control sensor 2206, user interface 2201, motion analysis module 2222, motion controller 2250, and the like. Motion analysis module 2222 may be in communication with accelerometer or motion sensor 2203, user interface 2201, motion generation module 2232, status light module 2234, and the like. Motion analysis module 222 may send motion frequency/amplitude and motion is safe/is not safe input 2226 to motion generation module 2232.

Motion analysis module 2222 may send motion is safe/not safe input and motion is soothing/is not soothing input 2228 to status light module 2234. Motion generation module may send target motor positions/speeds input to motion controller 2250 and the like. Audio generation module 2238 may be in communication with behavior state module 2230, one or more speakers 2248, and the like. Audio generation module 2238 may send audio generation module input to one or more speakers 2248. Status light module 2234 may be in communication with motion analysis module 2222 status lights color display facility 2252 and the like. Status light module 2234 may send target status light colors input to status lights color display facility 2252 and the like.

Control system 2216 may also be in communication with data storage facility 2254, rules engine 2256, and the like. Data storage facility 2254 may store information that may be accessed by other modules of the control system 2216, and the like. Rules engine 2256 may provide rules for inputs and triggers to a mechanism to activate the "calming reflex" of an infant subject.

A user interface may be in communication with inputs such as microphone or sound sensors 2202, cry/state detection module 2218, motion analysis module 2222, accelerometer or motion sensor 2208, and the like. The interface may allow a user to input data such as date of birth of an infant or other subject, gestation age at birth, conditions, due date of a subject, name or an identifier for the subject, sex, weight of the subject, and the like. Weight of the subject may be input manually or automatically. The weight of the subject may be input automatically from a scale that is integrated with the infant calming/sleep-aid device 2258. The inputs may be used to select or identify a suitable subject breathing profile and/or heartbeat profile. Additional inputs may include information inputs. Information inputs may include baby weights, baby lengths, baby circumferences, frequencies, travel, immunizations, illness, heart rate, respiratory rate, blood oxygenation, and the like. Baby weights may include weight at birth, baby weights at different weightings, and the like. Baby length may include baby length at birth, baby length at different measuring's, and the like. Baby circumference may include baby circumference of the head at birth, baby circumference of the head at different measuring's, and the like. The user interface may be used to boost baseline stimulation by providing more motion and sound. The user interface may be an integral part of the infant calming/sleep-aid device, or a separate piece, such as on a mobile peripheral device, which may be connected by a wired connection, a wireless connection, and the like to the infant calming/sleep aid device. The wireless connection may be a Wi-Fi connection, Bluetooth connection, and the like. The user interface may have controls, set-up information input, and other input data that can be sent to the control system of the device. Controls may include an on/off control, sound control, motion control, light control, and the like. Controls may be enabled or disabled.

In some embodiments, a user interface may be provided as a mobile application. The mobile application may provide data inputs to the control mechanism of the infant calming/sleep aid device 2258. Data may include monitoring data, feedback data, control data, reporting data, analytics data, statistics, and the like. The mobile application may be installed on a mobile device. The device may be a smartphone, tablet computer, and the like. The mobile device may have an operating system that may be iOS, Android, and the like. The mobile application may enable interactions with the device. Interactions may be enabled through a communication interface. The communication interface may be a universal serial bus (USB) interface, Wi-Fi interface, Bluetooth interface, and the like. Interactions may be control interactions. Control interactions may be similar to the interactions that may be enabled directly from the infant calming/sleep aid device 2258, only available on the mobile application, and the like.

Other mobile device interactions may include reports and statistics, sharing and group interactions, benchmarking and comparison interactions, graphic interactions, acoustic signature of a cry interactions, data upload to a third party interactions, feedback from a subject matter expert interactions, warning alert interactions, overtone customization of white noise interactions, other input interactions, journal sharing/printout interactions, weight interactions, breastfeeding interactions, camera interactions, and the like. Other input interactions may include photo input interactions, video input interactions, audio input interactions, and the like.

Figure 5:
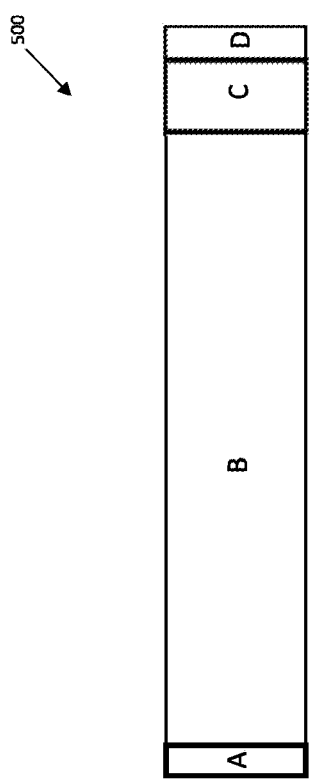
FIG. 5 schematically illustrates an example buffer for use by a breath detection module with respect to detection of intermittent breathing and breath per minute analysis according to various embodiments described herein.

FIG. 5 schematically illustrates an example buffer 500 for use by a breath detection module with respect to detection of intermittent breathing and breath per minute analysis according to various embodiments. The buffer 500 may be utilized by a breath detection module employing a sensor device as described herein. For example, the breath detection module may utilize a piezoelectric approach using a signal from a sensor device comprising a piezoelectric sensor that is placed such that when the baby is breathing the sensor is deflected and thus generates a signal. In one example, the sensor may be placed under a mattress. The generated signal may then be filtered and analyzed. In one embodiment, filtering may include amplification and/or conversion. For example, the signal may be transmitted to an amplifier and then an analog to digital converter. The breath detection module may then read the amplified values. The breath detection module with respect to FIG. 5 and FIGS. 6 & 7 is generally described as reading the amplified values at a sample rate of 100 Hz, but those having skill in the art will appreciate upon reading the present disclosure that other sampling rates may be used.

The buffer 500 shown in FIG. 5 stores data according to a first in first out (FIFO) order. Portion A represents sample which is removed from the buffer 500 when a new sample arrives. Portion D illustrates new acquired sample at the sample rate. Portion C represents a portion of the buffer that together with portion D is used as a buffer length of a predetermined period for detection of intermittent breathing (see FIG. 7). Portion B represents a portion of the buffer that together with portions A, C, and D comprise the buffer length of a predetermined period use for breaths per period calculation (see FIG. 8).

Figure 6:
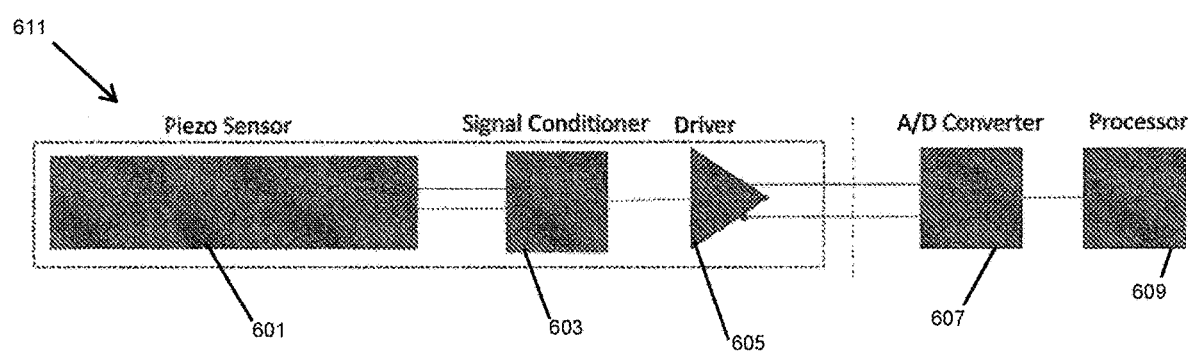
FIG. 6 schematically illustrates a process flow for detecting breathing according to various embodiments.

FIG. 6 schematically illustrates a process flow for detecting breathing using a breath sensor 611 including a piezoelectric element 601 according to various embodiments. The breath sensor 611 may be a sensor device, such as a biometric sensor of a sensor devices 2, 2002, described with respect to FIGS. 1C & 3. In one example, the breath sensor 611 may be similar to that described with respect to FIGS. 17-22 or elsewhere herein. Force, strain, or pressure applied along the piezoelectric element 601 of the breath sensor 611 may be converted to an electric signal that may be conditioned by a signal conditioner 603. The conditioned signal may be transmitted through a driver 605 to an analog digital convertor 607 to convert to a digital signal which may then be processed by a processor 609. The processor 609 may be a component of a controller or sensor control system as described herein or may be configured to transmit processed data to the same.

Figure 7:
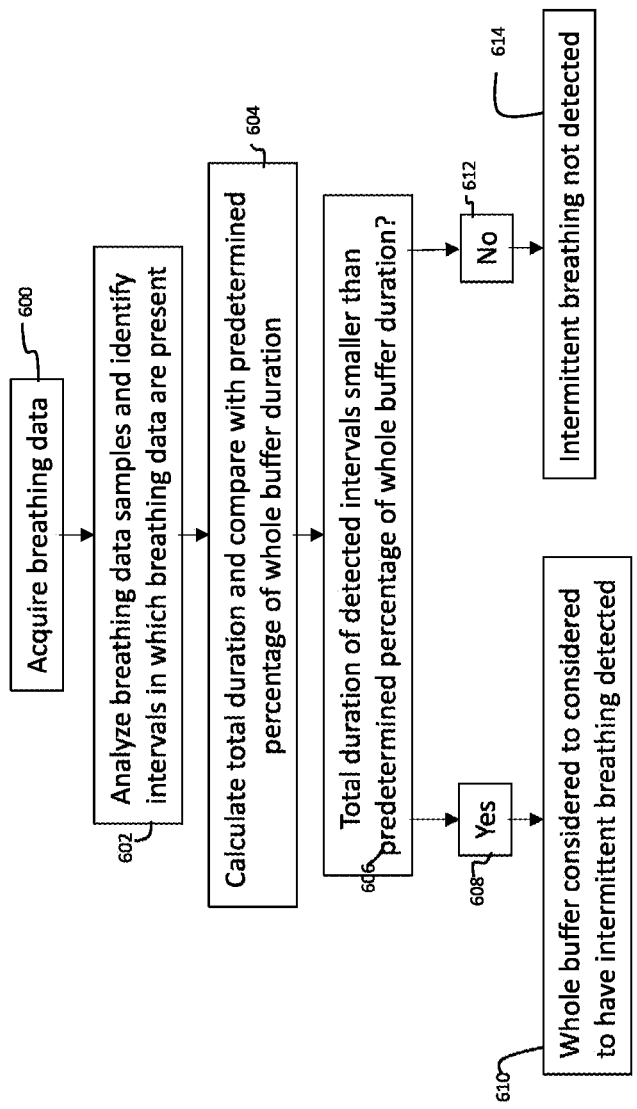
FIG. 7 illustrates a method of detection of intermit breathing according to various embodiments described herein.

FIG. 7 illustrates a method of detection of intermit breathing according to various embodiments. Intermittent breathing can be manifested as a period in which breathing is not taking place. Example, causes of intermittent breathing may be sleep apnea, simple irregular breathing intervals. The breath detection system may be configured to detect breathing intervals to determine a baby current status. The breath detection module may acquire breathing data 600 for an initial period of time, for example 2 seconds, but other periods may be used. The breath detection module may then analyze the breathing data samples and identify intervals in which breathing data are present 602. For example, the breath detection module may go through each sample in a buffer and locate intervals in which there is data from breathing. The breath detection module may apply one or more conditions with respect to detection of intervals. For example, the detection module may require that breathing signals must satisfy amplitude and duration conditions. Amplitude conditions may set upper, lower, or both upper and lower signal amplitudes. For example, breathing signals may be required to have an amplitude greater than 20 mV to filter visible noise disturbances found to have amplitude around or lower 20 mV. It should be appreciated that amplitude conditions will depend on the signal methodology and circuitry employed. The duration conditions may set upper, lower, or both upper and lower signal durations. For example, duration conditions may require that duration of currently detected interval is longer than 15 ms to be considered part of the breathing signal, not noise. When the intervals have been detected, the total duration may be calculated and compared with a predetermined percentage of the whole buffer duration 604 being used, although larger or the entire buffer may also be used in some embodiments. If the total duration of detected intervals is smaller than a predetermined percentage of the whole buffer duration or other predetermined period of time 608 then the whole buffer is considered to have intermittent breathing detected 610. If the total duration of detected intervals is larger than the predetermined percentage of the whole buffer duration or other predetermined period of time 612 intermittent breathing is not considered to be detected 614. For example, portion A in FIG. 5 may represent a new sample acquired with a sample rate of 100 Hz and the total duration of intervals in which breathing signal was identified during portions C and D, e.g., 2 seconds, may be calculated and compared with 20% of the whole buffer duration A-D, e.g., 60 seconds. If the total duration of detected intervals is smaller than 20% then the whole buffer is considered to have intermittent breathing detected. In one embodiment, intermittent breathing detection may be performed on every new 2 seconds of buffer, although other periods may be used in other embodiments.

Figure 8:
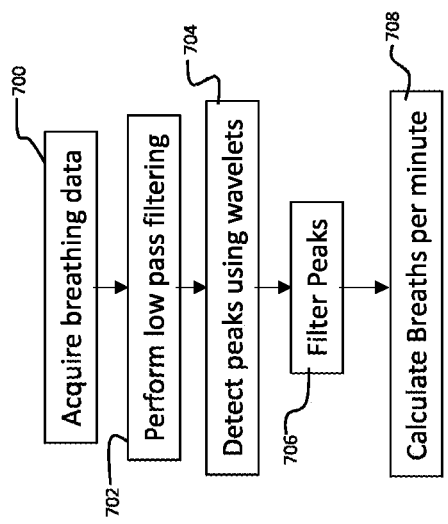
FIG. 8 illustrates a method of calculation of breaths per period according to various embodiments described herein.
Figure 9:
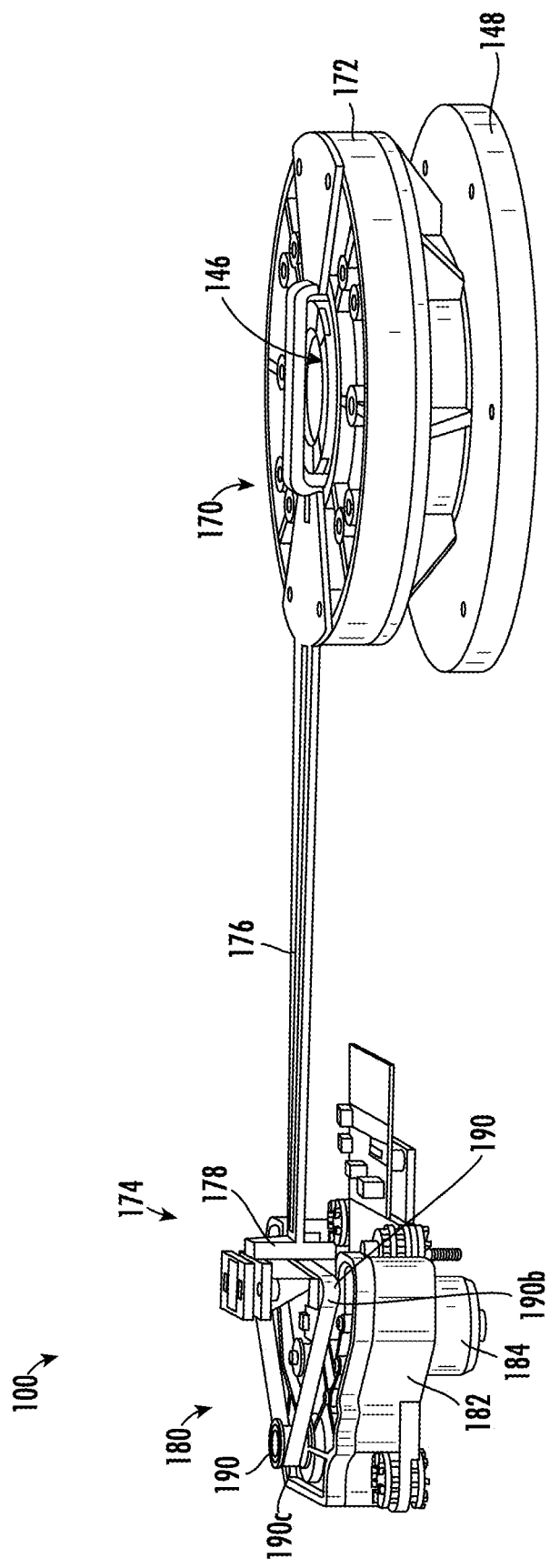
FIG. 9 illustrates a perspective view of a drive system according to various embodiments described herein.
Figure 10:
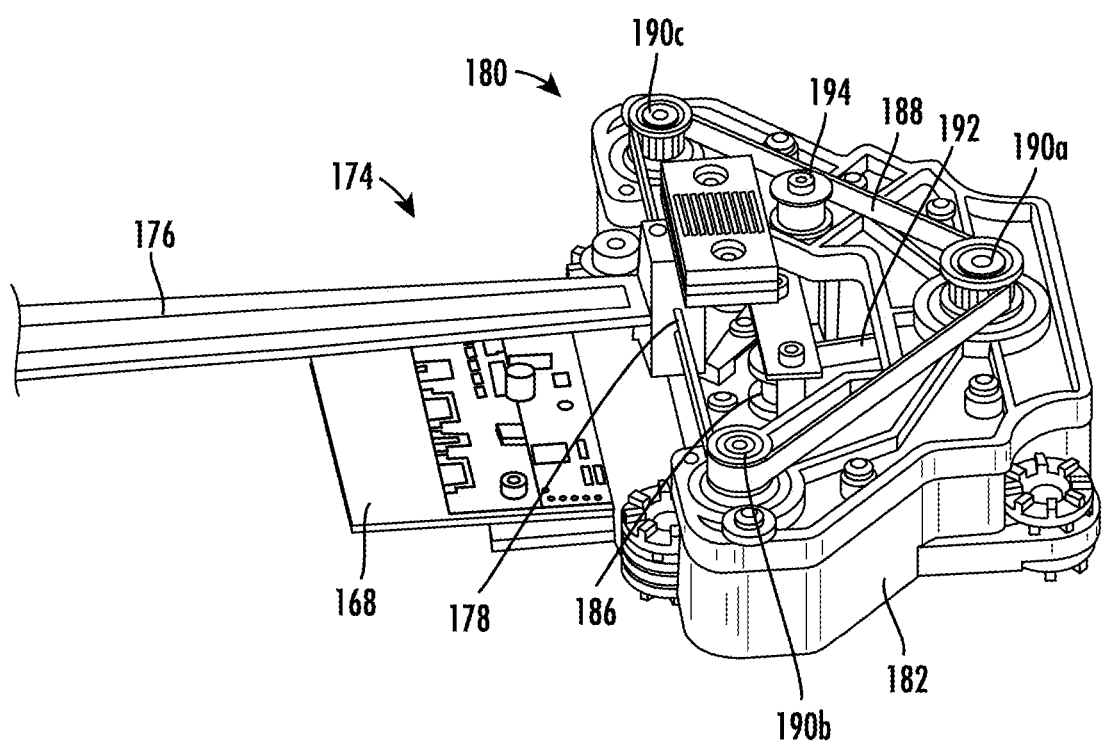
FIG. 10 illustrates an isolated view of the drive module and drive belt attachment assembly of a drive system according to various embodiments described herein.
Figure 11:
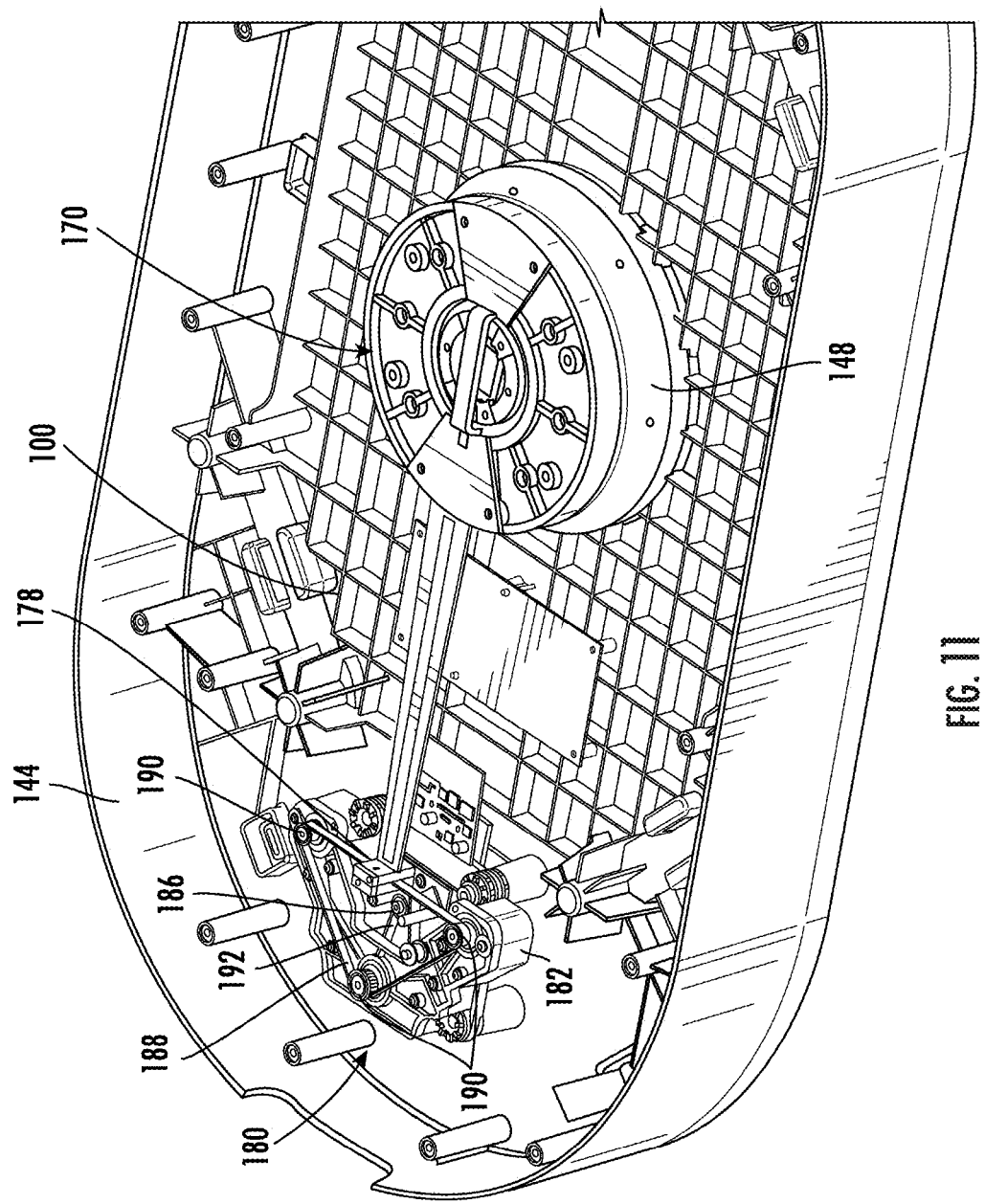
FIG. 11 illustrates a partial view of the drive system shown in FIG. 9 positioned within a base with certain components removed for clarity according to various embodiments described herein.
Figure 12:
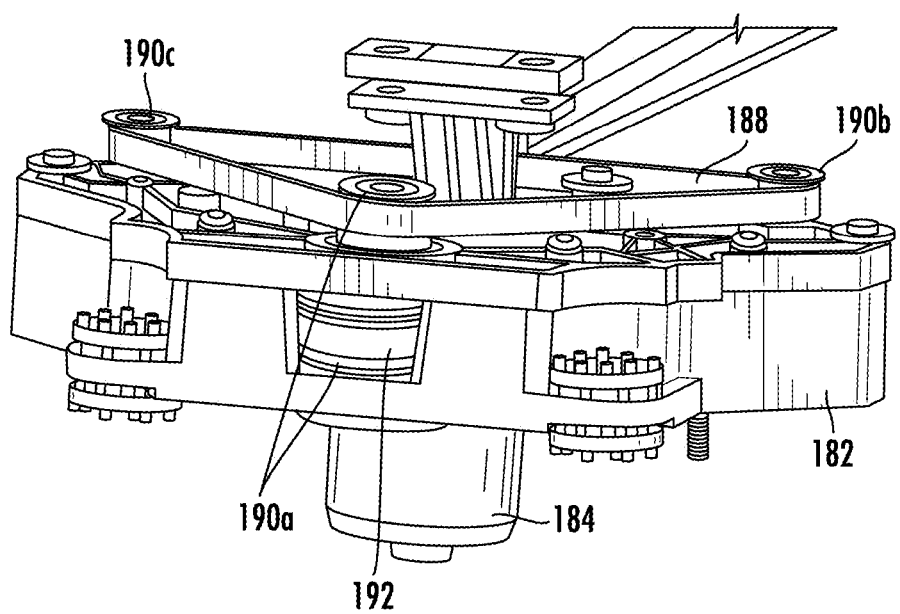
FIG. 12 illustrates another view of the drive module shown in FIG. 10 according to various embodiments described herein.

FIG. 8 illustrates a method of calculation of breaths per period according to various embodiments. The period is exemplified as a minute, but those having skill in the art will appreciate upon reading the present disclosure that other predetermined periods may be used. The breath detection module may calculate breathing rate on a buffer of the length of 60 seconds, although other periods may be used. As shown in FIG. 5, the whole buffer may be used to calculate breathing rate per minute. For example, breathing rate may be calculated when the buffer is full after 60 seconds, and then again after every 2 seconds based on new data acquired. Breathing rate may be calculated by detecting peaks in the collected signal. Peaks correspond to each inhale interval and are found at the maximum value in that interval. However, noise may be responsible for false peaks, thus some embodiments may include steps to take into consideration in order to remove such false peaks. FIG. 8 is one such example. In some embodiments, one or more filtering steps may be removed or wavelets may not be used in conjunction with peak detection. Returning to FIG. 8, breathing data is acquired 700. The breath detection module may then process the data using low pass filtering 702. The filter used for low pass filtering may comprise a FIR filter for example. The filter may have a predetermined kernel length and cutoff frequency. For example, the kernel length may be 11. An example cutoff frequency may be 2 Hz such that information below 2 Hz is kept. In some embodiments, a delay induced by filtering of the signal may be reduced by utilizing forward-backward filtering.

Peaks may be detected using wavelets 704. To reduce the number of false peaks, a wavelet transformation may be introduced as an additional step in peak detection. Wavelet transformation is used in Signal processing to remove noise from signals. Transformation is localized in both times and in frequency domain where Fourier transformation is localized in frequency. In a first step, peak detection may be performed on the buffer. Peak detection may be a first derivative function performed on the sine function of the input signal. Peaks corresponding to a maximum may be detected after the derivative function. In a second step, wavelet transformation may be introduced to the input signal. Wavelet transformation used in this approach includes four levels with 2 types of kernels (both low and high kernel). The input signal is convolved with level one low and high kernel. The result of that convolution is then convolved with second level low and high kernels and so forth until the last level. The result after fourth level low convolution may be used further in the methodology. In a third step, peak detection is performed as explained above with respect to the first step on the resulting signal after the second step. In a fourth step, a list of peaks is created using the results after the first step and the third step. In this step, the breath detection module compares peak indexes calculated in the first and third steps. The peak is valid if in an area around the current peak from the third step is peak detected in the first step. The peak closest to a peak detected in the third step may be considered to be valid and others may be discarded.

Peaks may also be filtered 706. For example, after peak detection is performed, peak filtering may be used to remove peaks that are close to each other and are a consequence of noise that was not filtered. Filtering may include removing peaks that are adjacent to each other based on a predetermined minimal distance between two peaks. For example, a minimal distance between two peaks may be considered to be 80 samples (at 100 Hz) which correspond to 0.8 seconds.

The breath detection module may calculate breathing rate at 708. In one example, the breathing rate may be calculated as a median value of the first derivative performed on peaks after peak filtering. Other methodologies of calculating breathing rate may also be used.

In various embodiments, the breathing rate calculation may not be calculated until sufficient breathing data for the predetermined period has been obtained, e.g., 1 minute, although in some embodiments, breathing rate may be initially extrapolated from fractions of the predetermined period.

FIGS. 9-12 illustrate various embodiments and views of an example drive system 100 for a sleep device configured to rotate a platform of a sleep device 140 including a breath detection system 1 as described herein.

The sleep device 140 may be similar to the sleep devices 1200, 1250 shown in FIGS. 2A & 2B and include a base 144. A bearing base 148 may be supported on the base 144 in a rotationally fixed position. For example, the bearing base 148 may be bolted to the base 144 or otherwise attached thereto. A bearing 146 couples between the bearing base 148 and the platform (see, e.g., platform 1202 in FIG. 2A) to allow rotational motion of the platform relative to the bearing base 148. The bearing 146 may include a thrust bearing, a lazy Susan bearing, a slide bearing, plain or journal bearing, a low friction surface, a low friction Teflon surface, or a low friction silicon surface, for example. The drive system 100 may be configured to rotate the platform in a horizontal plane, side-to-side. The rotation may be on a vertical axis that extends through the bearing 146. The platform may rotationally mount to the base 144 through the bearing 146 and thereon be rotatable over the base 144. In the illustrated embodiment, the platform mounts to a platform mount 170 that includes a bearing mount 172 and a drive mount 174. A central portion of the platform may attach to the bearing mount 172 using clamps or bolts or other attachment structures. The drive mount 174 may or may not attach to the platform at a position outward of the bearing mount 172, which may include a position adjacent to a periphery edge or end of the platform. The drive mount 174 motion transfer arm 176 extends between the bearing mount 172 and a drive belt attachment member 178 to transfer motion provided by a drive module 180 to the platform or bearing mount 172 in the illustrated configuration.

The drive module 180 includes a motor bracket 182 to which a motor 184 (see FIG. 12) is mounted. The drive module 180 may attach to or be integral with the base 144. Torque generated by the motor 184 is applied to a motor shaft 186, the rotation of which is utilized to translate a drive belt 188. The drive module 180 may include one or more pulleys 190 (see, e.g., FIG. 11) configured to support translation of the drive belt 188 as it is driven by the motor shaft 186. The motor shaft 186 may comprise or operatively couple to a pulley 190. For example, in the illustrated embodiment, the motor shaft 186 connects to pulley 190d such that the pulley 190d rotates with the motor shaft 186.

While any suitable motor 184 may be used, the motor 184 is preferably selected to provide smooth, low noise operation with high torque at low rpm that may be precisely controlled for both position and speed. For example, the motor 184 may be a 3-phase permanent magnet synchronous motor (PMSM), a 3-phase brushless DC motor (BLDC), and the like which may be driven by sinusoidal currents. For controlling speed and position of the motor 184, a motor driver may synthesize three independent sinusoidal voltages with controllable frequency and amplitude for each phase. The synthesized voltages may have a constant phase offset of 120°, which reflects the position offset of three motor windings. The motor driver may comprise three half-bridges, one for each of the three phases, which generate three independent sinusoidal voltages. Each half-bridge may comprise two MOSFET transistors acting like low resistance electronic switches. By applying two mutually inverted pulse-width modulated (PWM) signals on those switches, the average voltage output from half-bridge may be set anywhere from 0 V to 12 V DC. These voltages are connected to the motor terminals in order to create sinusoidal currents in windings of the motor 184 and appropriate magnetic flux in a motor stator.

The use of a BLDC motor is advantageous as it enables direct control of both amplitude and frequency without the need for an additional motor or additional gears to manipulate amplitude. The reduction or elimination of gears may enable quieter operation, which is an advantage in this application. It also reduces the number of moving mechanical parts, which may lead to an improvement in robustness. The use of a brushless motor may also extend the life of the motor by eliminating brush wear. Typical inductive motors have an optimum RPM and achieve lower speeds with gearing. Applications with continuous change of direction tend to be difficult for these motors. An advantage of the BLDC motor is that it operates well at a wide range of frequencies (RPMs) and has high torque at low RPMs, which facilitate the rapid change of direction needed by this application.

In order to achieve silent operation, the PWM frequency, the frequency at which the half-bridges are turned on and off, may be set above 20 kHz and preferably around 40 kHz. The PWM frequency is unrelated to the frequency at which the motor 184 rotates the platform. Required PWM signals for a driver stage may be generated by a microcontroller (MCU) based on a control algorithm. The control algorithm may determine the desired amplitude and frequency of motion based on input from a subject motion sensing device, a subject noise sensing device, a subject vital sign sensing device such as a sensor for heart rate, breathing, oxygenation and the like as discussed elsewhere herein and in U.S. patent application Ser. No. 15/055,077, filed Feb. 26, 2016. An open-loop control method which relies on the ability of the motor rotor to stay locked with the stator magnetic flux may be used such that control of the position and rotational speed of the motor shaft 186, may be achieved by control of the three winding currents alone.

The drive system 100 may include a control system operable to control movements of the platform. The control system may be as described above with respect to control system 2216 (FIG. 3). For example, the control system may include a control board 168 configured to control amplitude and frequency of the platform movements by modulating operation of the motor 184. The control system may include or communicate with a user interface to receive inputs and control instructions and/or output information regarding the operation of the system or a subject. The control system may be configured to collect data from one or more sensors and control output of motion and/or sound in response to the collected data. In various embodiments, the control system may be similar to that described in as described in U.S. patent application Ser. No. 14/448,679, filed Apr. 31, 2014, or U.S. patent application Ser. No. 15/055,077, filed Feb. 26, 2016. In some embodiments, the control system integrates with or is separate from the control system described above with respect to the breath detection system or breath detection module.

As introduced above, output of the motor 184 is transferred to drive belt 188, the translation of which further transfers the motor output to the platform via coupling of the drive belt attachment member 178 to the drive belt 188. The drive belt attachment member 178 may couple to the belt 188 in any suitable manner. In the illustrated embodiment, the drive belt attachment member 178 attaches to the belt 188 via clamping to the drive belt 188.

The drive belt 188 may comprise a belt or chain. When a chain is used one or more pulleys 190 may include spaced apart teeth that insert within gaps between pins in the chain to assist in transferring power to the chain. In the illustrated embodiment, the drive belt 188 comprises a belt having teeth or ribs formed along a side thereof that engage between corresponding teeth or rib contours on one or more pulleys 190 that the drive belt 188 rotates when translated by the motor 184. In another embodiment, the drive belt 188 may include flat sides.

As introduced above, the drive module 180 may include one or more pulleys 190 that support the movement of the drive belt 188. While various arrangements of pulleys 190 may be used, in the illustrated embodiment the motor shaft 186 couples to a transfer belt 192 via pulley 190d. Translation of the transfer belt 192 is transmitted to a transfer pulley 190a to drive rotation of the same. Rotation of the transfer pulley 190a is translated to the drive belt 180, the translation of which is supported by the transfer pulley 190a and idler pulleys 190b, 190c. Thus, rotation of the motor shaft 186 translates transfer belt 192 to rotate the transfer pulley 190a. Rotation of the transfer pulley 190a translates drive belt 188, and translation of drive belt 188 rotates idler pulleys and imparts corresponding lateral movement at the drive belt attachment member 178. The lateral movement at the drive belt attachment member 178 levers the platform or platform mount 170 on the bearing 146 to rotate the platform over the base 144. Corresponding reversal of the motor 184 drives lateral movement of the drive belt attachment member 178 in the opposite direction to provide oscillating movement of the platform. The illustrated transfer pulley 190a includes a lower portion that couples to the transfer belt 192 and an upper portion that couples to the drive belt 188. In other embodiments, the transfer pulley 190a may couple to the transfer belt 192 along an upper portion and couple to the drive belt 188 along a lower portion. In various embodiments, additional belts and/or pulleys 190 may be used to modify location or direction of belt movements. The drive module 180 may optionally include a tensioner 194 that engages the drive belt 188 to allow adjustment of tension on drive belt 188.

In some embodiments, the platform mount 170 may extend outwardly of the bearing mount 172 to attach to the platform at other locations outward of the central portion of the platform, such as adjacent to a perimeter of the platform for example. In some embodiments, the bearing mount 172 comprises one or more frame members that extend from the bearing mount 172 that attach to or otherwise provide support for the platform at peripheral locations beneath the platform.

In another embodiment, the motor output may be directly transmitted to the bearing mount 172. For example, a motor shaft 186 may mechanically or frictionally engage a side or edge of the bearing mount 172 to drive rotation on the bearing 146. In one example, the motor shaft 186 includes teeth that engage corresponding teeth or gears associated with the bearing mount 172 to translate the torque generated by the motor to rotation of the platform. In another embodiment, the drive system 100 includes a linear motor that pushes and pulls the motion transfer arm 176 to rotate the platform.

In some embodiments, the breath detection system or breath detection module and components thereof described herein is utilized in a sleep device including one or more additional sensors for measuring additional parameters. For example, the breath detection system or breath detection module may be incorporated in an infant calming/sleep aid device as described in U.S. patent application Ser. No. 14/448,679, filed Apr. 31, 2014, or U.S. patent application Ser. No. 15/055,077, filed Feb. 26, 2016, and include a control system for determining a behavior state of the infant, e.g., motion detection, sound detection, and/or detection of other parameters, and initiating a response including rotation of the platform in an oscillating manner to soothe or induce sleep. The sleep device may include a processing system similar to processing system 1300 described above with respect to FIG. 3. In one example, drive system 100 or another drive system configuration may drive oscillatory motion at 0.5-1.5 cycles per second (cps) of about 2" excursions, but if the baby is fussy the device responds by delivering a smaller excursion (e.g. <1.3") at a faster rate (about 2-4.5 cps). This fast and small motion may deliver the specific degree of rapid acceleration-deceleration force to the semicircular canals in the vestibular mechanism of the inner ear to activate the calming reflex. The reciprocating motion may have a maximum amplitude of less than 1.3 inches during the rapid phase of motion (~2-4.5 cps), further ensuring safety of the infant. In some embodiments, sound may also be output from speakers to soothe the infant. In one example, in response to detection of infant distress, both vigorous motion of the platform and a loud sound can be provided. For example, providing motion of the platform at a frequency greater than 0.5 Hz and an amplitude of 1 inch, along with sound having an intensity of at least 65 dB, may provide appropriate stimulation of the infant. Of course, other amounts of stimulation are also envisioned. In another or a further example, at a baseline, sound output may produce a low-pitch, rumbling sound at about 65 dB to about 74 dB. If the behavior state of the infant becomes more distressed, a more high pitched audio track may be output. In a further example, the higher pitched audio track may be output at a louder volume of about 75 dB to about 95 dB for a limited amount of time.

Figure 13:
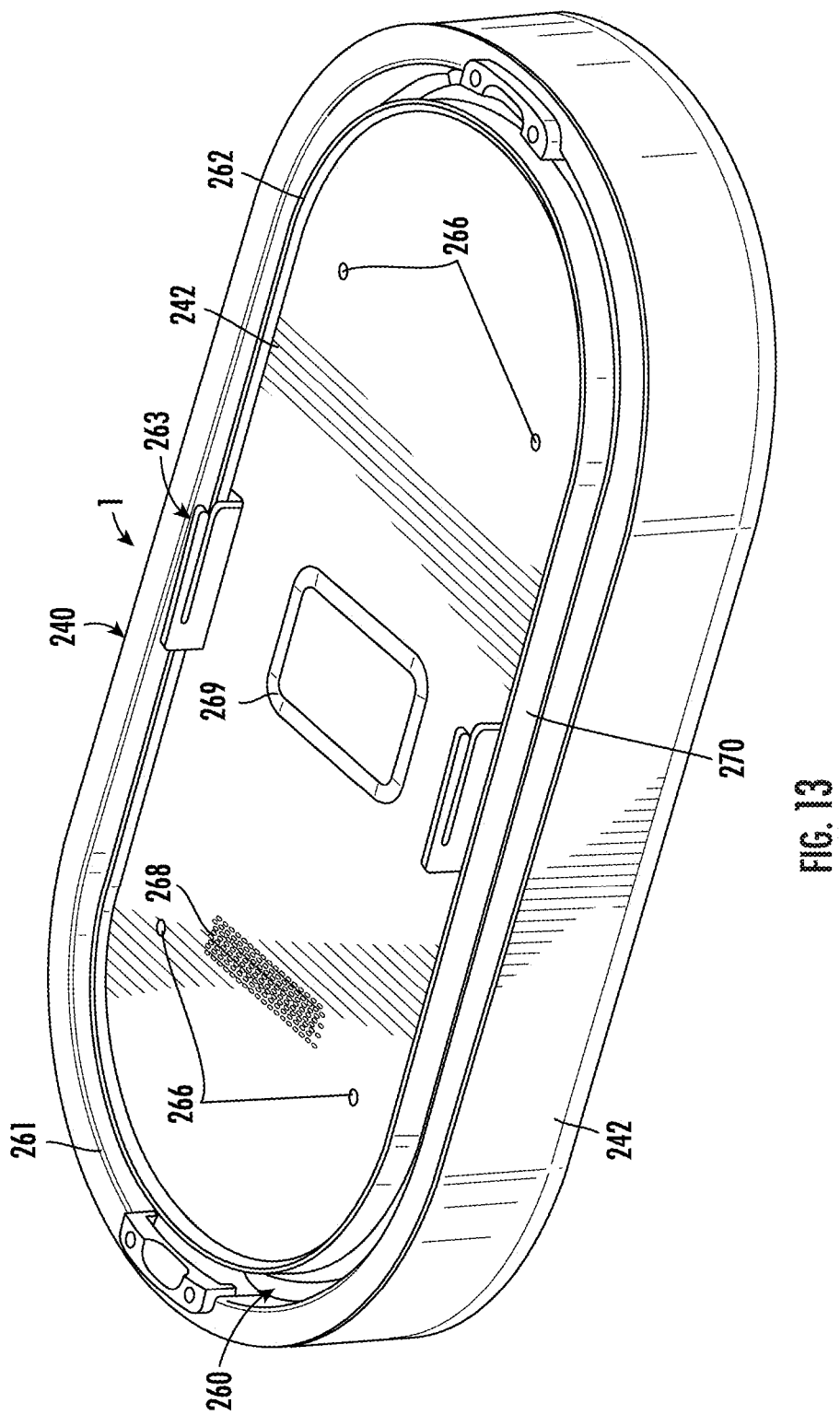
FIG. 13 is a perspective view of a configuration of a weight detection system for a sleep device according to various embodiments described herein.
Figure 14:
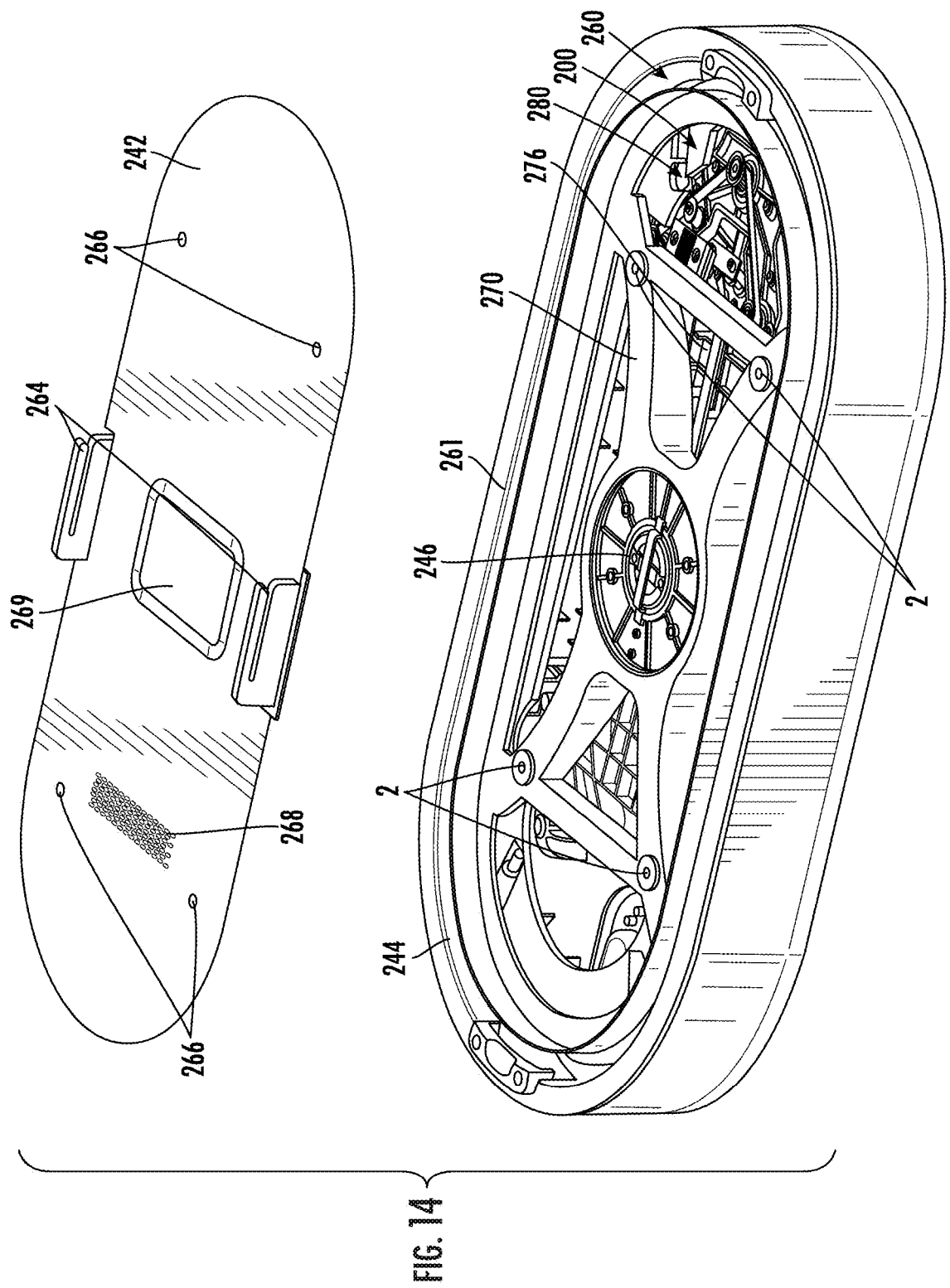
FIG. 14 illustrates an exploded view in perspective of the weight detection system for a sleep device show in FIG. 13 with the platform separated from the base according to various embodiments described herein.
Figure 15:
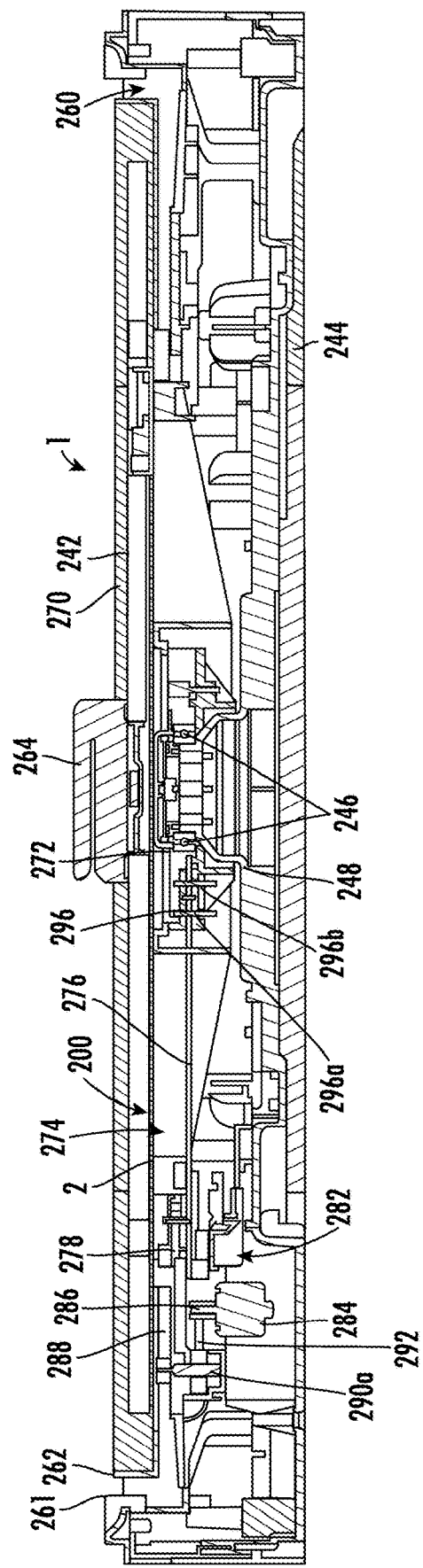
FIG. 15 is a longitudinal cross-section view of the weight detection system for a sleep device show in FIG. 13 according to various embodiments described herein.
Figure 16:
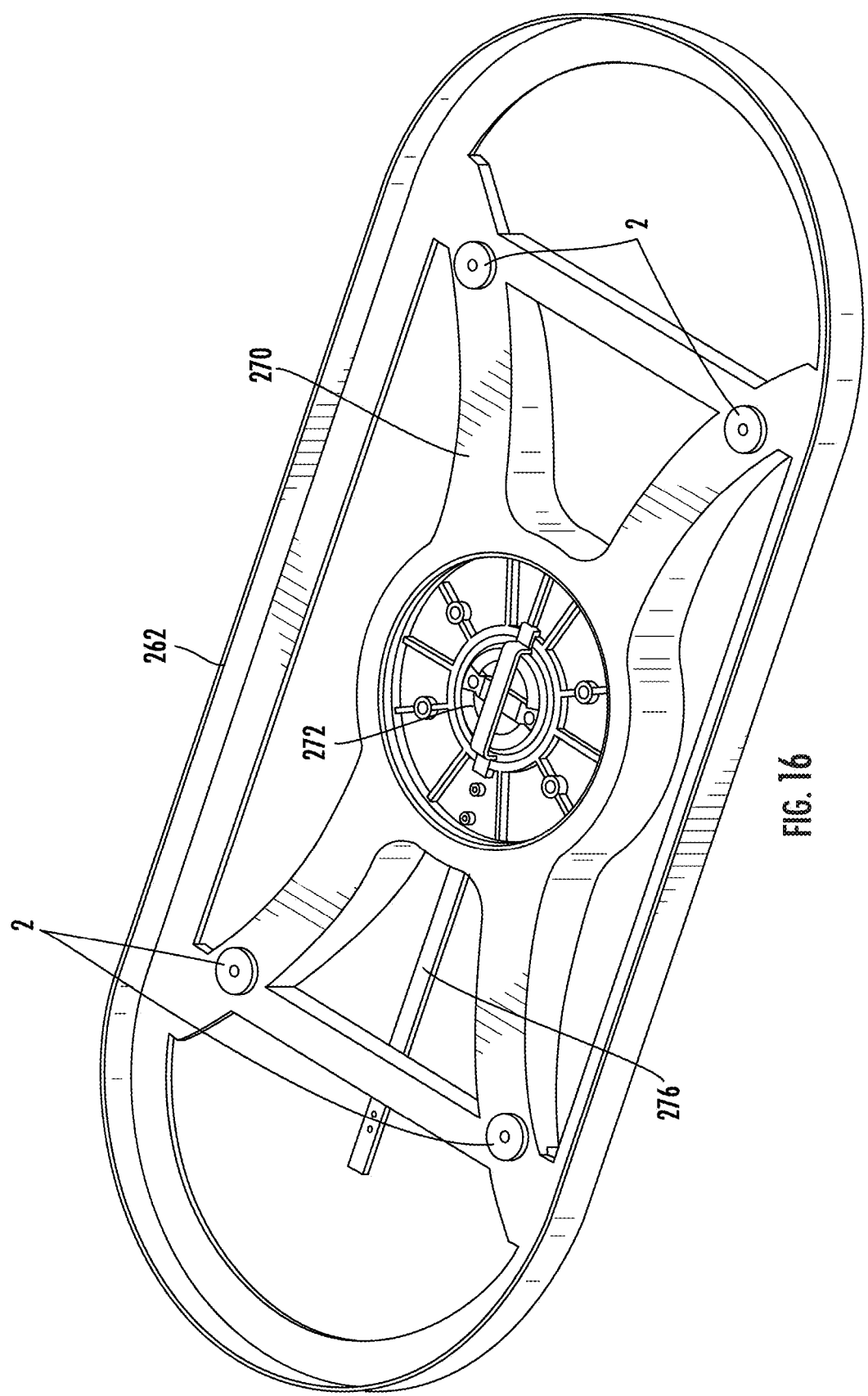
FIG. 16 is an isolated view in perspective of the platform mount depicted in FIG. 14 and FIG. 15 according to various embodiments described herein.
Figure 17:
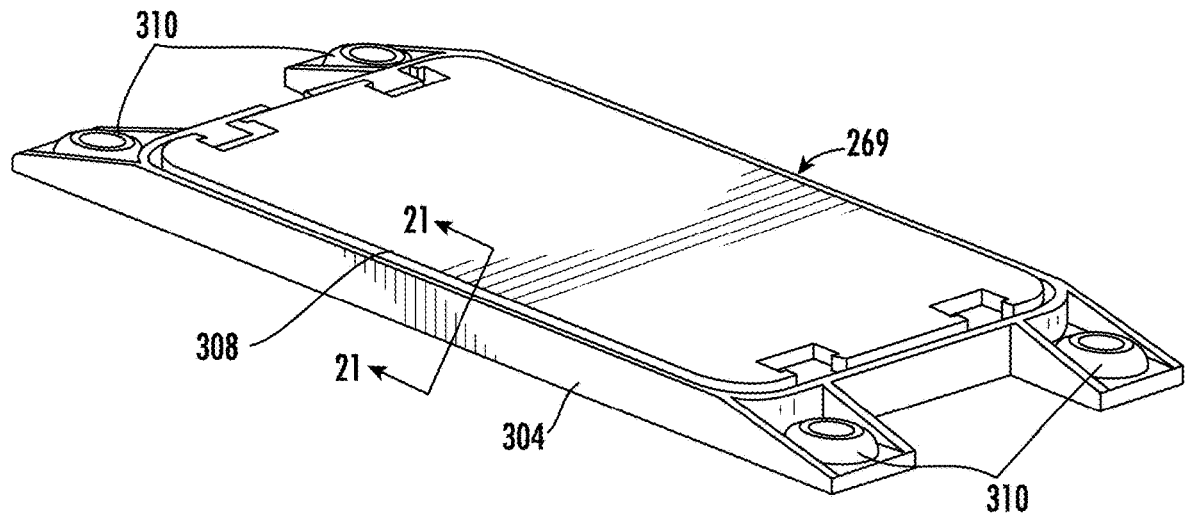
FIG. 17 is a perspective view of a breath sensor according to various embodiments described herein.
Figure 18:
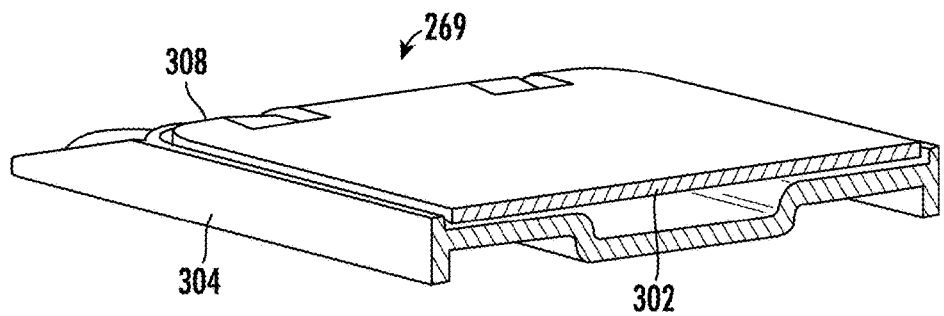
FIG. 18 is a cross-section view of the breath sensor shown in FIG. 17 taken along section 21 in FIG. 17 according to various embodiments described herein.
Figure 19:
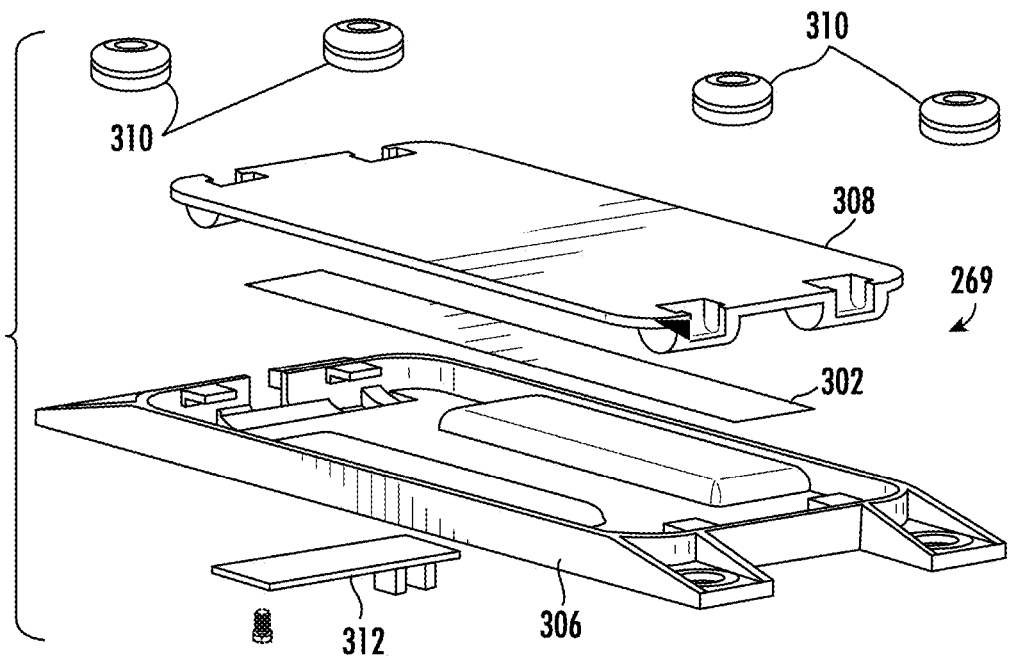
FIG. 19 is an exploded view of the breath sensor shown in FIG. 17 according to various embodiments described herein.
Figure 20:
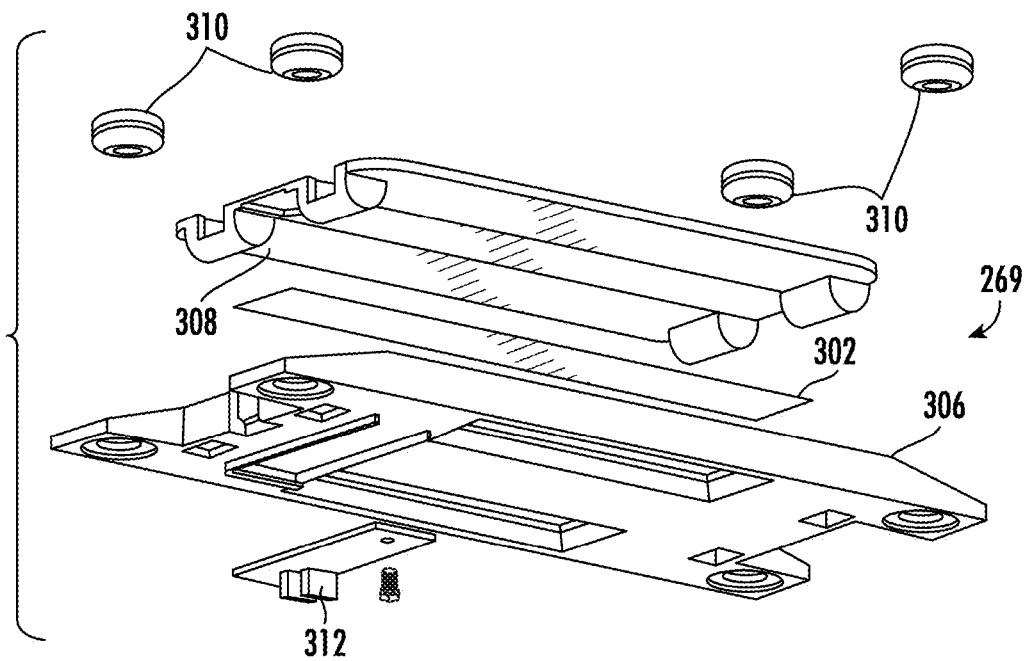
FIG. 20 is an exploded view of the breath sensor shown in FIG. 17 according to various embodiments described herein.

FIGS. 13-16 illustrate another configuration of a sleep device 240 incorporating the breath detection system 1. A base 244, platform 242, and related features are shown in FIGS. 13-15; however, various sleep device configurations may be used.

The breath detection system 1 may include or be configured to operate in conjunction with a base 244 and/or a platform 242 and one or more breath sensors 269. Breath sensors 269 may include any suitable breath sensor, such as those described herein. The breath sensor 269 may be configured to detect breathing, heartbeat, and/or motion. The breath sensor 269 may be a part of or configured to operably communicate with a control system as described herein and/or a breath detection module of a control system. Breath sensor may be a biometric sensor of a sensor device as described herein, such as sensor device 2, 2002 (e.g., FIGS. 1C & 3).

The platform 242 couples to a platform mount 270 at one or more attachment points 266. In the illustrated example, one or more weight sensors 2 are positioned at attachment points 266 to locate between the platform 242 and platform mount 270. However, in other embodiments, the platform 242 may attach to the platform mount 270 without weight sensors 2 positioned at attachment points 266 or at other attachment points. The one or more weight sensors 2 may include load cells or other weight sensor 2 configuration having a slot through or adjacent to the sensor 2 through which a screw, bolt, or other attachment structure may be extended to mount the platform 242 to the platform mount 270.

Weight sensors 2 may be configured to collect weight data for weight tracking and/or weight analysis. For example, the weight sensors 2 may be configured to measure weight of a subject positioned on the platform 242. The weight sensor 2 may be configured to collect weight data continuously, periodically, at predetermined intervals, upon receiving an instruction to collect weight data, and/or upon the occurrence of an event, such as when a subject is placed on the platform 242. In one embodiment, a user may define or schedule when weight measurements are to be taken or input an instruction via a user interface to collect weight data in a manner as described above. The platform 242 may be mounted to the platform mount 270 at the attachment points 266 such that the platform compresses against the weight sensors 2. In one embodiment, weight sensors 2 and/or a control system may calibrate weight sensors 2, e.g., upon startup to zero out the weight of the platform 242.

The platform 242 may be rotatable over a bearing base 248 fixed to the base 242, which may also include the bearing base 248. Rotation may be on a vertical axis that extends through a bearing 246 on which the platform 242 is rotatable relative to the base 244. In some embodiment, the platform 242 may be configured to move in other or additional motion patterns, such as any described herein. As depicted, the platform 242 mounts to a platform mount 270 that includes a bearing mount 272 for rotatably mounting over the base 244 and a drive mount 274 for mounting to a drive system 200. A central portion of the platform 242 may attach to the bearing mount 272 using clamps or bolts or other attachment structures.

The sleep device includes a drive system 200 configured to selectively move the platform 242. The drive system 200 may be configured in a manner similar to that described above with respect to drive system 100 (see FIGS. 9-12) wherein similar features are identified by similar numbers. For example, the drive system 200 includes a drive module 280 comprising a motor 284 housed in a motor bracket 282. Motor output rotates a motor shaft 286 that drives corresponding rotation of transfer pulley 290a via a transfer belt 292. Rotation of transfer pulley 290a is translated to a drive belt 288, which is coupled to the platform 244 via the drive mount 274. The drive mount 274 includes a drive belt attachment member 278 comprising a clamp that clamps the drive belt 288 to couple to the movements of the drive belt 288. The drive belt attachment member 278 attaches to motion traction arm 176 or directly to the platform 242 or platform mount 270. The drive mount 274 in the illustrated embodiment includes a motion transfer arm 276 that extends between the bearing mount 272 and a drive belt attachment member 278 to transfer motion provided by a drive module 280 to the platform 242 and/or bearing mount 272. In the illustrated embodiment, the motion transfer arm 276 couples to the platform mount 270 and/or platform 242 at a transfer arm coupling 296. While other coupling configurations may be used, the transfer arm coupling 296 includes an upper clamp portion 296a and a lower clamp portion 296b configured to clamp the motion transfer arm 276 to couple the platform mount 270 to transfer arm 276. In another embodiment, the motion transfer arm 276 is retained by pins, bolts, or is integral with the platform mount 278 or platform. It should be appreciated that other configurations may be used to couple to the motion of the drive belt 288, e.g., the platform mount 270 or platform 242 may directly couple to the drive belt 288.

To provide room for the platform 242 to move, a gap region 260 may be provided between an interior facing side 261 of the base 244 and an outer side or rim 262 of the platform mount 270, although in other embodiments, the gap region 261 may be provided between the interior facing side 261 of the base 244 and an outer side of the platform 242. In the illustrated embodiment, the rim 262 extends upward to define an area to receive the platform 242 such that the platform 242 recesses below an upper extent of the rim 262.

The rim 262 may assist in retaining a mattress (not shown) positioned on the platform 242 during motion of the platform 242.

As introduced above, the breath detection system 1 so arranged with the platform 242 and/or bearing mount 272 described with respect to FIGS. 13-16 may be incorporated in sleep devices 240 having different drive systems and/or configurations without drive systems. In another embodiment, the breath detection system 1 is incorporated with respect to a platform and drive system configured to move in another manner, e.g., up and down; a lateral, longitudinal, or diagonally directed wave motion; a rocking motion; lateral side-to-side motion on a horizontal plane; a head-to-toe motion on a plane on a horizontal plane; and/or a tilting motion on an axis of rotation that extends through or parallel to the major plane of the platform, such as laterally to tilt a first longitudinal end of the platform 242 upward while tilting a second longitudinal end downward or longitudinally to tilt a first lateral side of the platform upward while tilting a second lateral side downward. In one example, the rotation or tilt axis extends a long a horizontal plane through or relative to a central longitudinal or lateral division or bisection of the platform 242. Such motions may be selected based on data collected by sensors and analysis thereof as described herein.

In some embodiments, the breath detection system 1 may include a control system and additional sensors as described above with respect to FIG. 3 and elsewhere herein. For example, the control system may include an analysis module and communicate with and provide outputs to a user interface and/or data storage device. The control system may also include or interface with another control system operable to control a motor that drives motion of the platform 242.

In one embodiment, drive system 200 may be incorporated in an infant calming/sleep aid device as described in U.S. patent application Ser. No. 14/448,679, filed Apr. 31, 2014, or U.S. patent application Ser. No. 15/055,077, filed Feb. 26, 2016, and include a control system for determining a behavior state of the infant, e.g., motion detection, sound detection, and/or detection of other parameters, and initiating a response including rotation of the platform 242 in an oscillating manner based on analysis of the measured data to soothe or induce sleep. For example, the drive system 200 may drive oscillatory motion at 0.5-1.5 cycles per second (cps) of about 2" excursions, but if the baby is fussy the device responds by delivering a smaller excursion (e.g. <1.3") at a faster rate (about 2-4.5 cps). This fast and small motion may deliver the specific degree of rapid acceleration-deceleration force to the semicircular canals in the vestibular mechanism of the inner ear to activate the calming reflex. The reciprocating motion may have a maximum amplitude of less than 1 inch during the rapid phase of motion (−2-4.5 cps), further ensuring safety of the infant. In some embodiments, sound may also be output from speakers to soothe the infant. In one example, in response to detection of infant distress, both vigorous motion of the platform 242 and a loud sound can be provided. For example, providing motion of the platform 242 at a frequency greater than 0.5 Hz and an amplitude that is greater than 1 inch, along with sound having an intensity of at least 65 dB, may provide appropriate stimulation of the infant. Of course, other amounts of stimulation are also envisioned. In another or a further example, at a baseline, sound output may produce a low-pitch, rumbling sound at about 65 dB to about 74 dB. If the behavior state of the infant becomes more distressed, the a more high pitched audio track may be output. In a further example, the higher pitched audio track may be output at a louder volume of about 75 dB to about 95 dB for a limited duration.

The platform 242 also includes an optional attachment mechanism 263 for attachment of a sleep sack configured to secure an infant to the platform in a manner described in U.S. patent application Ser. No. 14/448,679, filed Apr. 31, 2014, or U.S. patent application Ser. No. 15/055,077, filed Feb. 26, 2016. In the illustrated embodiment, the attachment mechanism 263 comprises two attachment members 264. The attachment members 264 include clips positioned at lateral sides of the platform 242. Attachment mechanism, such as those illustrated, may similarly be incorporated with the other embodiments of a platform of a sleep device described herein.

The sleep device 240 or breath detection system 1 may include one or more additional sensors for measuring additional physiological parameters, such as biometric sensors, e.g., weight sensors 2, introduced above. Such additional sensors may be associated with a sensor system or control system such as described in U.S. patent application Ser. No. 14/448,679, filed Apr. 31, 2014, or U.S. patent application Ser. No. 15/055,077, filed Feb. 26, 2016, or that integrates data collected from the breath sensor 269. In the illustrated embodiment, the platform 242 also incorporates one or more optional speakers 268 for outputting audio. The audio may comprise tracks selected by a control system or control system thereof based on inputs and/or analysis of cries, motions, or other data related to the infant collected by sensors positioned to detect parameters of the infant. The sensors may include a pressure sensor (e.g., pressure mat), video sensor (e.g., to detect movement and/or collect size data), mmWave or UWB radars, or motion sensors.

In one embodiment, the breath sensor 269 comprises one or more motion sensors comprising one or more piezoelectric elements. Piezoelectric elements generate charge voltage in response to mechanical stress, as well as mechanical strain in response to an applied electrical field. Breath sensors 269 including piezoelectric elements may be configured to detect pressure, force, strain, or acceleration changes, which may include vibrations.

Piezoelectric elements may detect vibrations, through or along a solid or gas by transducing the resulting mechanical stress into a voltage signal. In various embodiments, the signal may be transmitted for analysis by one or more system modules described herein. For example, a breath sensor 269 including a piezoelectric element may function as a biometric sensor to detect vibrations transduced to electrical signals for analysis by a heartbeat detection module and/or breath detection module, which may include a control system or sensor control system as described herein. Piezoelectric elements may include or communicate with a processor and/or storage medium storing analysis instructions executable by the processor for analysis of current or voltage generated by the sensor.

In one example, a breath sensor 269 comprising a piezoelectric element includes one or more piezoelectric strips. The strip material may be suspended in some implementations. Strip sensors may be attached to surfaces such that movement of the surfaces stresses or strains the sensor. Strip sensors may be positioned between two surfaces such that changes in forces transmitted between the two surfaces are detected by the sensor. Strip sensors may be position in a sealed gas volume or within a solid such that vibrations transmitted along surrounding material are detected by the sensor via changes in pressure. The strip sensors may be suspended to isolate the sensors from motion of a movable platform. A piezoelectric element may be positioned at an appropriate location relative to and within an appropriate distance from the subject to detect motion of the subject, such as vertical motion or other directional motion and/or an associated pressure, force, or vibration. In one example, multiple piezoelectric strip sensors may be used at various locations.

In one example, a piezoelectric element comprises one or more piezoelectric ceramic materials. Ceramic piezoelectric elements may be positioned and/or configured as described with respect to piezoelectric strip materials. In some embodiments, piezoelectric ceramics may be attached to surfaces directly or indirectly in contact with a subject such that movement of the surfaces caused by the subject stresses or strains the sensor. For example, one or more ceramic piezoelectric sensors may be attached along a platform configured to support a subject. The sensors may be attached to detect vibrations propagated along the platform. The piezoelectric element may be a piezoceramic wafer or other piezoceramic material mass. The piezoelectric element may be coupled to a processor configured to collect electrical signal transduced by the piezoelectric element from the detected vibrations. The processor may include various circuit components such as an analog to digital converter. The processor may include various signal processors that may condition or filter the signal. The processor t may be provided on a circuit board which may electrically couple to the piezoelectric ceramic element. The processor may be attached to a vibration substate, platform, on a sleep device, or may be positioned elsewhere, e.g., remote, to receive the electrical signal.

In various embodiments, vibrations of a subject's back are transmitted through a mattress into a vibration substrate associated with the piezoelectric element. The back of the subject will vibrate due to breathing, heartbeat, cry, etc. as it is physiologically not possible for it not to. Thus, a piezoelectric element of a breath sensor 249 may be positioned underneath a subject. For example, the piezoelectric element may be embedded in a mat, mattress, sleep garment, infant sleep sack, or attached to a platform upon which the subject is to be supported. The piezoelectric element may be configured to be sensitive enough that intervening media, such as a mattress, does not kill the signal. The vibration substate may operate in a manner similar to a microphone membrane, but with respect to transmitted mechanical vibrations, vibrating due to the movement of the subject. In various embodiments, when the piezoelectric element is attached to the vibration substrate, the location of the subject with respect to the piezoelectric element is not material. While a mattress, which may include a mat or pad, may dampen the vibration signal, the sensitivity of the piezoelectric element is such that a dampened vibration may be detected and processed to identify breathing and/or heartbeat related data of the subject. The material of the vibration substrate must be suitable for propagating vibrations, and may include metal, plastics, hardwoods, or ceramics, for example.

In some embodiments, the piezoelectric element of a breath sensor 249 may be positioned underneath, and firmly attached to, the underside of the platform the subject is located on. The piezoelectric element may be directly or indirectly adhered to a surface of the platform configured to be the upper or lower side of the platform relative to the subject. As noted above, a piezoelectric element may comprise a strip sensor. In some such embodiments, strip sensors may preferably be positioned along the platform at a location corresponding to the back of the subject when supported on the platform.

FIGS. 17-21 illustrate various views of two embodiments of a breath sensor 269 for a sleep device. The exemplary breath sensors 269 include tray design configurations for attachment to a platform of a sleep device, but other design configurations may be used. The breath sensor 269 attaches to the platform and is positioned to underlay a mattress and a subject positioned thereon. The breath sensor 269 may be posited within a recess and position approximately flush or slightly above a plane defined by a surrounding upper surface of the platform. The breath sensor 269 in this embodiment, may include a piezoelectric element 302 comprising a strip or other configuration. Force, strain, or vibrations applied along the piezoelectric element 302 may be converted to an electric signal for detection of breathing of a subject positioned on the platform. As noted above, the breath sensor 269 may also be used to detect heart beat and motion.

With particular reference to the embodiment shown in FIGS. 17-20, the piezoelectric element 302 may be housed within a sensor housing 304 having a base 306 and a cover 308. The base 306 may attach to a platform through one or more gromet 310 configured to dampen propagation of vibrations from the platform to the housing 304. The piezoelectric element 302 may be positioned to detect force, strain, or vibrations, from above the platform to generate an electric signal for detection of breathing of a subject positioned on the platform. A data signal port 312 electrically couples to the piezoelectric element 302 to receive and transmit the electrical signal, wired or wirelessly, to a control system or breath detection module as described herein. The piezoelectric element 302 may be suspended within the housing, attached to an upper wall of the cover (as shown), or positioned within a sealed portion of the housing 304 to detect pressure changes, force, or strain. In various embodiments, the sensor housing 304 may be considered a vibration substrate for receiving vibrations originating from the subject positioned above the sensor housing 304.

Figure 21:
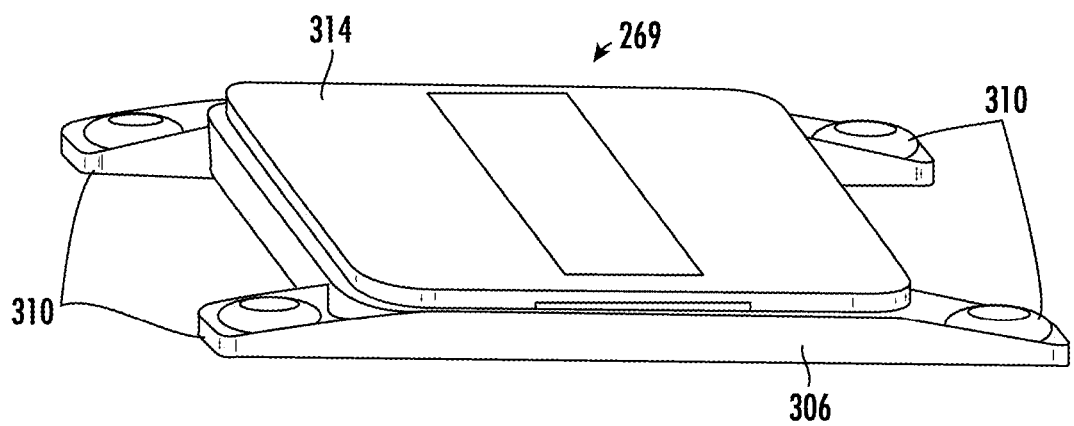
FIG. 21 is a perspective view of a breath sensor according to various embodiments described herein.

FIG. 21 illustrates another embodiment of the breath sensor 269 including a piezoelectric element 302 positioned on a material configured to isolate the piezoelectric element 302 from vibrations from a platform upon which it mounts. As shown, the piezoelectric element 302 positions on a foam pad 314 that rests on a base 306. The foam pad 314 may extend to rest flush with the base 306 along its underside. In another embodiment, one or more cavities are positioned between the underside of the foam pad 314 and the base 306. In another embodiment, the piezoelectric element 302 positions on a firm surface and one or more sides of the element 302 are surrounded and positioned adjacent to the foam pad 314. The foam pad 314 may extend along sides of the piezoelectric element 302 to damped vibrations propagated along a mattress in which the breath sensor 269 underlies to further focus detection to portions of the mattress above the piezoelectric element 302. In one embodiment, the foam pad 314 is supported on a cover that covers the base 306. The base 306 may attach to the platform through one or more gromet 310 configured to dampen propagation of vibrations from the platform to the piezoelectric element 302. The breath sensor 269 may include a data signal port 312, which may be similar to data signal port 312 described with respect to FIGS. 17-20, that electrically couples to the piezoelectric element 302 to receive and transmit the electrical signal, wired or wirelessly, to a control system or breath detection module as described herein. In various embodiments, the breath sensor 249 may be utilized in a sleep device as described herein. In use, a subject may be positioned on a mattress resting on the platform of the sleep device in the conventional manner such that a height dimension of the subject extends along the longitudinal axis of the mattress. As noted above, the subject may be secured in position on the mattress relative to the platform with straps or clips within a sleep sack or other harnessing device.

FIG. 22 shows an example of the base 244 and platform 242 of a sleep device 340 including a breath sensor 269 according to various embodiments described herein. The breath sensor 269 includes a piezoelectric element 302 and base 306 similar to that described with respect to FIGS. 17-21. The piezoelectric element 302 may be positioned on or between a foam pad 314 in a manner described above with respect to FIG. 21 and its variations. Gromets 310 may also be used to dampen vibrations. The sleep device 340 may be similar to sleep device 240 (FIG. 13) and be configured with a movable platform 249.

In the embodiment illustrated in FIG. 21, the piezoelectric element 302 comprises a strip that extends laterally or transverse to the longitudinal expanse of a platform to correspondingly underlie a mattress or pad positioned on the platform. The embodiment illustrated in FIGS. 17-20, the piezoelectric element 302 comprises a strip that extends longitudinally or about parallel to the longitudinal expanse of a platform to correspondingly underlie a mattress or pad positioned on the platform. Thus, a piezoelectric element 302 comprising a strip may be configured to position under a subject on the platform, preferably beneath the torso. While various orientations may be used, the piezoelectric element 302 may be orientated transverse or corresponding to the height dimension of the subject. FIG. 22 illustrates an example platform 242 and platform mount 270 supported by a base 244 wherein a breath sensor 269 is positioned thereon and includes a piezoelectric element 302 that extends longitudinally along the longitudinal axis of the platform 242. The platform 244 may be configured to move as described herein. The configuration shown in FIG. 22 may also include a drive system, such a drive system similar to that described herein. In some examples of the breath sensor 249 of FIGS. 17-20, the piezoelectric element 302 may be positioned transversely or at other angles.

As introduced above, the piezoelectric element may by attached to a vibration substrate in vibratory communication with the subject. Vibratory communication with the subject is intended to refer to mechanical vibratory contact between the infant, the vibration substrate, and intervening mediums. The vibratory contact is such that vibrations from the infant may be transmitted to the vibration substate from the subject through intervening media, if present. The piezoelectric element may be attached to one of the vibration mediums, which may be referred to herein as the vibration substrate, such that the mechanical vibrations propagated through the intervening vibration mediums may likewise transmit along the vibration substrate such that the deflections of the vibration substrate are detected by the piezoelectric element attached to the vibration substrate. The intervening media will typically be solid materials along which vibrations may be propagated and transmitted to the piezoelectric element. For example, mechanical vibrations from a subject positioned on a mattress may be transmitted through the interviewing media of the mattress, bed clothes, platform or component thereof, and the like to the piezoelectric element. Thus, intervening media may be considered vibration media that contact or otherwise couple between the infant and the piezoelectric element such that mechanical vibrations may be transmitted from the infant to the piezoelectric element through the intervening media. As noted above, some embodiments may include strip sensors position in a sealed gas volume or within a solid such that vibrations transmitted along surrounding material are detected by the sensor via changes in pressure.

In some embodiments, the vibration substrate is a mattress and the piezoelectric element is attached to the mattress at a location within the mattress or along a surface thereof. A mattress may include a pad or mat. In one embodiment, the vibration substrate comprises a panel configured to be positioned beneath the subject, between a mattress or other supporting surface and the subject, or beneath both the subject and the mattress or other supporting surface. In some embodiments, the vibration substrate is a platform or component thereof for supporting a mattress, such as a bed frame or platform configured to undergo motion. The piezoelectric element may be attached to the platform at a location within the platform or along a surface thereof.

Figure 23A:
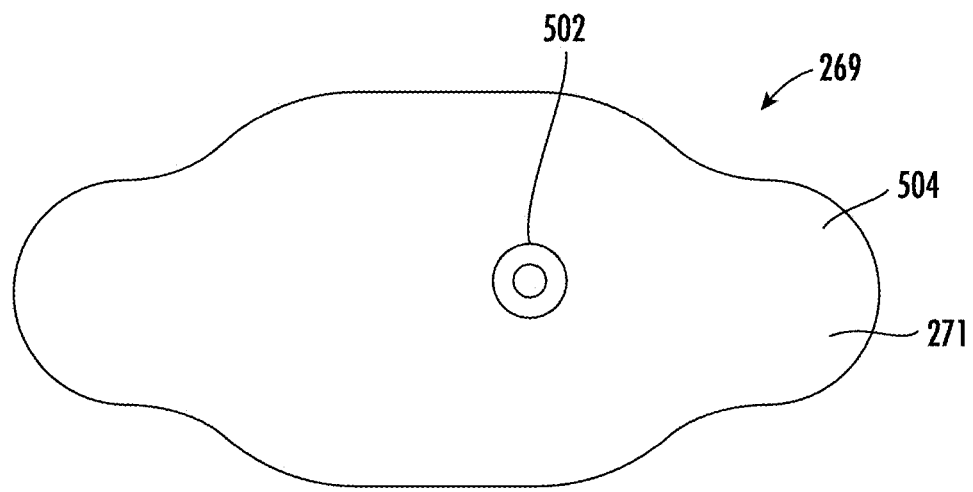
FIG. 23A is a bottom view of a vibration substrate including a breath sensor for positioning beneath a mattress according to various embodiments described herein.
Figure 23B:
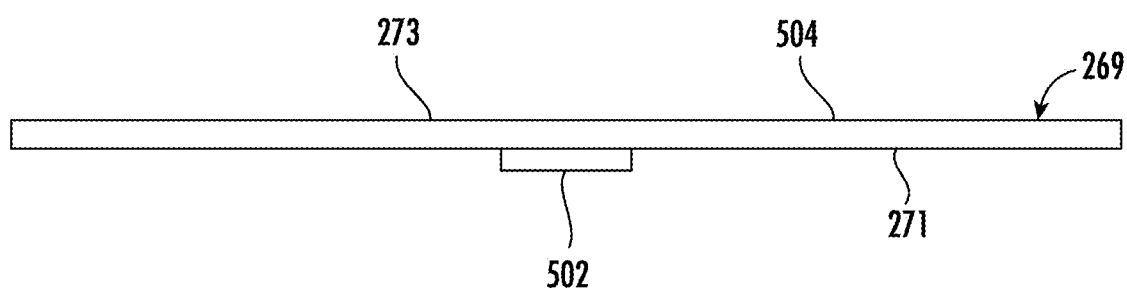
FIG. 23B is a side view of the vibration substrate and breath sensor shown in FIG. 23A according to various embodiments described herein.

In the embodiment illustrated in FIGS. 23A-23B, a breath sensor 269 includes a piezoelectric element comprising a piezoceramic element 502 attached to a vibration substrate 504. The vibration substate 504 comprises a panel configured to be positioned beneath a subject to detect breathing and heartbeat data as described herein. The vibration substrate 504 may be a component of a platform for supporting a subject, such as those described herein, or may be a separate structure that may be configured to be positioned on a platform and/or positioned elsewhere, such as a floor or attached to an underside of a mattress or elsewhere. As above, the breath sensor 269 may be located along the vibration substrate 504 to measure vibrations originating from movements of the back of subject to measure breathing, heartbeat, crying, other sounds or movements. indirectly via vibration detection.

In the illustrated embodiment, the piezoceramic material is attached along an underside 271 surface vibration substrate 504. The vibration substrate 504 may be configured to position below the subject, which in some embodiments includes providing support for the subject and a mattress upon which the subject positions. Attachment may be provided by adhesion to the vibrations substrate 504, e.g., a glue, VHB tape or weld may be used. In other embodiments, the piezoceramic element 502 may be positioned within a vibration substrate 504 structure, such as a housing, which may be similar to sensor housing 304 described above. The piezoceramic element 502 may but need not be positioned at a location corresponding to that of the back of the subject when the subject positioned above the platform 242 as the mechanical vibrations will transmit along the vibration substrate 504 to the piezoceramic element 502.

With further reference to FIG. 24A, the breath sensor 269 may be positioned between platform 242 and a mat, pad, or mattress 277. However, as noted above, the breath sensor 269 or vibration substrate 504 may comprise or be a component of a platform 242 for supporting the subject. When positioned on a platform 242, the vibration substrate 504 may be positioned on or attached to the platform in a manner than does not unnecessarily limit vibration of the vibration substrate 504 from the subject to the piezoceramic element 502. For example, limiting number of attachment sites and applied anchoring stress or other vibration dampening connections may be used to increase detection capabilities.

As introduced above, a mattress 277 may typically be positioned between an upper side 273 of the vibration substrate 504 and the subject to provide comfort to the subject. In some embodiments, the vibration substrate 504 underlays the entire mattress 277, e.g., extends around the entire perimeter of the mattress 277 to support the same. In other embodiments, the vibration substrate 504 underlays only a portion of the mattress 277, which will typically include a location corresponding to the back of the infant.

The piezoceramic element 502 may be provided in various shapes such as round or disc, e.g., as shown, ring-shaped, square, hemispherical, rectangular, geometric, or non-geometric. The piezoceramic element 502 of the breath sensor 269 may be positioned to detect vibrations via deflections along the vibration substrate 504 configured to position below the subject. As introduced above, the vibration substrate 504 may be constructed of a material suitable to transmit vibrations, such as metals, alloys, plastics, fiberglass, fiberboard, or a wood.

The piezoceramic element 502 may transduce vibrations to a measurable voltage signal that may be processed via a processor 507. The processor 507 may be in signal communication with the piezoceramic element 502. The processor 507 may be a component of the breath sensor 269 or separate. The processor 507 may include one or more processing circuits, which may include software processing. In some embodiments, the processor 507 may utilized periodicity patterns, frequency patterns, and/or intensity patterns in the detected signal may be used to filter and identify components in the signal, such as vibrations corresponding to breathing and vibrations corresponding to heartbeat. For example, the processor 507 may analyze the signal as described herein (see, e.g., FIGS. 1-A-1C, 3, 5-8, and 25-29B and accompanying text) to detect and measure breathing and/or heartbeat of a subject. The analysis may determine abnormal breathing or heartbeat, for example, which may include comparison of detected data to one or more breathing or heartbeat profiles. The profiles may be general or specific to the subject. Deviations from profiles may be compared to abnormality profiles, which may be complete profiles or identify ranges of deviations from a general or individual profile of the subject corresponding to an illness, condition, disease, or abnormality. One or more systems or processes herein may be initiated in response, e.g., via output of an emergency call, text, motion of the platform, or sound directed to the subject. The processor 507 may include a processing or conditioning circuit, which may, for example, be provided on a mainboard that electrically couples to the electrical signal output of the piezoceramic element 502. The processor 507 may include a an analog to digital converter, which may be associated with the mainboard to process the signal. Various sample rates may be used considering the signal processing and parameters being measured. For example, the sample rate will typically be at least about 12 kHz to get a 6 kHz Nyquist frequency for vibrational audio resolution for cry detection. In some embodiments, the processor 507 includes a lowpass filter that may be used prior to processing through an analog to digital converter. In some embodiments, the processor 507 processes the breathing and/or heartbeat data as described with respect to the processes of FIG. 1A, 1B, 7, or 8. In some embodiments, the processor 507 corresponds to the breath detection module described with respect to FIG. 1C or 3.

FIGS. 25-29B illustrate example experimental data collected by a breath sensor. The breath sensor comprised a ceramic piezoelectric element (which may also be referred to as a piezoceramic) to collect vibration data related to respiration, heartbeat, and vocalization. The breath sensor was attached to a vibration substrate comprising a metallic panel as described above with respect to FIGS. 23A-23B and positioned below a mattress supporting an infant.

Figure 25:
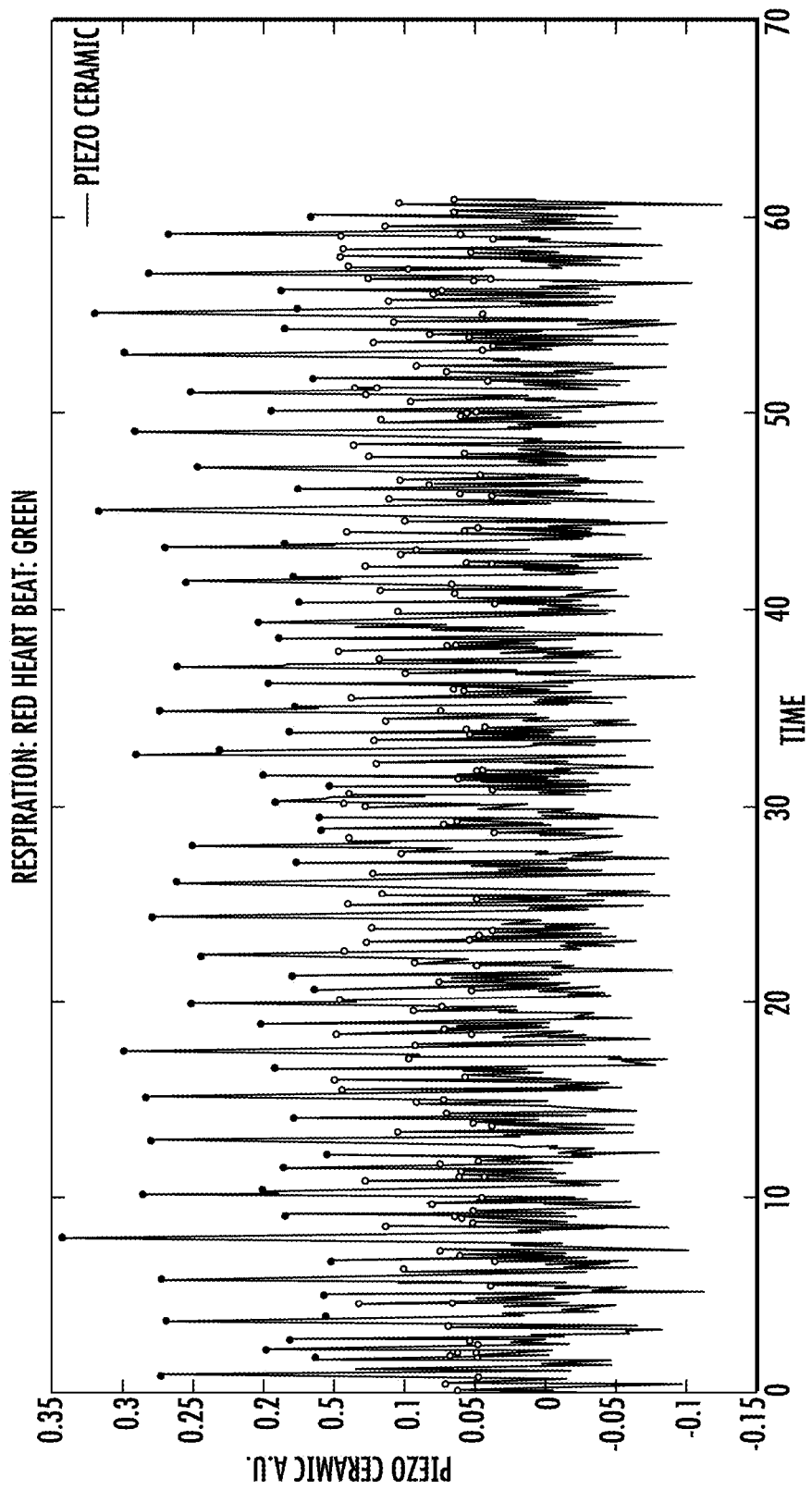
FIG. 25 is a 60 second raw signal generated by a piezoceramic sensor collected when an infant subject was sleeping showing respiration and heartbeat components.
Figure 26:
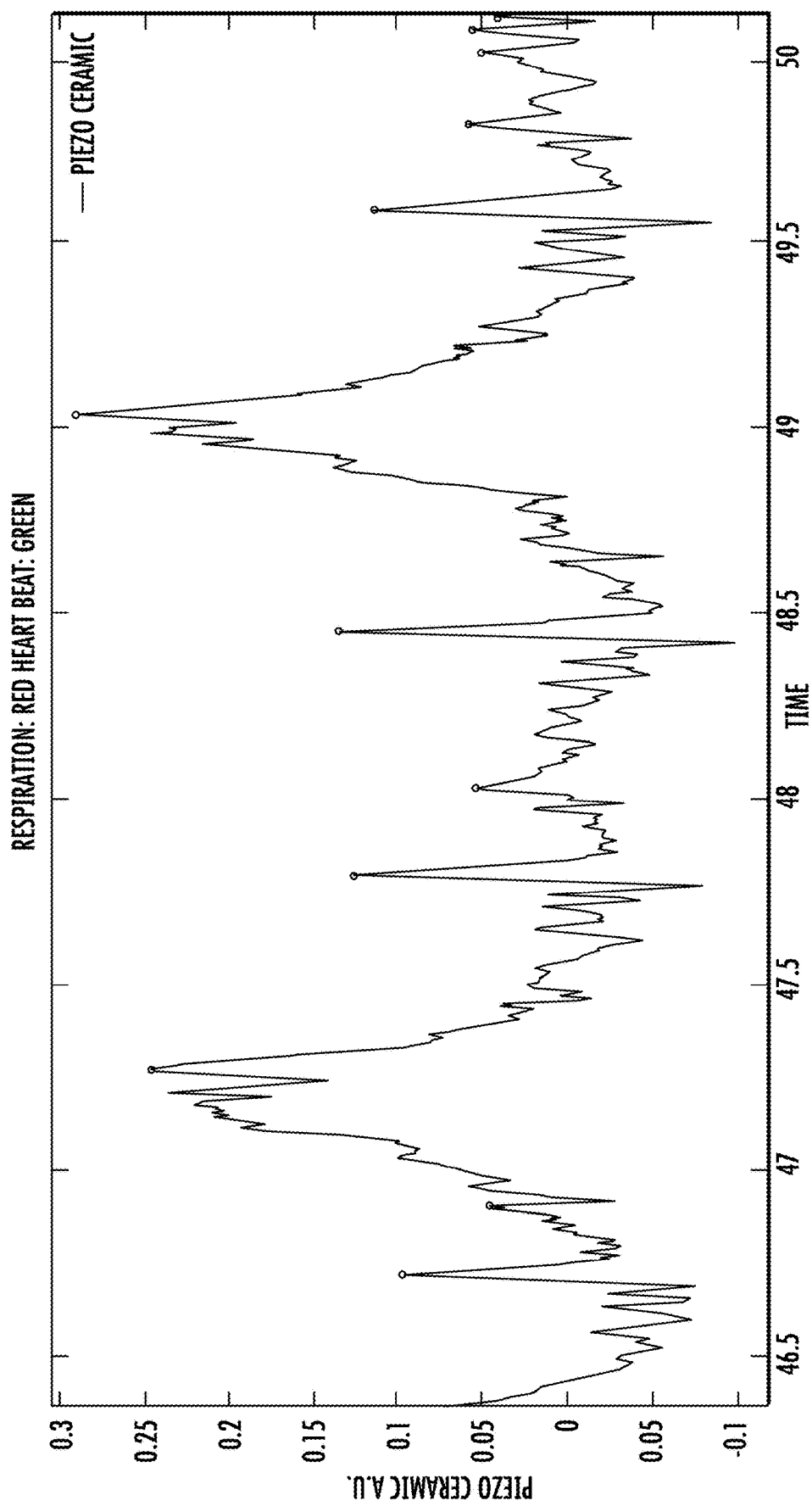
FIG. 26 is a 3.5 second segment of a raw signal generated by a piezoceramic sensor collected when an infant subject was sleeping showing respiration and heartbeat components.
Figure 27:
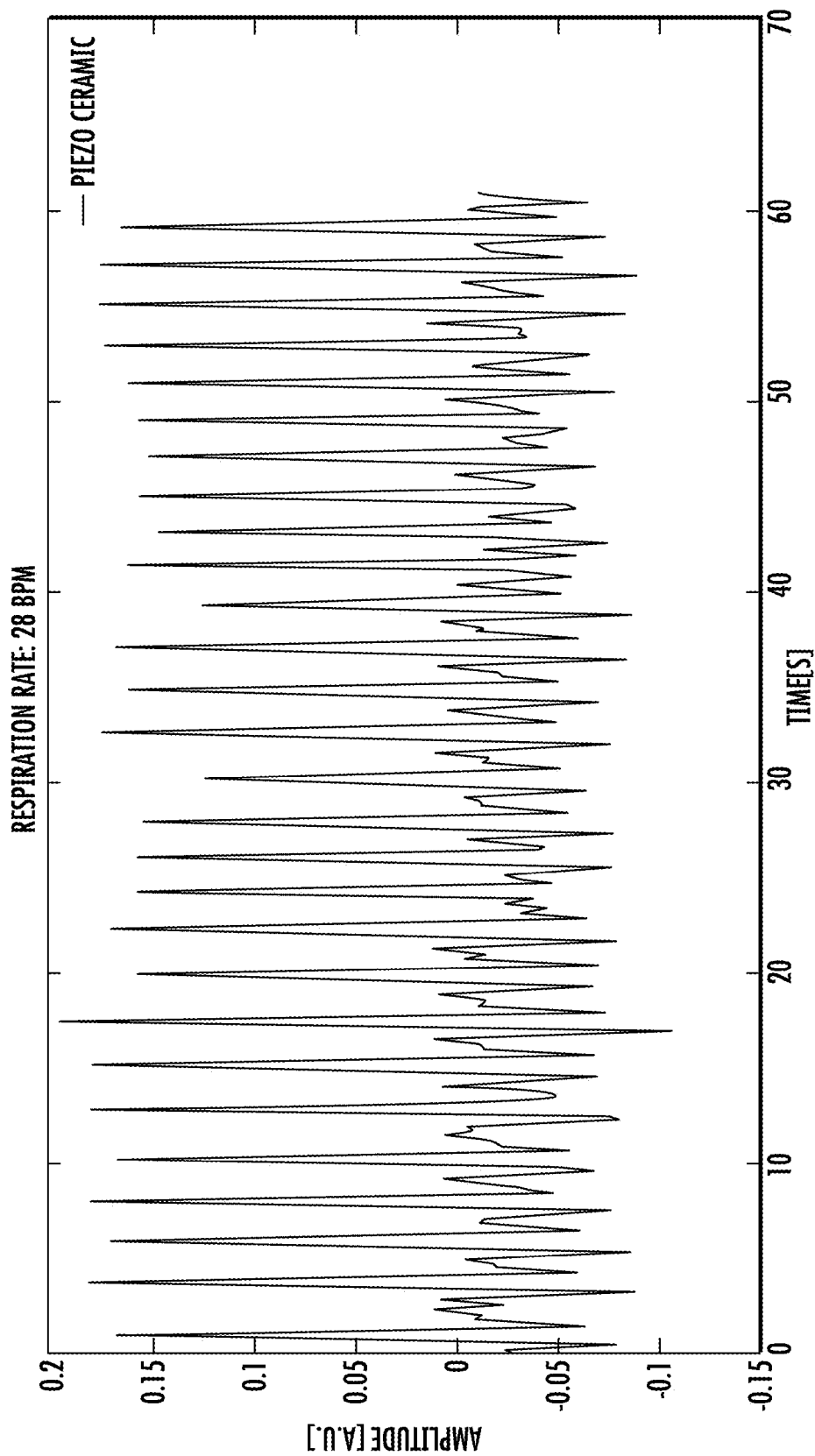
FIG. 27 is the signal in FIG. 25 after processing through a lowpass frequency filter.

For FIGS. 25-27 respiration rate and heartbeat were extracted from a piezoceramic signal from the piezoceramic element attached to the metallic panel. The infant subject was placed on top of a mattress that was supported above the platform, thereby coupling the piezoceramic sensor to the body of the infant, although not directly. With this implementation, the mechanical vibrations generated by the infant were transduced by the sensor.

FIG. 25 is a graph showing the ability of the implementation to pick up the mechanical vibrations of the body of the infant generates when breathing and when the heart beats. In particular, a 60 second segment of the raw signal is shown from when the infant was asleep. Sharp changes indicate the deflection of the sensor which gets transduced as a change in voltage. The raw signal was digitized through a 16-bit ADC converter in a custom circuit.

FIG. 26 shows a section of the raw signal showing two breath events and heart beat signals in between the breath. Typical respiration rate is 20-80 breaths per minute. Typical heart beat is 80-160 beats per minute. Physiological movements related to respiration and heart beat are of low frequency. FIG. 26 depicts low frequency amplitude changes coming directly from the infant.

FIG. 27 shows the signal after processing through a lowpass frequency filter. Respiration events appear as the main component of the signal. The respiration rate remained the same after filtering as well as the general shape of the respiration event.

As introduced above, various embodiments may include a sensor device including multiple sensor types to detect multiple types of data such as motion, sound, temperature, mechanical vibration, acoustic vibration, or the like. The detected data may then be analyzed to enhance specificity of conclusions taken from the data, and which may include comparison of multiple different types of data sources applicable to a particular physical and/or physiological parameter. For example, crying may be analyzed using motion and sound. The acoustic vibration of a cry has both audible and non-audible components, namely an expiration and inspiration component. Utilizing microphones and motion sensors to collect crying associated data may be used to improve cry identification with respect to a particular infant and/or cry characterization. For example, a microphone may be positioned proximate to the infant in a position to detect crying sounds. A sensor device comprising a biometric sensor configured to detect vibrations may be used. For example, a piezoelectric sensor, such as one also referred to herein as a breath sensor, may be used to detect vibrations from movement of the infant. Utilizing this implementation, both mechanical and acoustic vibrations of the infant's body may be detected and analyzed. Hence, the entirety of a cry event: voiced and unvoiced crying, may be advantageously captured.

In various embodiments, with reference back to FIG. 24B, processor 507 may utilize the breath detection sensor 269 for cry detection in combination with a microphone 509 by comparison of a sound signal and the vibration signal. The comparison may be used to confirm movements associated with crying to positively identify the sound as coming from the subject and not an external source. The comparison may be used to confirm crying sounds detected by the sound sensor 509 correspond to movements detected by a vibration based motion sensor, such as piezoceramic element 502 indicative to movements associated with crying, e.g., inhalation corresponding with momentary cessation of cry sounds, and thus the crying sounds are likely to have originated from a child on the platform 242. Thus, correlating of the sound signal to components in the vibration signal may be used to identify sounds as originating from the subject, and not another person proximate to the microphone 509 or other environmental noise. Therefore, vibrations associated with crying measured indirectly through the back of the subject may be used to isolate the signal to sounds originating from a sleep device, such as a crib or bassinet. The comparative processing may save processing steps that may otherwise need to be performed to identify sounds as originating inside sleep device. Sound data collected by the microphone 590 may also be used to isolate movements, e.g., to remove or modulate vibrations associated with vocalization movements detected by the vibration sensor, which is shown as a piezoceramic element 502 in the illustrated embodiment.

FIGS. 28A-29B show experimental data collected utilizing a microphone in combination with a breath sensor comprising a piezoelectric ceramic sensor attached to a platform as in the experimental procedure described with respect to FIGS. 25-27.

FIGS. 28A-28B show a time series of a piezoceramic sensor signal collected during a movement and crying event of infant.

FIG. 28A shows the change in amplitude of the signal, modulated by a low frequency component and high frequency components on top of the signal. FIG. 28B shows a spectrogram analysis, comparing frequency changes over time. The colormap is in logarithmic scale and shows the energy of each frequency component. Cry events show a fundamental component (high energy) at around 400 Hz and harmonics of the cry are also seen across frequencies above 1 kHz.

When microphone data is synchronously collected with the motion/vibration data. The signals may be compared to provide additional information regarding the event. To compare these results, microphone data was collected synchronously.

FIG. 29A show the microphone data time series and FIG. 29B shows the corresponding spectrogram, both of which are synchronized in time with the vibration signal in FIG. 28A-28B. The spectrogram shows only acoustic vibrations picked up by the microphone, namely high frequency components.

Microphones pose the challenge of picking up any sound non-specific to the specific infant that is crying, thus when multiple subjects are in the room, the acoustic vibration detected by a microphone will not be coupled to the mechanical vibration also associated with the crying, which may pose a complicated challenge. The advantage of the solutions described herein where one or more microphones are used to detect acoustic vibrations and one or more vibration sensors are used to detect mechanical vibrations is that the system, processors, breath detection module, or the like may be configured to compare multisource data, e.g., synchronized time series, to analytically couple acoustic vibration to a mechanical vibration, thus making the system more resilient to external sounds and robust with respect to specific infant cry source identification. The one or more vibration sensors may include, breath detection sensors described herein such as piezoelectric sensors, e.g., piezoelectric strip elements and/or piezoelectric ceramic elements.

It is to be appreciated that the breath sensor 269 arrangements described with respect to FIGS. 17-24B may be utilized according to the processes described with respect to FIGS. 1A & 1B or elsewhere to collect data related to subject breathing. Processor 507 may be configured to perform the operations of or be a component of breath detection module 3 described with respect to FIG. 1C or elsewhere or breath detection module 2003 and/or control system 2216 described with respect to FIG. 3 or elsewhere. Further, the sensor device described herein may include the breath sensor 269, such as piezoelectric sensor, e.g., ceramic and/or strip, to detect one or more of breathing, heartbeat, motion or vibrations corresponding to other physiological parameter and thus may be a biometric sensor with respect to any biometric sensor described herein. For example, the sensor device 2 of breath detection system 1 described with respect to FIG. 1C may include breath sensor 269 to detect motion and provide the collected data to breath detection module 3. Similarly, the sensor device 2002 of processing system 1300 may include breath sensor 269, which may also be a biometric sensor 2260, and to detect motion, e.g., motion corresponding to breathing and/or heartbeat, and provide the collected data to breath detection module 2003. In some embodiments, breath sensor 269 may be utilized within the processes and schemes described in FIGS. 5-8. Breath sensor 269 may also be utilized in or with any sleep device or process described or referenced herein, e.g., with a sleep device similar to those described with respect to FIGS. 2A-2B & FIGS. 9-16. In various embodiments, the breath sensor 269 may be utilized with a sleep device including a platform that is movable in various directions and patterns, such as side-to-side rotation about a vertical axis that passes through the platform, side-to-side rotation about a vertical axis that does not pass through the platform, side-to-side laterally transvers to the length dimension of the platform, head-to-toe within a horizontal plane, up-and-down, head-to-toe swinging, side-to-side swinging in an arc relative to an axis of rotation above or below the platform, tilting side-to-side on an axis that passes longitudinally through the platform, or tilting head-to-toe on an axis that basses horizontally through the platform.

The vibration data collected by the breath sensors described herein may be analyzed by machine learning processes such as artificial intelligence to identify medical conditions or abnormalities in the data. The raw or processed signal data, which may include graphs or images representative of the data, such as spectrogram images, may be used as inputs into one or more artificial intelligence or machine learning models with associated algorithm. For example, breath sensor data may be analyzed using such models for detection of SIDS or early detection of medical conditions. In some embodiments, the sleep device, sensor device, breath sensor, and/or processes described herein may be incorporated in or operatively communicate with the infant analysis system described in U.S. Provisional Application 63/161,653, filed Mar. 16, 2021, the contents of which are hereby incorporated herein by reference. For example, the breath sensor data and/or other data collected as described herein may be used by a modeling engine configured with machine learning/artificial intelligence to identify neurological or medical conditions, provide advice or feedback to caregivers, track development and changes overtime, or make comparisons with population data. Breath sensor data may be analyzed for the presence or early detection of respiratory infections or conditions such as cough, cold, croup, asthma, flu, respiratory syncytial virus, or Roseola. For example, small vibrations within the breathing pattern detected by the breath sensor may indicate fluid or other obstructions within the respiratory tract. In some embodiments, the breath sensor data may be combined with sound data detected by one or more microphones to compare detected breathing sounds with motion related to breathing. The comparison may validate detected breathing components or enhance early detection ability by identifying sounds indicative of respiratory issues.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, an example network or system is applicable to software, firmware, and hardware implementations.

In accordance with various embodiments of the present disclosure, the processes described herein may be intended for operation as software programs running on a computer processor. Furthermore, software implementations can include, but are not limited to, distributed processing or component/object distributed processing, parallel processing, cloud processing, or virtual machine processing that may be constructed to implement the methods described herein. In one example, collected subject data is transmitted directly to a breath detection module comprising a remote data processing resource or may transmitted to a connection module for transmission to a data processing resource. The data processing resource may comprise a remote processor, which may be distributed, cloud-based, virtual, and/or comprise a remote application or program executable on a server, for example. The subject data may comprise raw subject data or raw motion data. In one example, the collected subject data transmitted may be preprocessed or partially preprocessed. For example, the collected subject data may be filtered locally at the sensor or a local processing unit and comprise filtered motion data, sound data, pressure/weight data, or combination thereof. A cloud-based service may comprise a public, private, or hybrid cloud processing resource. In an embodiment, the subject data signal processing may be performed on the backend of such a system. For example, all or a portion of the breath detection logic may be in the cloud rather than local, e.g., associated with a bassinet or other device in proximity to the subject being monitored. The backend may similarly be configured to generate and/or initiate alerts based on the data processing, e.g., comparison of current breathing to a general or customized breathing profile.

In one embodiment, a breathing detection system, or breath detection module thereof, includes a remote resource such as a processor, application, program, or the like configured to receive collected subject data. The service may process and analyze the subject data as described herein, e.g., filter data, generate breathing profiles, modify or update breathing profiles, compare current breathing or breathing patterns to general or customized breathing profiles, determine if current breathing or stoppage is abnormal, communicate and/or integrate with hospital monitoring systems or other third party systems, and/or generate or initiate alerts, e.g., phone call, email, light, sounds, motions, text messages, SMS, or push notifications. As noted above, the remote resource may comprise a cloud-based service.

In various embodiments, the breathing detection system may be utilized to detect health conditions detectable from breathing information such as coughs, croup, or the like. Breathing patterns may be compared to previous respiration patterns or profile and/or patterns known to be indicative of one or more respiratory conditions. Respiratory issues that may be detected utilizing breathing data may include, for example, cough, cold, croup, or asthma. In one configuration, the breathing data may be analyzed to identify early on-set of an illness such as respiratory infections, colds, flu, respiratory syncytial virus, or Roseola. For example, the breath detection module may include breathing profiles corresponding to detection of respiratory related conditions. The profiles may include frequency, amplitude, or both corresponding to breathing associated with such health conditions. In some embodiments, separate filtering a processing may be performed on the subject data, which may include motion, sound, or both, as described herein. In various embodiments, the same or similar filtering and processing may be utilized. The system may monitor the subject data and if a health condition is determined from the processing of the subject data, the system may take an action, e.g., generate or initiate and alert, as described herein. As introduced above, the breath detection module or processor may analyze the breathing related data for the presence or early detection of respiratory infections or conditions such as cough, cold, croup, asthma, flu, respiratory syncytial virus, or Roseola. For example, small vibrations within the breathing pattern detected by the breath sensor may indicate fluid or other obstructions within the respiratory tract. In some embodiments, the breath sensor data may be combined with sound data detected by one or more microphones to compare detected breathing sounds with motion related to breathing. The comparison may validate detected breathing components or enhance early detection ability by identifying sounds indicative of respiratory issues.

While infant is used herein to describe the subject of the measured parameters, it is to be appreciated that the subject may be a child or adult without departing for the inventive concepts described herein.

The present disclosure describes various modules, which may also be referred to as sub-modules, systems, subsystems, components, units, and the like. Such modules may include functionally related hardware, instructions, firmware, or software. Modules may include physical or logical grouping of functionally related applications, services, resources, assets, systems, programs, databases, or the like. Modules or hardware storing instructions or configured to execute functionalities of the modules may be physically located in one or more physical locations. For example, modules may be distributed across one or more networks, systems, devices, or combination thereof. It will be appreciated that the various functionalities of these features may be modular, distributed, and/or integrated over one or more physical devices. It will be appreciated that such logical partitions may not correspond to physical partitions of the data. For example, all or portions of various modules may reside or be distributed among one or more hardware locations.

Various embodiments described herein may include a machine-readable medium containing instructions such that a device connected to the communications network, another network, or a combination thereof, can send or receive voice, video or data, and communicate over the communications network, another network, or a combination thereof, using the instructions. The instructions may further be transmitted or received over the communications network, another network, or a combination thereof, via the network interface device. The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure. The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of the systems, modules, and processes that might make use of the structures described herein. While the present disclosure generally describes the breath detection system and process with respect to a bassinet having a moveable platform, movable bassinets are but only one of many potential applications. Indeed, those having skill in the art will appreciate that the breath detection system and processes described herein may find application in many infant apparatuses, such as bouncy chairs, car seats, or other infant apparatuses in which a subject may sleep and that may include significant non-breathing related motion and/or sounds. Other arrangements may be utilized and derived therefrom, such that structural and logical substitutions and changes may be made without departing from the scope of this disclosure.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A system comprising:
a breath sensor configured to be positioned beneath a subject, the breath sensor comprising:
a vibration substrate; and
a piezoceramic element attached to the vibration substrate and configured to detect vibrations propagated along the vibration substrate caused by motion of the subject when positioned on a mattress or pad in vibratory communication with the vibration substrate, wherein the motion corresponds to at least breathing and heartbeat motion of the subject, and wherein the piezoceramic element transduces the detected vibrations into a signal; and
a breath detection module configured to analyze the signal to identify respiration and heartbeat components within the signal, wherein the breath detection module is configured to analyze the respiration components to detect respiratory infections.

2. The system of claim 1, wherein the breath sensor is integrated with the mattress or pad.

3. The system of claim 1, wherein the piezoceramic element is positioned under the mattress or pad.

4. The system of claim 1, further comprising a sleep platform upon which the mattress or pad is positioned and a motor operatively coupled to the sleep platform to drive movement of the sleep platform, wherein the piezoceramic element is configured to detect the vibrations propagated along the vibration substrate caused by motion of the subject when positioned on a mattress or pad while the motor drives movement of the sleep platform, and wherein the breath detection module is configured to filter the signal to remove signal components associated with vibrations corresponding to the movement of the platform by the motor.

5. The system of claim 1, further comprising a sleep platform upon which the mattress or pad is positioned, and wherein the piezoceramic element is attached to an underside of the platform.

6. A system comprising:
a breath sensor configured to be positioned beneath a subject, the breath sensor comprising:
a vibration substrate; and
a piezoceramic element attached to the vibration substrate and configured to detect vibrations propagated along the vibration substrate caused by motion of the subject when positioned on a mattress or pad in vibratory communication with the vibration substrate, wherein the motion corresponds to at least breathing and heartbeat motion of the subject, and wherein the piezoceramic element transduces the detected vibrations into a signal; and
a breath detection module configured to analyze the signal to identify respiration and heartbeat components within the signal, wherein the breath detection module is configured to analyze the respiration components for early detection of respiratory diseases or conditions.

7. The system of claim 6, wherein the breath sensor is integrated with the mattress or pad.

8. The system of claim 6, wherein the piezoceramic element is positioned under the mattress or pad.

9. The system of claim 6, further comprising a sleep platform upon which the mattress or pad is positioned and a motor operatively coupled to the sleep platform to drive movement of the sleep platform, wherein the piezoceramic element is configured to detect the vibrations propagated along the vibration substrate caused by motion of the subject when positioned on a mattress or pad while the motor drives movement of the sleep platform, and wherein the breath detection module is configured to filter the signal to remove signal components associated with vibrations corresponding to the movement of the platform by the motor.

10. A system comprising:
a breath sensor configured to be positioned beneath a subject, the breath sensor comprising:
a vibration substrate; and
a piezoceramic element attached to the vibration substrate and configured to detect vibrations propagated along the vibration substrate caused by motion of the subject when positioned on a mattress or pad in vibratory communication with the vibration substrate, wherein the motion corresponds to at least breathing and heartbeat motion of the subject, and wherein the piezoceramic element transduces the detected vibrations into a signal; and
a breath detection module configured to analyze the signal to identify respiration and heartbeat components within the signal, wherein the breath detection module is configured to analyze the respiration components for early detection of a cough, cold, croup, asthma, flu, respiratory syncytial virus, or Roseola.

11. The system of claim 10, wherein the breath sensor is integrated with the mattress or pad.

12. The system of claim 10, wherein the piezoceramic element is positioned under the mattress or pad.

13. The system of claim 10, further comprising a sleep platform upon which the mattress or pad is positioned and a motor operatively coupled to the sleep platform to drive movement of the sleep platform, wherein the piezoceramic element is configured to detect the vibrations propagated along the vibration substrate caused by motion of the subject when positioned on a mattress or pad while the motor drives movement of the sleep platform, and wherein the breath detection module is configured to filter the signal to remove signal components associated with vibrations corresponding to the movement of the platform by the motor.

14. The system of claim 10, further comprising a sleep platform upon which the mattress or pad is positioned, and wherein the piezoceramic element is attached to an underside of the platform.

15. A system, the system comprising:
a breath sensor comprising:
a vibration substrate comprising an expanse of material configured to receive and propagate vibrations caused by motion of a subject positioned on a mattress or pad positioned over the vibration substrate, and
a piezoceramic element attached to the vibration substrate to transduce the vibrations to an electrical signal;
a microphone positioned to detect sound within the environment of the breath sensor; and
a processor configured to receive and process the electrical signal transduced by the piezoceramic element to identify subject breathing related data, wherein the processor is further configured to receive the sound data and compare the sound data to the subject breathing related data to determine if the sound data originated from the subject positioned on the mattress or pad, wherein the breath detection module is configured to analyze the breathing related data components for early detection of respiratory diseases or conditions.

16. A system, the system comprising:
a breath sensor comprising:

a vibration substrate comprising an expanse of material configured to receive and propagate vibrations caused by motion of a subject positioned on a mattress or pad positioned over the vibration substrate, and a piezoceramic element attached to the vibration substrate to transduce the vibrations to an electrical signal;

a microphone positioned to detect sound within the environment of the breath sensor; and a processor configured to receive and process the electrical signal transduced by the piezoceramic element to identify subject breathing related data, wherein the processor is further configured to receive the sound data and compare the sound data to electrical signal transduced by the piezoceramic element or the subject breathing related data to determine if the sound data originated from the subject positioned on the mattress or pad, wherein the breath detection module is configured to analyze the breathing related data for early detection of a cough, cold, croup, asthma, flu, respiratory syncytial virus, or Roseola.

* * * * *